US011046786B2

(12) United States Patent
Hryhorenko et al.

(10) Patent No.: US 11,046,786 B2
(45) Date of Patent: *Jun. 29, 2021

(54) ANTIBODIES TO OLANZAPINE AND USE THEREOF

(71) Applicant: Janssen Pharmaceutica NV, Beerse (BE)

(72) Inventors: Eric Hryhorenko, Hilton, NY (US); Banumathi Sankaran, Pittsford, NY (US); Thomas R. DeCory, Pittsford, NY (US); Theresa Tubbs, Rochester, NY (US); Linda Colt, Rochester, NY (US); Bart M. Remmerie, Ghent (BE); Rhys Salter, Doylestown, PA (US); Matthew G. Donahue, Hattiesburg, MS (US); Yong Gong, Warrington, PA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,602

(22) Filed: Jun. 17, 2019

(65) Prior Publication Data

US 2019/0315885 A1 Oct. 17, 2019

Related U.S. Application Data

(63) Continuation of application No. 15/299,058, filed on Oct. 20, 2016, now Pat. No. 10,344,098, which is a continuation of application No. 13/971,536, filed on Aug. 20, 2013, now Pat. No. 9,494,608.

(60) Provisional application No. 61/691,645, filed on Aug. 21, 2012.

(51) Int. Cl.
C07K 16/44 (2006.01)
G01N 33/94 (2006.01)

(52) U.S. Cl.
CPC ............. *C07K 16/44* (2013.01); *G01N 33/94* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *G01N 2800/302* (2013.01)

(58) Field of Classification Search
None
See application file for complete search history.

(56) References Cited

U.S. PATENT DOCUMENTS

| | | | |
|---|---|---|---|
| 4,166,452 A | 9/1979 | Generales, Jr. | |
| 5,120,643 A | 6/1992 | Ching et al. | |
| 5,527,709 A | 6/1996 | Danielson et al. | |
| 5,559,041 A | 9/1996 | Kang et al. | |
| 5,587,458 A | 12/1996 | King et al. | |
| 5,641,870 A | 6/1997 | Rinderknecht et al. | |
| 5,642,870 A | 7/1997 | Sargis | |
| 5,714,389 A | 2/1998 | Charlton et al. | |
| 5,761,894 A | 6/1998 | Evans et al. | |
| 6,034,078 A | 3/2000 | Fairburst et al. | |
| 6,139,800 A | 10/2000 | Chandler | |
| 6,228,660 B1 | 5/2001 | May et al. | |
| 7,163,681 B2 | 1/2007 | Giles-Komar et al. | |
| 7,416,700 B2 | 8/2008 | Buechler et al. | |
| 7,772,240 B2 | 8/2010 | Bang-Andersen et al. | |
| 7,901,949 B2 | 3/2011 | Raj | |
| 8,058,405 B2 | 11/2011 | Demuth et al. | |
| 8,088,594 B2 | 1/2012 | Salamone et al. | |
| 9,012,648 B2 | 4/2015 | Haspeslagh et al. | |
| 9,303,041 B2 | 4/2016 | Donahue et al. | |
| 9,304,126 B2 | 4/2016 | Donahue et al. | |
| 9,394,354 B2 | 7/2016 | Haspeslagh et al. | |
| 9,410,972 B2 | 8/2016 | Hryhorenko et al. | |
| 9,434,693 B2 | 9/2016 | Wall et al. | |
| 9,453,002 B2 | 9/2016 | Ahmad et al. | |
| 9,465,041 B2 | 10/2016 | Hryhorenko et al. | |
| 9,494,607 B2 | 11/2016 | Hryhorenko et al. | |
| 9,504,682 B2 | 11/2016 | Lin et al. | |
| 9,611,332 B2 | 4/2017 | Hryhorenko et al. | |
| 9,664,700 B2 | 5/2017 | Hryhorenko et al. | |
| 9,751,953 B2 | 9/2017 | Hryhorenko et al. | |
| 9,795,685 B2 | 10/2017 | Lin et al. | |
| 9,850,318 B2 | 12/2017 | Hryhorenko et al. | |
| 2003/0087306 A1 | 5/2003 | Christensen et al. | |
| 2003/0143233 A1 | 7/2003 | Goshorn et al. | |
| 2003/0202975 A1 | 10/2003 | Tedder | |
| 2004/0127489 A1 | 7/2004 | Pickar et al. | |

(Continued)

FOREIGN PATENT DOCUMENTS

| | | |
|---|---|---|
| CN | 102276592 A | 12/2011 |
| CN | 102276624 A | 12/2011 |

(Continued)

OTHER PUBLICATIONS

International Search Report for Application No. PCT/US2013/055700 dated Oct. 10, 2013.
International Search Report for Application No. PCT/US2013/055712 dated Dec. 13, 2013.
International Search Report for Application No. PCT/US2013/055724 dated Sep. 24, 2013.
International Search Report for corresponding Application No. PCT/US2013/055729 dated Oct. 31, 2013.
International Search Report dated Jan. 16, 2014 for Application No. PCT/US2013/55733.
International Search Report dated Mar. 13, 2014 for Application No. PCT/US2013/55775.

(Continued)

*Primary Examiner* — Andrea S Grossman
(74) *Attorney, Agent, or Firm* — Fay Kaplun & Marcin, LLP

(57) ABSTRACT

Disclosed is an antibody which binds to olanzapine, which can be used to detect olanzapine in a sample such as in a competitive immunoassay method. The antibody can be used in a lateral flow assay device for point-of-care detection of olanzapine, including multiplex detection of aripiprazole, olanzapine, quetiapine, and risperidone in a single lateral flow assay device.

20 Claims, 24 Drawing Sheets

Specification includes a Sequence Listing.

(56) References Cited

U.S. PATENT DOCUMENTS

| | | |
|---|---|---|
| 2005/0163708 A1 | 7/2005 | Robinson et al. |
| 2006/0046967 A1 | 3/2006 | Satyam |
| 2006/0235005 A1 | 10/2006 | Goff |
| 2006/0251592 A1 | 11/2006 | Hendler et al. |
| 2006/0289787 A1 | 12/2006 | Ohman et al. |
| 2007/0231883 A1 | 10/2007 | Lindstrom et al. |
| 2008/0260812 A1 | 10/2008 | Matsuyama et al. |
| 2009/0325193 A1 | 12/2009 | Grenier et al. |
| 2010/0069356 A1 | 3/2010 | Grant et al. |
| 2010/0144781 A1 | 6/2010 | Fu et al. |
| 2010/0203129 A1 | 8/2010 | Andersen et al. |
| 2010/0266502 A1 | 10/2010 | Kimura |
| 2011/0223611 A1 | 9/2011 | Salamone et al. |
| 2011/0230520 A1 | 9/2011 | Sartor et al. |
| 2011/0245224 A1 | 10/2011 | Barvian et al. |
| 2012/0004165 A1 | 1/2012 | Keil et al. |
| 2012/0071636 A1 | 3/2012 | Salamone et al. |
| 2012/0258494 A1 | 10/2012 | Stitz et al. |
| 2014/0057297 A1 | 2/2014 | Hryhorenko et al. |
| 2014/0057298 A1 | 2/2014 | Hryhorenko et al. |
| 2014/0057299 A1 | 2/2014 | Hryhorenko et al. |
| 2014/0057300 A1 | 2/2014 | Hryhorenko et al. |
| 2014/0057301 A1 | 2/2014 | Hryhorenko et al. |
| 2014/0057302 A1 | 2/2014 | Hryhorenko et al. |
| 2014/0057303 A1 | 2/2014 | Hryhorenko et al. |
| 2014/0057305 A1 | 2/2014 | Hryhorenko et al. |
| 2014/0057306 A1 | 2/2014 | Hryhorenko et al. |
| 2014/0155585 A1 | 6/2014 | Haspeslagh et al. |
| 2014/0162997 A1 | 6/2014 | Wall et al. |
| 2014/0163206 A1 | 6/2014 | Lin et al. |
| 2014/0213766 A1 | 7/2014 | Donahue et al. |
| 2014/0213767 A1 | 7/2014 | Haspeslagh et al. |
| 2014/0221616 A1 | 8/2014 | Donahue et al. |
| 2015/0051225 A1 | 2/2015 | Ahmad et al. |

FOREIGN PATENT DOCUMENTS

| | | |
|---|---|---|
| EP | 0582368 B1 | 1/2001 |
| EP | 0583820 B1 | 3/2002 |
| EP | 2 233 503 A1 | 9/2010 |
| EP | 2316468 A1 | 5/2011 |
| JP | 2007535301 A | 12/2007 |
| JP | 6216926 B2 | 10/2017 |
| JP | 6442008 B2 | 12/2018 |
| WO | WO 1992/013876 A1 | 8/1992 |
| WO | WO 95/34652 A1 | 12/1995 |
| WO | WO 1996/30375 A1 | 10/1996 |
| WO | WO 2001/0042787 | 6/2001 |
| WO | WO 03/082877 A1 | 10/2003 |
| WO | WO 03/103835 A1 | 12/2003 |
| WO | WO 04/014895 A1 | 2/2004 |
| WO | WO 05/000901 A2 | 1/2005 |
| WO | WO 05/028458 A1 | 3/2005 |
| WO | WO 05/033073 A2 | 4/2005 |
| WO | WO 05/089082 A2 | 9/2005 |
| WO | WO 05/118139 A1 | 12/2005 |
| WO | WO 06/137785 A1 | 12/2006 |
| WO | WO 09/040409 A1 | 4/2009 |
| WO | WO 10/015029 A1 | 2/2010 |
| WO | WO 2010/048423 A1 | 4/2010 |
| WO | WO 10/104749 A2 | 9/2010 |
| WO | WO-2011/045436 A1 | 4/2011 |
| WO | WO 11/082076 A1 | 7/2011 |
| WO | WO 11/112657 A1 | 9/2011 |
| WO | WO 11/115733 A1 | 9/2011 |
| WO | WO 11/159537 A2 | 12/2011 |
| WO | WO 12/003418 A2 | 1/2012 |
| WO | WO 12/012595 A2 | 1/2012 |
| WO | WO 13/088255 A1 | 6/2013 |
| WO | 2014/031662 A2 | 2/2014 |

OTHER PUBLICATIONS

International Search Report dated Jan. 16, 2014 for Application No. PCT/US2013/55780.
International Search Report dated Mar. 10, 2014 for Application No. PCT/US2013/55787.
International Search Report dated Jan. 16, 2014 for Application No. CDS5130WOPCT.
International Search Report dated Mar. 10, 2014 for Application No. PCT/US2013/55803.
International Search Report dated Jan. 30, 3014 for Application No. PCT/US2013/55817.
International Search Report dated Mar. 3, 2014 for Application No. PCT/US2013/55826.
International Search Report dated Jan. 16, 2014 for Application No. PCT/US2013/55830.
International Search Report dated Mar. 4, 2014 for Application No. PCT/US2013/55834.
International Search Report dated Oct. 31, 2013 for Application No. PCT/US2013/055282.
International Search Report dated Oct. 11, 2013 for Application No. PCT/US2013/055263.
European Search Report dated Mar. 15, 2016, issued in European Application No. 13831110.5.
Chinese Search Report dated Jan. 4, 2016, issued in Chinese Application No. 201380054975.6.
Abdel—Baki, A., et al., "Pharmacotherapy Challenges in Patients with First-Episode Psychosis", Journal of Affective Disorders, vol. 138, pp. S3-S14 (2012).
Aliouane, L., et al., "Synthesis of Difluoromethylphosphonamidates by Directed Addition of Amine", Tetrahedron Letters, vol. 52, pp. 3681-3685 (2011).
Amit et al., "Three-Dimensional Structure of an Antigen-Antibody Complex at 2.8A Resolution", Science, vol. 233, No. 4765, pp. 747-753 (1986).
Annuziato, M., et al., "p-Maleimidophenyl Isocyanate: A Novel Heterobifunctional Linker for Hydroxyl to Thiol Coupling", Bioconjugate Chemistry, vol. 4, pp. 212-218 (1993).
Bilici, M., et al. "The Influence of Olanzapine on Immune Cells in Patients with Schizophrenia". Progress Neuro-Psychopharmacology and Biological Psychiatry, vol. 27, No. 3., pp. 483-485, Published Mar. 31, 2003.
Billah, Md., et al. "Directed Immobilization of Reduced Antibody Fragments onto a Novel SAM on Gold for Myoglobin Impedance Immunosensing", Bioelectrochemistry, vol. 80, pp. 49-54 (2010).
Bodin, A., et al., "Identification and Allergenic Activity of Hydroxyaldehydes-A New Type of Oxidation Product from an Ethylated Non-Ionic Surfactant", Contact Dermatitis, vol. 44, pp. 207-212 (2001).
Brinkley, Michael, "A Brief Survey of Methods for Preparing Protein Conjugates with Dyes, Haptens, and Cross-Linking Reagents", Bioconjugate Chemistry, vol. 3, pp. 2-13 (1992).
Carter, P., et al., "High Level *Escherichia coli* Expression and Production of a Bivalent Humanized Antibody Fragment", Biotechnology, vol. 10, pp. 163-167.
Chamow, S., et al., "Conjugation of Soluble CD4 without Loss of Biological Activity via a Novel Carbohydrate-Directed Cross-Linking Reagent", The Journal of Biological Chemistry, vol. 267, No. 22, Issue of Aug. 5, pp. 15916-15922 (1992).
Chappey, O., et al., "Monoclonal Antibodies in Hapten Immunossays", Pharmaceutical Research, vol. 9, No. 11, pp. 1375-1379 (1992).
Cleland, W. W., "Dithiothreitol, a New Protective Reagent for SH Groups", Biochemistry, vol. 3, No. 4, pp. 480-482 (1964).
Dai, R., et al., "A High-Throughput Assay for Evaluating State Dependence and Subtype Selectivity of Cav2 Calcium Channel Inhibitors", Assay and Drug Development Technologies, vol. 6, No. 2, pp. 195-212 (2008).
Danilova, N., et al., "Production and Characterization of Anti-Theophylline Monoclonal Antibodies Suitable for Immunoassay", Immunology Letters, vol. 29, pp. 79-84 (1991).
Davis, P., et al., "Development and Validation of an LC-MS/MS Method for the Determination of Quetiapine and Four Related

(56) References Cited

OTHER PUBLICATIONS

Metabolites in Human Plasma", Journal of Pharmaceutical and Biomedical Analysis, vol. 51, pp. 1113-1119 (2010).
Diago-Meseguer, J., et al., "A New Reagent for Activating Carboxyl Groups, Preparation and Reactions of N,N-Bis[2-oxo-3-oxazolidinyl)phosphorodiamidic Chloride", Syntheses, vol. 7(1), pp, 547-551 (1980).
Dixon, W.J., "Efficient Analysis of Experimental Observations", Ann. Rev. Pharmacol. Toxicol., vol. 20, pp. 441-462 (1980).
Fiedler, H., et al., "Surface Chemical Characterization of Maleic Acid Mono[2-4-alkylpiperazinyl)ethyl esters]. 1. The Complex Adsorption Behavior of an Ampholytic Surfactant", Langmuir, vol. 10 pp. 3959-3965 (1994).
Finley, F., et al., "An Integrated Multiassay Approach to the Discovery of Small-Molecule N-Type Voltage-Gated Calcium Channel Antagonists", Assay and Drug Development Technologies, vol. 8, No. 6, pp. 685-694 (2010).
Gardner, I., et al., "A Comparison of the Covenant of Clozapine and Olanzapine to Human In Vitro and in Vivo", Molecular Pharmacology, vol. 53. pp. 999-1008 (1998).
Gentaur Molecular Products, Data Sheet, Enzyme Immunoassay for the Detection of Olanzapine in Urine or Serum, 6 pages, (2011).
Ghetie, V., et al., "Preparation and Characterization of Conjugates of Recombinant CD4 and Deglycosylated Ricin A Chain Using Different Cross-Linkers", Bioconaugate Chemistry, vol. 1, pp. 24-31 (1990).
Gorja, D., et al., "Novel N-Indolylmethyl Substituted Olanzapine Derivatives: Their Design, Synthesis and Evaluation as PDE4B Inhibitors+", Organic & Bimolecular Chemistry, vol. 11, pp. 2075-2079 (2013).
Heykants, J., et al., "The Pharmacokinetics of Risperidone in Humans: A Summary", J. Clinical Psychiatry, vol. 55(5), pp. 13-17 (1994).
Huang, M-L, et al., "Pharmacokinetics of the Novel Antipsychotic Agent Risperidone and the Prolactin Response in Healthy Subjects", Clinical Pharmacology Therapeutics, vol. 54, pp. 257-268 (1993).
Huse, W., et al., "Generation of a Large Combinatorial Library of the Immunoglobulin Repertoire in Phage Lambda":, Research Article, pp. 1275-1281 (Dec. 1989).
Ikeda, K. et al., "Development and Validation of a GC-El-MS Method with Reduced Absorption Loss for the Quantification of Olanzapine in Human Plasma", Analytical and Bioanalytical Chemistry, vol. 403, No. 7, pp. 1823-1830 (2012).
Janeway, et al., Immunobiology, Fourth Edition, pp. 86-88, (1999).
Juenke,, J., et al. "A Comparison of Two FDA Approved Lamotrigine Immunoassays with Ultra-High Performance Liquid Chromatography Tandem Mass Spectrometry." *Clinica Chimica Acta, Elsevier BV*, Amsterdam, NL; vol. 412, No. 19, pp. 1878-1882 (2011).
Kim, S., et al., "An Experimental Model for Peripheral Neuropathy Produced by Segmental Spinal Nerve Ligation in the Rat", Pain, vol. 50, pp. 355-363 (1992).
Kirley, Terence L., Reduction and Fluorescent Labeling of Cystϵine-Containing Proteins for Subsequent Structural Analyses, Analytical Biochemistry, vol. 180, pp. 231-236 (1989).
Kohler, C., et al., "Continuous Cultures of Fused Cells Secreting Antibody of Predefined Specificity", Nature, vol. 256, Aug. 7, 1975 pp. 495-497.
Konig, W., et al., "A New Method for Synthesizing Peptides: Activation of Carboxyl Molecules With Dicyclohexylcarbodiimide by Adding 1-Hydroxybenzopartriazles", Chem. Ber. vol. 103, pp. 788-798 (1970).
Li, Z., et al., "Synthesis and Characteristization of N-Benzoyl-N'-Carboxyalkyl Substituted Thiourea Derivatives", Phosphorus, Sulfur and Silicon, vol. 178, pp. 293-297 (2003).
Lieberman, J., et al., "Effectiveness of Antipsychotic Drugs in Patients with Chronic Schizophrenia", The New England Journal of Medicine, vol. 353, pp. 1209-1223 (2005).

Liu, H., et al., "Organophosphorus Compound DEPBT as a Coupling Reagent for Oligopeptides and Peptoids Synthesis: Studies on Its Mechanism", Chinese Chemical Letters, vol. 13, No. 7, pp. 601-604 (2002).
Maddox, D., et al., "Elevated Serum Levels in Human Pregnancy of a Molecule Immunochemically Similar to Eospiophil Granule major Basic Protein", J. Exp. Medicine, vol. 158, pp. 1211-1226 (1983).
Malachowski, W., et al. "The Chemistry of Phosphapeptides: Formation of Functionalized Phosphonochloridates Under Mild Conditions and Their Reaction With Alcohols and Amines", Journal of Organic Chemistry, vol. 59, pp. 7616-7624 (1994).
Modena, D., et al, "Production and Characterization of Murne Monoclonal Antibodies to Polypeptide Hormones and Their Fragments", Annali Dell'Istitto Superiore di Sanita, vol. 27, No. 1, pp. 167-174 (1991).
Needleman, S., et al., "A General Method Applicable to the Search for Similarities in the Amino Acid Sequence of Two Proteins", J. Molecular Biology, vol. 48, pp. 443-453 (1970).
Nielsen, C., et al., "Anti-Allodynic Efficacy of the $\chi$-Conopeptide, Xen2174, in Rats with Neuropathic Pain", Pain, vol. 118, p. 112-124 (2005).
Nolli, M., et al., "Antibodies Against the Antibiotics: An Overview", Annali, Istituto Superiore di Sanita, vol. 27, No. 1, pp. 149-154 (1991).
Park, J., et al., "Novel Cyanine Dyes with Vinylsulfone Group for Labeling Biomolecules", Bioconjugate Chemistry, pp. 350-362 (2012).
Penning, T., et al., "Synthesis of Potent Leukotriene $A_4$ Hydrolase Inhibitors. Identification of 3-[Methyl]4-(phenhlmethyl)-phenooxy]propyl]amino]propanoic Acid", J. Medical Chemistry, vol. 45, pp. 3482-3490 (2002).
Pruhs, S., et al., "Upscaling the Solid-Phase Synthesis of a Tetrahydrocarabazole in Chemical Development" Organic Process Research & Development, vol. 10, pp. 441-445 (2006).
Rudikoff et al.., "Single Amino Acid Substitution Altering Antigen-Binding Specificity", PNAS, vol. 79, pp. 1979-1983 (1982).
Schmid, K., et al., "Distribution of Cyclopropenoid Fatty Acids in Malvaceous Plant Parts", Phytochemistry, vol. 27, No. 9,pp. 2831-2834 (1988).
Smith, T., et al., "Comparison of Biosequences", Advances in Applied Mathematics, vol. 2, pp. 482-489 (1981).
Su, J., et al., "Modification of the Clozapine structure by Parallel Synthesis", Bioorganic & Medicinal Chemistry Letters, vol. 16, p. 4548-4553 (2006).
Subasinghe, N., et al., "A Novel Series of Pyrazolylpiperidine N-Type Calcium Channel Blockers", Bioorganic & Medicinal Chemistry Letters, vol. 22, pp. 4080-4083 (2012).
Van Os, J., et al., "Schizophrenia", Lancet, vol. 74, pp. 635-645 (2009).
Weihua, W. et al. "The Comparison of Metabolic Effects of Antipsychotic Drugs". Journal of Clinical Psychiatry, vol. 19, No. 1., pp. 55-57. Published Feb. 28, 2009. (w/ English Abstract.).
Weisstein, E, "Combination", From MathWorld-A Wolfram Web Resource, http://mathworld.wolfram.com/Combination.html—retrieved Nov. 12, 2014 p. 1.
Wilbur, D., et al., "Reagents for Astatination of Biomolecules; Comparison of the In Vivo Distribution and Stability of Some Radioiodinated/Astatinated Benzamidyl and nido-Carboranyl Compounds", Bioconjugate Chemistry, vol. 15, pp. 203-223 (2004).
Woestenborghs, R., et al, "On the Selectivity of Some Recently Developed RIA's", Methodological Surveys in Biochemistry and Analysis. vol. 20, pp. 241-246 (1990).
Wring, S. et al. "Shorter Development of Immunoassay for Drugs: Application of the Novel RIMMS Technique Enables Rapid Production of Monoclonal Antibodies to Ranitidine." *Journal of Pharmaceutical and Biomedical Analysis*, vol. 19, No. 1: pp. 695-707 (1999).
Wu, X., et al. "A New Homobifunctional p-Nitro Phenyl Ester XCoupling Reagent for the Preparation of Neoglycoproteins", Organic Letters, vol. 6, No. 24, pp. 4407-4410 (2004).
Alphs et al., "Onset of efficacy with acute long-acting injectable paliperidone palmitate treatment in markedly to severely ill patients

(56) References Cited

OTHER PUBLICATIONS with schizophrenia: post hoc analysis of a randomized, double-blind clinical trial," Annals of General Psychiatry, 2011, 10(12): 1-10.
Bergemann, et al., "Olanzapine Plasma Concentration, Average Daily Dose, and interaction with Co-Medication in Schizophrenic Patients," Pharmacopsychiatry, 2004, 34(2): 63-68.
Berna, M., et al., Determination of Olanzapine in Human Plasma and Serum by Liquid Chromatography Tandem Mass Spectrometry, J. Mass Spectrom. 1998; 33(10):1003-1008.
Dusci, LJ, et al., Determinatnion of Olanzapine in Plasma by High performance liquid chromatography using Ultraviolet Performance Detection, J. Chromatogr. B, 2002; 773(20):191-197.
EMEA European Medicines Agency, Assessment Report for Zypadhera, International Nonproprietary Name Olanzapine, 2008:1-63; retrieved Sep. 12, 2017 from http://www.ema.europa.eu/docs/en_GB/document_library/EPAR_-_Public assessment_report/human/000890/WC500054428.pdf.
International Search Report dated Feb. 27, 2014 for Application No. PCT/US2013/055694.
Ji, et al., "Measure of olanzapine blood concentration and the human pharmacokinetics thereof," Journal of China Pharmaceutical University, 2002, 33(5): 397-400.
Mitchell, PB., Therapeutic Drug Monitoring of Psychotropic Medications, Br. J. Clin. Pharmacol., 2000; 49(4) ;303-312.
Tuomola, et al., "Production and characterization of monoclonal antibodies against a very small hapten, 3-methylindole," J. Immunological Methods, 2000; 240:111-124.
Westermann et al., "Simple, rapid and sensitive determination of epinephrine and norepinephrine in unire and plasma by non-competitive enzyme immunoassay, compared with HPLC method," Clin. Lab., 2002; 48:61-71.

ANTIBODIES TO OLANZAPINE AND USE THEREOF

CROSS-REFERENCE TO RELATED APPLICATIONS

This application is a continuation of U.S. patent application Ser. No. 15/299,058, filed Oct. 20, 2016, published on Feb. 9, 2017, as U.S. 2017/0037152, which is a continuation of U.S. patent application Ser. No. 13/971,536, filed Aug. 20, 2013, published on Feb. 27, 2014, as US 2014/0057304, now U.S. Pat. No. 9,494,608, issued on Nov. 15, 2016, and claims the benefit of U.S. Provisional Application No. 61/691,645, filed Aug. 21, 2012, all of which are hereby incorporated by reference in their entireties.

FIELD OF THE INVENTION

The present invention relates to the field of immunoassays, and in particular to antibodies that bind to olanzapine which can be used in immunoassays for detection of olanzapine.

BACKGROUND

Schizophrenia is a chronic and debilitating psychiatric disorder affecting approximately 0.45-1% of the world's population (van Os, J.; Kapur, S. "Schizophrenia" *Lancet* 2009, 374, 635-645). The principal goals of treatment are to achieve sustained remission from psychotic symptoms, reduce the risk and consequences of relapse, and improve patient functioning and overall quality of life. While many patients with schizophrenia are able to achieve symptom stability with the available antipsychotic medications, poor adherence to medication is a common reason for relapse with daily administered oral medications. Several studies (Abdel-Baki, A.; Ouellet-Plamondon, C.; Malla, A. "Pharmacotherapy Challenges in Patients with First-Episode Psychosis" *Journal of Affective Disorders* 2012, 138, S3-S14) investigating the outcomes of non-compliance have shown that patients with schizophrenia who do not take their medication as prescribed have higher rates of relapse, hospital admission and suicide as well as increased mortality. It is estimated that 40 to 75% of patients with schizophrenia have difficulty adhering to a daily oral treatment regimen (Lieberman, J. A.; Stroup, T. S.; McEvoy, J. P.; Swartz, M. S.; Rosenheck, R. A.; Perkins, D. O.; Keefe, R. S. E.; Davis, S. M.; Davis, C. E.; Lebowitz, B. D.; Severe, J.; Hsiao, J. K. "Effectiveness of Antipyschotic Drugs in Patients with Chronic Schizophrenia" *New England Journal of Medicine* 2005, 353(12), 1209-1223).

Therapeutic drug monitoring (TDM) is the quantification of serum or plasma concentrations of drugs, including anti-psychotic drugs, for treatment monitoring and optimization. Such monitoring permits, for example, the identification of patients that are not adhering to their medication regimen, that are not achieving therapeutic doses, that are non-responsive at therapeutic doses, that have suboptimal tolerability, that have pharmacokinetic drug-drug interactions, or that have abnormal metabolism resulting in inappropriate plasma concentrations. Considerable individual variability exists in the patient's ability to absorb, distribute, metabolize, and excrete anti-psychotic drugs. Such differences can be caused by concurrent disease, age, concomitant medication or genetic peculiarities. Different drug formulations can also influence the metabolism of anti-psychotic drugs. TDM permits dose optimization for individual patients, improving therapeutic and functional outcomes. TDM further permits a prescribing clinician to ensure compliance with prescribed dosages and achievement of effective serum concentrations.

To date, methods for determining the levels of serum or plasma concentrations of anti-psychotic drugs involve the use of liquid chromatography (LC) with UV or mass spectrometry detection, and radioimmunoassays (see, for example, Woestenborghs et al., 1990 "On the selectivity of some recently developed RIA's" in Methodological Surveys in Biochemistry and Analysis 20:241-246. Analysis of Drugs and Metabolites, Including Anti-infective Agents; Heykants et al., 1994 "The Pharmacokinetics of Risperidone in Humans: A Summary", J Clin Psychiatry 55/5, suppl:13-17; Huang et al., 1993 "Pharmacokinetics of the novel anti-psychotic agent risperidone and the prolactin response in healthy subjects", Clin Pharmacol Ther 54:257-268). Radioimmunoassays detect one or both of risperidone and paliperidone. Salamone et al. in U.S. Pat. No. 8,088,594 disclose a competitive immunoassay for risperidone using antibodies that detect both risperidone and paliperidone but not pharmacologically inactive metabolites. The antibodies used in the competitive immunoassay are developed against a particular immunogen. ID Labs Inc. (London, Ontario, Canada) markets an ELISA for olanzapine, another anti-psychotic drug, which also utilizes a competitive format. The Instructions For Use indicate that the assay is designed for screening purposes and intended for forensic or research use, and is specifically not intended for therapeutic use. The Instructions recommend that all positive samples should be confirmed with gas chromatography/mass spectrometry (GC-MS), and indicate that the antibody used detects olanzapine and clozapine (see ID Labs Inc., "Instructions For Use Data Sheet IDEL-F083", Rev. Date Aug. 8, 2011). Some of these methods, namely HPLC and GC/MS, can be expensive and labor-intensive, and are generally only performed in large or specialty labs having the appropriate equipment.

A need exists for other methods for determining the levels of anti-psychotic drugs, particularly methods that can be performed in a prescribing clinician's office (where the treatment for an individual patient can be adjusted accordingly in a much more timely manner) and in other medical settings lacking LC or GC/MS equipment or requiring rapid test results.

SUMMARY OF THE INVENTION

The present invention is directed to an isolated antibody or a binding fragment thereof, which binds to olanzapine and which: (i) is an antibody selected from the group consisting of: a) an isolated antibody or a fragment thereof comprising a light chain variable region comprising the amino acid sequence of SEQ ID NO:11, SEQ ID NO:15, SEQ ID NO:31, SEQ ID NO:35 or SEQ ID NO:39; b) an isolated antibody or a fragment thereof comprising a heavy chain variable region comprising the amino acid sequence of SEQ ID NO:12, SEQ ID NO:16, SEQ ID NO:32, SEQ ID NO:36 or SEQ ID NO:40; c) an isolated antibody or a fragment thereof comprising a light chain variable region having the amino acid sequence of SEQ ID NO:11 and a heavy chain variable region having the amino acid sequence of SEQ ID NO:12; d) an isolated antibody or a fragment thereof comprising a light chain variable region having the amino acid sequence of SEQ ID NO:15 and a heavy chain variable region having the amino acid sequence of SEQ ID NO:16; e) an isolated antibody or a fragment thereof comprising a light chain variable region having the amino acid sequence of SEQ ID NO:31 and a heavy chain variable region having the amino acid sequence of SEQ ID NO:32; f) an isolated antibody or a fragment thereof comprising a light chain variable region having the amino acid sequence of SEQ ID NO:35 and a heavy chain variable region having the amino acid sequence of SEQ ID NO:36; or g) an isolated antibody or a fragment thereof comprising a light chain variable region having the amino acid sequence of SEQ ID NO:39 and a heavy chain variable region having the amino acid sequence of SEQ ID NO:40; or (ii) competes for an epitope which is the same as an epitope bound by the antibody of (i).

The antibodies of the subject invention can be provided in assay kits and assay devices, with a presently preferred device being a lateral flow assay device which provides for point-of-care analysis.

The invention further provides a method of detecting olanzapine in a sample. The method comprises: (i) contacting a sample with an antibody according to the subject invention which is labeled with a detectable marker, wherein the labeled antibody and olanzapine present in the sample form a labeled complex; and (ii) detecting the labeled complex so as to detect olanzapine in the sample.

Further provided is a competitive immunoassay method for detecting olanzapine in a sample. The method comprises: (i) contacting a sample with an antibody according to the subject invention, and with olanzapine or a competitive binding partner of olanzapine, wherein one of the antibody and the olanzapine or competitive binding partner thereof is labeled with a detectable marker, and wherein sample olanzapine competes with the olanzapine or competitive binding partner thereof for binding to the antibody; and (ii) detecting the label so as to detect sample olanzapine.

Further objects, features and advantages of the present invention will be apparent to those skilled in the art from detailed consideration of the preferred embodiments that follow.

DETAILED DESCRIPTION OF PREFERRED EMBODIMENTS

Figure 1:
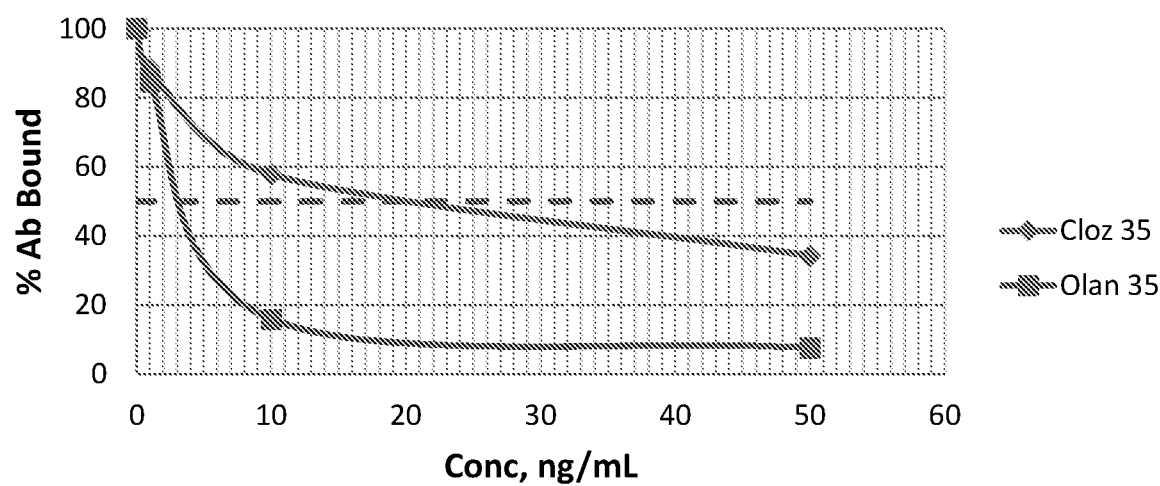
FIGS. 1-3 show Competitive ELISA results generated with three different mouse fusion 11.1 hybridomas.

The following terms are used to describe the sequence relationships between two or more polynucleotide or amino acid sequences: "reference sequence", "comparison window", "sequence identity", "percentage of sequence identity", "substantial identity", "similarity", and "homologous". A "reference sequence" is a defined sequence used as a basis for a sequence comparison; a reference sequence may be a subset of a larger sequence, for example, a segment of a full length cDNA or gene sequence given in a sequence listing or may comprise a complete cDNA or gene sequence; a reference sequence may comprise a segment of a complete amino acid sequence encoding a protein as given in a sequence listing or may comprise a complete amino acid sequence encoding a protein. Generally, a reference sequence is at least 18 nucleotides or 6 amino acids in length, frequently at least 24 nucleotides or 8 amino acids in length, and often at least 48 nucleotides or 16 amino acids in length. Since two polynucleotide or amino acid sequences may each (1) comprise a sequence (i.e., a portion of the complete nucleotide or amino acid sequence) that is similar between the two molecules, and (2) may further comprise a sequence that is divergent between the two polynucleotide or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein the polynucleotide sequence or amino acid sequence may be compared to a reference sequence of at least 18 contiguous nucleotides or 6 amino acids and wherein the portion of the polynucleotide sequence or amino acid sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, Adv. Appl. Math 2:482 (1981), by the homology alignment algorithm of Needlemen and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package Release 7.0 (Genetics Computer Group, 575 Science Dr., Madison, Wis.), Geneworks or MacVector software packages), or by inspection, and the best alignment (i.e., resulting in the highest percentage of identity over the comparison window) generated by the various methods is selected.

The term "sequence identity" means that two polynucleotide or amino acid sequences are identical (i.e., on a nucleotide-by-nucleotide or amino acid residue-by-residue basis) over the comparison window. The term "percentage of sequence identity" is calculated by comparing two optimally aligned sequences over the window of comparison, determining the number of positions at which the identical nucleic acid base (e.g., A, T, C, G, or U) or amino acid residue occurs in both sequences to yield the number of matched positions, dividing the number of matched positions by the total number of positions in the comparison window (i.e., the window size), and multiplying the result by 100 to yield the percentage of sequence identity. The term "substantial identity" as used herein denotes a characteristic of a polynucleotide or amino acid sequence, wherein the polynucleotide or amino acid sequence comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. The term "similarity", when used to describe a polypeptide, is determined by comparing the amino acid sequence and the conserved amino acid substitutions of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98% to 99% of the nucleotides.

A "label," "detector molecule," "reporter" or "detectable marker" as used herein is any molecule which produces, or can be induced to produce, a detectable signal. The label can be conjugated to an analyte, immunogen, antibody, or to another molecule such as a receptor or a molecule that can bind to a receptor such as a ligand, particularly a hapten or antibody. A label can be attached directly or indirectly by means of a linking or bridging moiety. Non-limiting examples of labels include radioactive isotopes (e.g., $^{125}$I), enzymes (e.g. β-galactosidase, peroxidase), enzyme fragments, enzyme substrates, enzyme inhibitors, coenzymes, catalysts, fluorophores (e.g., rhodamine, fluorescein isothiocyanate or FITC, or Dylight 649), dyes, chemiluminescers and luminescers (e.g., dioxetanes, luciferin), or sensitizers.

The invention provides an isolated antibody which binds to olanzapine. The invention further provides an assay kit and an assay device comprising the antibody. Further provided is a method of detecting olanzapine in a sample, including a competitive immunoassay method.

In one embodiment, the present invention is directed to an isolated antibody or a binding fragment thereof, which binds to olanzapine and which: is an antibody selected from the group consisting of: a) an isolated antibody or a fragment thereof comprising a light chain variable region comprising the amino acid sequence of SEQ ID NO:11, SEQ ID NO:15, SEQ ID NO:31, SEQ ID NO:35 or SEQ ID NO:39; b) an isolated antibody or a fragment thereof comprising a heavy chain variable region comprising the amino acid sequence of SEQ ID NO:12, SEQ ID NO:16, SEQ ID NO:32, SEQ ID NO:36 or SEQ ID NO:40; c) an isolated antibody or a fragment thereof comprising a light chain variable region having the amino acid sequence of SEQ ID NO:11 and a heavy chain variable region having the amino acid sequence of SEQ ID NO:12; d) an isolated antibody or a fragment thereof comprising a light chain variable region having the amino acid sequence of SEQ ID NO:15 and a heavy chain variable region having the amino acid sequence of SEQ ID NO:16; e) an isolated antibody or a fragment thereof comprising a light chain variable region having the amino acid sequence of SEQ ID NO:31 and a heavy chain variable region having the amino acid sequence of SEQ ID NO:32; f) an isolated antibody or a fragment thereof comprising a light chain variable region having the amino acid sequence of SEQ ID NO:35 and a heavy chain variable region having the amino acid sequence of SEQ ID NO:36; or g) an isolated antibody or a fragment thereof comprising a light chain variable region having the amino acid sequence of SEQ ID NO:39 and a heavy chain variable region having the amino acid sequence of SEQ ID NO:40; or (ii) competes for an epitope which is the same as an epitope bound by the antibody of (i).

In a further embodiment, the present invention is directed to an isolated antibody or a binding fragment thereof, which binds to olanzapine and which comprises a light chain variable region comprising an amino acid sequence having at least 80% sequence identity with SEQ ID NO:11, SEQ ID NO:15, SEQ ID NO:31, SEQ ID NO:35 or SEQ ID NO:39.

In a further embodiment, the present invention is directed to an isolated antibody or a binding fragment thereof, which binds to olanzapine and which comprises a heavy chain variable region comprising an amino acid sequence having at least 80% sequence identity with SEQ ID NO:12, SEQ ID NO:16, SEQ ID NO:32, SEQ ID NO:36 or SEQ ID NO:40.

Presently preferred embodiments of the antibody of the subject invention are: an antibody which comprises a light chain variable region having the amino acid sequence SEQ ID NO:11 and a heavy chain variable region having the amino acid sequence SEQ ID NO:12; an antibody which comprises a light chain variable region having the amino acid sequence SEQ ID NO:15 and a heavy chain variable region having the amino acid sequence SEQ ID NO:16; an antibody which comprises a light chain variable region having the amino acid sequence SEQ ID NO:31 and a heavy chain variable region having the amino acid sequence SEQ ID NO:32; an antibody which comprises a light chain variable region having the amino acid sequence SEQ ID NO:35 and a heavy chain variable region having the amino acid sequence SEQ ID NO:36; and an antibody which comprises a light chain variable region having the amino acid sequence SEQ ID NO:39 and a heavy chain variable region having the amino acid sequence SEQ ID NO:40.

Additional presently preferred embodiments of the antibody of the subject invention are: 1) an antibody which comprises a light chain CDR1 sequence comprising amino acid residues 44 to 54 of SEQ ID NO:11, a light chain CDR2 sequence comprising amino acid residues 70 to 76 of SEQ ID NO:11, a light chain CDR3 sequence comprising amino acid residues 109 to 117 of SEQ ID NO:11, a heavy chain CDR1 sequence comprising amino acid residues 45 to 54 of SEQ ID NO:12, a heavy chain CDR2 sequence comprising amino acid residues 69 to 85 of SEQ ID NO:12, and a heavy chain CDR3 sequence comprising amino acid residues 118 to 122 of SEQ ID NO:12; 2) an antibody which comprises a light chain CDR1 sequence comprising amino acid residues 44 to 54 of SEQ ID NO:15, a light chain CDR2 sequence comprising amino acid residues 70 to 76 of SEQ ID NO:15, a light chain CDR3 sequence comprising amino acid residues 109 to 117 of SEQ ID NO:15, a heavy chain CDR1 sequence comprising amino acid residues 45 to 54 of SEQ ID NO:16, a heavy chain CDR2 sequence comprising amino acid residues 69 to 85 of SEQ ID NO:16, and a heavy chain CDR3 sequence comprising amino acid residues 118 to 122 of SEQ ID NO:16; 3) an antibody which comprises a light chain CDR1 sequence comprising amino acid residues 44 to 54 of SEQ ID NO:31, a light chain CDR2 sequence comprising amino acid residues 70 to 76 of SEQ ID NO:31, a light chain CDR3 sequence comprising amino acid residues 109 to 117 of SEQ ID NO:31, a heavy chain CDR1 sequence comprising amino acid residues 44 to 54 of SEQ ID NO:32, a heavy chain CDR2 sequence comprising amino acid residues 69 to 84 of SEQ ID NO:32, and a heavy chain CDR3 sequence comprising amino acid residues 119 to 127 of SEQ ID NO:32; 4) an antibody which comprises a light chain CDR1 sequence comprising amino acid residues 44 to 54 of SEQ ID NO:35, a light chain CDR2 sequence comprising amino acid residues 70 to 76 of SEQ ID NO:35, a light chain CDR3 sequence comprising amino acid residues 109 to 117 of SEQ ID NO:35, a heavy chain CDR1 sequence comprising amino acid residues 45 to 54 of SEQ ID NO:36, a heavy chain CDR2 sequence comprising amino acid residues 69 to 87 of SEQ ID NO:36, and a heavy chain CDR3 sequence comprising amino acid residues 120 to 127 of SEQ ID NO:36; and 5) an antibody which comprises a light chain CDR1 sequence comprising amino acid residues 44 to 54 of SEQ ID NO:39, a light chain CDR2 sequence comprising amino acid residues 70 to 76 of SEQ ID NO:39, a light chain CDR3 sequence comprising amino acid residues 109 to 117 of SEQ ID NO:39, a heavy chain CDR1 sequence comprising amino acid residues 44 to 54 of SEQ ID NO:40, a heavy chain CDR2 sequence comprising amino acid residues 69 to 84 of SEQ ID NO:40, and a heavy chain CDR3 sequence comprising amino acid residues 120 to 127 of SEQ ID NO:40.

Further details of the antibodies of the subject invention are provided in the section below entitled "Antibodies".

The subject invention further provides an assay kit comprising the antibody, as well as an assay device comprising the antibody. Preferably, the assay device is a lateral flow assay device. Further details of the assay kits and assay devices are provided below in the section entitled "Assay Kits and Devices".

The invention further provides a method of detecting olanzapine in a sample. The method comprises: (i) contacting a sample with an antibody according to the subject invention which is labeled with a detectable marker, wherein the labeled antibody and olanzapine present in the sample form a labeled complex; and (ii) detecting the labeled complex so as to detect olanzapine in the sample. Further details of the method of detecting olanzapine in accordance with the subject invention are provided in the section below entitled "Immunoassays".

Further provided is a competitive immunoassay method for detecting olanzapine in a sample. The method comprises: (i) contacting a sample with an antibody according to the subject invention, and with olanzapine or a competitive binding partner of olanzapine, wherein one of the antibody and the olanzapine or competitive binding partner thereof is labeled with a detectable marker, and wherein sample olanzapine competes with the olanzapine or competitive binding partner thereof for binding to the antibody; and (ii) detecting the label so as to detect sample olanzapine. Further details of the competitive immunoassay method of detecting olanzapine in accordance with the subject invention are provided in the section below entitled "Immunoassays".

In a preferred embodiment of the subject invention, the detection of olanzapine is accompanied by the detection of one or more analytes in addition to olanzapine. Preferably the one or more analytes are anti-psychotic drugs other than olanzapine, and more preferably the anti-psychotic drugs other than olanzapine are selected from the group consisting of: aripiprazole, risperidone, paliperidone, quetiapine, and metabolites thereof.

As discussed above, the antibodies of the subject invention can be used in assays to detect the presence and/or amount of the anti-psychotic drug in patient samples. Such detection permits therapeutic drug monitoring enabling all of the benefits thereof. Detection of levels of anti-psychotic drugs may be useful for many purposes, each of which represents another embodiment of the subject invention, including: determination of patient adherence or compliance with prescribed therapy; use as a decision tool to determine whether a patient should be converted from an oral antipsychotic regimen to a long-acting injectable anti-psychotic regimen; use as a decision tool to determine if the dose level or dosing interval of oral or injectable anti-psychotics should be increased or decreased to ensure attainment or maintenance of efficacious or safe drug levels; use as an aid in the initiation of anti-psychotic drug therapy by providing evidence of the attainment of minimum pK levels; use to determine bioequivalence of anti-psychotic drug in multiple formulations or from multiple sources; use to assess the impact of polypharmacy and potential drug-drug interactions; and use as an indication that a patient should be excluded from or included in a clinical trial and as an aid in the subsequent monitoring of adherence to clinical trial medication requirements.

Antibodies

The present invention provides an isolated antibody which binds to olanzapine. The term "antibody" refers to a specific protein capable of binding an antigen or portion thereof (in accordance with this invention, capable of binding to an anti-psychotic drug or metabolite thereof). An antibody is produced in response to an immunogen which may have been introduced into a host, e.g., an animal or a human, by injection. The generic term "antibody" includes polyclonal antibodies, monoclonal antibodies, and antibody fragments.

"Antibody" or "antigen-binding antibody fragment" refers to an intact antibody, or a fragment thereof, that competes with the intact antibody for binding. Generally speaking, an antibody or antigen-binding antibody fragment, is said to specifically bind an antigen when the dissociation constant is less than or equal to 1 µM, preferably less than or equal to 100 nM and most preferably less than or equal to 10 nM. Binding can be measured by methods know to those skilled in the art, an example being the use of a BIAcore™ instrument.

Antibodies are made up of two heavy chains and two light chains. Each heavy chain has one variable domain or region ($V_H$) followed by a constant domain or region ($C_H1$), a hinge region, and two more constant domains or regions ($C_H2$ and $C_H3$). Each light chain has one variable domain or region ($V_L$) and one constant domain or region (CO. The variable domains or regions of the heavy and light chains form the paratope of the antibody (a structure analogous to a lock), which is specific for a particular epitope (similarly analogous to a key), allowing the paratope and the epitope to bind together with precision. Within the variable domain, variable loops of β-strands, three each on the light and heavy chains, are responsible for binding to the antigen. These loops are referred to as the complementarity determining regions (CDRs, namely CDR1, CDR2, and CDR3).

Antibody fragments comprise a portion of an intact antibody, preferably the antigen binding or variable region of the intact antibody. Binding fragments include Fab, Fab', F(ab')$_2$, and Fv fragments; diabodies; minibodies; linear antibodies; single-chain antibody molecules (e.g., scFV); and multispecific antibodies formed from antibody fragments. An antibody other than a "bispecific" or "bifunctional" antibody is understood to have each of its binding sites identical.

As used herein, "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to "bind the same epitope" ("compete") if one antibody is shown to compete with the second antibody in a competitive binding assay, by any of the methods well known to those skilled in the art (such as the BIAcore™ method referred to above). In reference to a hapten (such as olanzapine or other anti-psychotic drug), an antibody can be generated against the non-antigenic hapten molecule by conjugating the hapten to an immunogenic carrier. An antibody is then generated which recognizes an "epitope" defined by the hapten.

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated", but the same antibody separated from the coexisting materials of its natural state is "isolated", as the term is employed herein. Antibodies may occur in a composition, such as an immunoassay reagent, which are not naturally occurring compositions, and therein remain isolated antibodies within the meaning of that term as it is employed herein.

"Cross-reactivity" refers to the reaction of an antibody with an antigen that was not used to induce that antibody.

Preferably, the antibody of the subject invention will bind to the drug and any desired pharmacologically active metabolites. By altering the location of the attachment of an immunogenic carrier in a drug conjugate, selectivity and cross-reactivity with metabolites and/or related drugs can be engineered into the antibodies. For olanzapine, cross-reactivity with the related drug clozapine may or may not be desirable, and cross reactivity with olanzapine metabolites such as 10-N-gluronide or 4-N-desmethyl olanzapine may or may not be desirable. Antibodies may be generated that detect multiple ones of these drugs and/or metabolites, or antibodies may be generated that detect each separately (thus defining the antibody "specific binding" properties). An antibody specifically binds one or more compounds when its binding of the one or more compounds is equimolar or substantially equimolar.

The antibodies herein are described by the nucleotide and amino acid sequences of their variable domains. Each was generated by inoculating a host with a conjugate comprising an anti-psychotic drug conjugated to an immunogenic carrier. Having now provided the nucleotide and amino acid sequences thereof, the antibodies can be produced by the recombinant methods such as are described in U.S. Pat. No. 4,166,452.

Antibody fragments which contain specific binding sites for the anti-psychotic drug may also be generated. Such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., Science 256:1270-1281 (1989)). Fab, Fv and ScFv antibody fragments can all be expressed in and secreted from *Escherichia coli*, allowing for the production of large amounts of these fragments. Alternatively, Fab'-SH fragments can be directly recovered from *E. coli* and chemically coupled to form F(ab')$_2$ fragments (Carter et al., *BioTechnology* 10:163-167 (1992)). Other techniques for the production of antibody fragments are known to those skilled in the art. Single chain Fv fragments (scFv) are also envisioned (see U.S. Pat. Nos. 5,761,894 and 5,587,458). Fv and sFv fragments are the only species with intact combining sites that are devoid of constant regions; thus, they are likely to show reduced non-specific binding. The antibody fragment may also be a "linear antibody" e.g., as described in U.S. Pat. No. 5,642,870, for example. Such linear antibody fragments may be monospecific or bispecific.

Assay Kits and Devices

An assay kit (also referred to as a reagent kit) can also be provided comprising an antibody as described above. A representative reagent kit may comprise an antibody that binds to the anti-psychotic drug, olanzapine, a complex comprising an analog of an anti-psychotic drug or a derivative thereof coupled to a labeling moiety, and may optionally also comprise one or more calibrators comprising a known amount of an anti-psychotic drug or a related standard.

The phrase "assay kit" refers to an assembly of materials and reagents that is used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. An assay kit embodying features of the present invention comprises antibodies which bind olanzapine. The kit may further comprise competitive binding partners of olanzapine and calibration and control materials.

The phrase "calibration and control material" refers to any standard or reference material containing a known amount of an analyte. A sample suspected of containing an analyte and the corresponding calibration material are assayed under similar conditions. The concentration of analyte is calculated by comparing the results obtained for the unknown specimen with the results obtained for the standard. This is commonly done by constructing a calibration curve.

Antibodies embodying features of the present invention can be included in a kit, container, pack, or dispenser together with instructions for their utilization. When the antibodies are supplied in a kit, the different components of the immunoassay may be packaged in separate containers and admixed prior to use. Such packaging of the components separately may permit long-term storage without substantially diminishing the functioning of the active components. Furthermore, reagents can be packaged under inert environments, e.g., under a positive pressure of nitrogen gas, argon gas, or the like, which is especially preferred for reagents that are sensitive to air and/or moisture.

Reagents included in kits embodying features of the present invention can be supplied in all manner of containers such that the activities of the different components are substantially preserved while the components themselves are not substantially adsorbed or altered by the materials of the container. Suitable containers include, but are not limited to, ampules, bottles, test tubes, vials, flasks, syringes, envelopes, e.g., foil-lined, and the like. The containers may be comprised of any suitable material including, but not limited to, glass, organic polymers, e.g., polycarbonate, polystyrene, polyethylene, etc., ceramic, metal, e.g., aluminum, metal alloys, e.g., steel, cork, and the like. In addition, the containers may comprise one or more sterile access ports, e.g., for access via a needle, such as may be provided by a septum. Preferred materials for septa include rubber and polytetrafluoroethylene of the type sold under the trade name TEFLON by DuPont (Wilmington, Del.). In addition, the containers may comprise two or more compartments separated by partitions or membranes that can be removed to allow mixing of the components.

Reagent kits embodying features of the present invention may also be supplied with instructional materials. Instructions may be printed, e.g., on paper and/or supplied in an electronically-readable medium. Alternatively, instructions may be provided by directing a user to an Internet website, e.g., specified by the manufacturer or distributor of the kit and/or via electronic mail.

The antibody may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

In a non-porous assay device, the assay device generally has at least one sample addition zone, at least one conjugate zone, at least one reaction zone, and at least one wicking zone. The zones form a flow path by which sample flows from the sample addition zone to the wicking zone. Also included are capture elements, such as antibodies, in the reaction zone, capable of binding to the analyte, optionally deposited on the device (such as by coating); and a labeled conjugate material also capable of participating in reactions that will enable determination of the concentration of the analyte, deposited on the device in the conjugate zone, wherein the labeled conjugate material carries a label for detection in the reaction zone. The conjugate material is dissolved as the sample flows through the conjugate zone forming a conjugate plume of dissolved labeled conjugate material and sample that flows downstream to the reaction zone. As the conjugate plume flows into the reaction zone, the conjugated material will be captured by the capture elements such as via a complex of conjugated material and analyte (as in a "sandwich" assay) or directly (as in a "competitive" assay). Unbound dissolved conjugate material will be swept past the reaction zone into the at least one wicking zone. Such devices can include projections or micropillars in the flow path.

An instrument such as that disclosed in US Patent Publication Nos. US20060289787A1 and US 20070231883A1, and U.S. Pat. Nos. 7,416,700 and 6,139,800, all of which are incorporated herein by reference in their entireties, is able to detect the bound conjugated material in the reaction zone. Common labels include fluorescent dyes that can be detected by instruments which excite the fluorescent dyes and incorporate a detector capable of detecting the fluorescent dyes.

Immunoassays

The antibodies thus produced can be used in immunoassays to recognize/bind to the anti-psychotic drug, thereby detecting the presence and/or amount of the drug in a patient sample. Preferably, the assay format is a competitive immunoassay format. Such an assay format and other assays are described, among other places, in Hampton et al. (*Serological Methods, A Laboratory Manual*, APS Press, St. Paul, Minn. 1990) and Maddox et al. (J. Exp. Med. 158:12111, 1983).

The term "analyte" refers to any substance or group of substances, the presence or amount of which is to be determined. Representative anti-psychotic drug analytes include, but are not limited to, risperidone, paliperidone, olanzapine, aripiprazole, and quetiapine.

The term "competitive binding partner" refers to a substance or group of substances, such as may be employed in a competitive immunoassay, which behave similarly to an analyte with respect to binding affinity to an antibody. Representative competitive binding partners include, but are not limited to, anti-psychotic drug derivatives and the like.

The term "detecting" when used with an analyte refers to any quantitative, semi-quantitative, or qualitative method as well as to all other methods for determining an analyte in general, and an anti-psychotic drug in particular. For example, a method that merely detects the presence or absence of an anti-psychotic drug in a sample lies within the scope of the present invention, as do methods that provide data as to the amount or concentration of the anti-psychotic drug in the sample. The terms "detecting", "determining", "identifying", and the like are used synonymously herein, and all lie within the scope of the present invention.

A preferred embodiment of the subject invention is a competitive immunoassay wherein antibodies which bind the anti-psychotic drug, or the drug or competitive binding partner thereof, are attached to a solid support (such as the reaction zone in a lateral flow assay device) and labeled drug or competitive binding partner thereof, or labeled antibody, respectively, and a sample derived from the host are passed over the solid support and the amount of label detected attached to the solid support can be correlated to a quantity of drug in the sample.

Any sample that is suspected of containing an analyte, e.g., an anti-psychotic drug, can be analyzed in accordance with the methods of the presently preferred embodiments. The sample can be pretreated if desired and can be prepared in any convenient medium that does not interfere with the assay. Preferably, the sample comprises an aqueous medium such as a body fluid from a host, most preferably plasma or serum.

It is to be understood that all manner of immunoassays employing antibodies are contemplated for use in accordance with the presently preferred embodiments, including assays in which antibodies are bound to solid phases and assays in which antibodies are in liquid media. Methods of immunoassays that can be used to detect analytes using antibodies embodying features of the present invention include, but are not limited to, competitive (reagent limited) assays wherein labeled analyte (analyte analog) and analyte in a sample compete for antibodies and single-site immunometric assays wherein the antibody is labeled; and the like.

All examples were carried out using standard techniques, which are well known and routine to those of skill in the art, except where otherwise described in detail. Routine molecular biology techniques of the following examples can be carried out as described in standard laboratory manuals, such as Sambrook et al., *Molecular Cloning: A Laboratory Manual,* 2nd Ed., Cold Spring Harbor Laboratory Press, Cold Spring Harbor, N.Y. (1989).

Copending applications entitled "Haptens of Aripiprazole", U.S. Provisional Patent Appl. No. 61/691,450, filed Aug. 21, 2012, and US 20140163206, filed Aug. 20, 2013), "Haptens of Olanzapine", U.S. Provisional Patent Appl. No. 61/691,454, filed Aug. 21, 2012, and US 20140213766, filed Aug. 20, 2013), "Haptens of Paliperidone", U.S. Provisional Patent Appl. No. 61/691,459, filed Aug. 21, 2012, and US 20140213767, filed Aug. 20, 2013), "Haptens of Quetiapine", U.S. Provisional Patent Appl. No. 61/691,462, filed Aug. 21, 2012, and US 20140221616, filed Aug. 20, 2013), "Haptens of Risperidone and Paliperidone", U.S. Provisional Patent Appl. No. 61/691,469, filed Aug. 21, 2012, and US 20140155585, Aug. 20, 2013), "Antibodies to Aripiprazole Haptens and Use Thereof", U.S. Provisional Patent Appl. No. 61/691,544, filed Aug. 21, 2012, and US 20140057299, filed Aug. 20, 2013), "Antibodies to Olanzapine Haptens and Use Thereof", U.S. Provisional Patent Appl. No. 61/691,572, filed Aug. 21, 2012, US 20140057303, filed Aug. 20, 2013), "Antibodies to Paliperidone Haptens and Use Thereof", U.S. Provisional Patent Appl. No. 61/691,634, filed Aug. 21, 2012, and US 20140057297, filed Aug. 20, 2013), "Antibodies to Quetiapine Haptens and Use Thereof", U.S. Provisional Patent Appl. No. 61/691,598, filed Aug. 21, 2012, and US 20140057305, filed Aug. 20, 2013), "Antibodies to Risperidone Haptens and Use Thereof", U.S. Provisional Patent Appl. No. 61/691,615, filed Aug. 21, 2012, and US 20140057301, filed Aug. 20, 2013), "Antibodies to Aripiprazole and Use Thereof", U.S. Provisional Patent Appl. No. 61/691,522, filed Aug. 21, 2012, and US 20140057300, filed Aug. 20, 2013), "Antibodies to Paliperidone and Use Thereof", U.S. Provisional Patent Appl. No. 61/691,692, filed Aug. 21, 2012, and US 20140057298, filed Aug. 20, 2013), "Antibodies to Quetiapine and Use Thereof", U.S. Provisional Patent Appl. No. 61/691,659, filed Aug. 21, 2012, and US 20140057306, filed Aug. 20, 2013), "Antibodies to Risperidone and Use Thereof", U.S. Provisional Patent Appl. No. 61/691,675, filed Aug. 21, 2012, and US 20140057302, filed Aug. 20, 2013), and "Antibodies to Risperidone and Use Thereof", U.S. Provisional Patent Appl. No. 61/790,880, filed Mar. 15, 2013, and US 20140057302, filed Aug. 20, 2013) are all incorporated herein by reference in their entireties.

EXAMPLE 1

Antibodies to Aripiprazole

Antibody 17.3 Clone 3D7

The hybridoma designated 17.3 clone 3D7 secretes a monoclonal antibody (mAb) specific for aripiprazole. The antibody is designated 17.3 clone 3D7. The nucleotide sequence of mAb 17.3 clone 3D7's light chain variable region ($V_L$) is designated SEQ ID NO:41 and that of the heavy chain variable region ($V_H$) is designated SEQ ID NO:42. Within mAb 17.3 clone 3D7's $V_L$, nucleotides 136-165 of SEQ ID NO:41 represent the first complementarity determining region (CDR1); nucleotides 211-231 of SEQ ID NO:41 represent the second complementarity determining region (CDR2); and nucleotides 328-354 of SEQ ID NO:41 represent the third complementarity determining region (CDR3). Within mAb 17.3 clone 3D7's $V_H$, nucleotides 133-162 of SEQ ID NO:42 represent the first complementarity determining region (CDR1); nucleotides 205-255 of SEQ ID NO:42 represent the second complementarity determining region (CDR2); and nucleotides 352-375 of SEQ ID NO:42 represent the third complementarity determining region (CDR3).

The corresponding predicted amino acid sequences of mAb 17.3 clone 3D7's variable chain regions were also determined, and are designated SEQ ID NO:43 (light chain) and SEQ ID NO:44 (heavy chain). Within mAb 17.3 clone 3D7's $V_L$, amino acid residues 46-55 of SEQ ID NO:43 represent the first complementarity determining region (CDR1); amino acid residues 71-77 of SEQ ID NO:43 represent the second complementarity determining region (CDR2); and amino acid residues 110-118 of SEQ ID NO:43 represent the third complementarity determining region (CDR3). Within mAb 17.3 clone 3D7's $V_H$, amino acid residues 45-54 of SEQ ID NO:44 represent the first complementarity determining region (CDR1); amino acid residues 69-85 of SEQ ID NO:44 represent the second complementarity determining region (CDR2); and amino acid residues 118-125 of SEQ ID NO:44 represent the third complementarity determining region (CDR3).

Antibody 17.3 Clone 5C7 (First)

The hybridoma designated 17.3 clone 5C7 (first) secretes a monoclonal antibody (mAb) specific for aripiprazole. The antibody is designated 17.3 clone 5C7 (first). The nucleotide sequence of mAb 17.3 clone 5C7 (first)'s light chain variable region ($V_L$) is designated SEQ ID NO:45 and that of the heavy chain variable region ($V_H$) is designated SEQ ID NO:46. Within mAb 17.3 clone 5C7 (first)'s $V_L$, nucleotides 130-162 of SEQ ID NO:45 represent the first complementarity determining region (CDR1); nucleotides 208-228 of SEQ ID NO:45 represent the second complementarity determining region (CDR2); and nucleotides 325-351 of SEQ ID NO:45 represent the third complementarity determining region (CDR3). Within mAb 17.3 clone 5C7 (first)'s $V_H$, nucleotides 133-162 of SEQ ID NO:46 represent the first complementarity determining region (CDR1); nucleotides 205-255 of SEQ ID NO:46 represent the second complementarity determining region (CDR2); and nucleotides 352-378 of SEQ ID NO:46 represent the third complementarity determining region (CDR3).

The corresponding predicted amino acid sequences of mAb 17.3 clone 5C7 (first)'s variable chain regions were also determined, and are designated SEQ ID NO:47 (light chain) and SEQ ID NO:48 (heavy chain). Within mAb 17.3 clone 5C7 (first)'s $V_L$, amino acid residues 44-54 of SEQ ID NO:47 represent the first complementarity determining region (CDR1); amino acid residues 70-76 of SEQ ID NO:47 represent the second complementarity determining region (CDR2); and amino acid residues 109-117 of SEQ ID NO:47 represent the third complementarity determining region (CDR3). Within mAb 17.3 clone 5C7 (first)'s $V_H$, amino acid residues 45-54 of SEQ ID NO:48 represent the first complementarity determining region (CDR1); amino acid residues 69-85 of SEQ ID NO:48 represent the second complementarity determining region (CDR2); and amino acid residues 118-126 of SEQ ID NO:48 represent the third complementarity determining region (CDR3).

Antibody 17.3 Clone 5C7 (Second)

The hybridoma designated 17.3 clone 5C7 (second) secretes a monoclonal antibody (mAb) specific for aripiprazole. The antibody is designated 17.3 clone 5C7 (second). The nucleotide sequence of mAb 17.3 clone 5C7 (second)'s light chain variable region ($V_L$) is designated SEQ ID NO:49 and that of the heavy chain variable region ($V_H$) is designated SEQ ID NO:50. Within mAb 17.3 clone 5C7 (second)'s $V_L$, nucleotides 130-174 of SEQ ID NO:49 represent the first complementarity determining region (CDR1); nucleotides 220-240 of SEQ ID NO:49 represent the second complementarity determining region (CDR2); and nucleotides 337-363 of SEQ ID NO:49 represent the third complementarity determining region (CDR3). Within mAb 17.3 clone 5C7 (second)'s $V_H$, nucleotides 133-162 of SEQ ID NO:50 represent the first complementarity determining region (CDR1); nucleotides 205-255 of SEQ ID NO:50 represent the second complementarity determining region (CDR2); and nucleotides 352-390 of SEQ ID NO:50 represent the third complementarity determining region (CDR3).

The corresponding predicted amino acid sequences of mAb 17.3 clone 5C7 (second)'s variable chain regions were also determined, and are designated SEQ ID NO:51 (light chain) and SEQ ID NO:52 (heavy chain). Within mAb 17.3 clone 5C7 (second)'s $V_L$, amino acid residues 44-58 of SEQ ID NO:51 represent the first complementarity determining region (CDR1); amino acid residues 74-80 of SEQ ID NO:51 represent the second complementarity determining region (CDR2); and amino acid residues 113-121 of SEQ ID NO:51 represent the third complementarity determining region (CDR3). Within mAb 17.3 clone 5C7 (second)'s $V_H$, amino acid residues 45-54 of SEQ ID NO:52 represent the first complementarity determining region (CDR1); amino acid residues 69-85 of SEQ ID NO:52 represent the second complementarity determining region (CDR2); and amino acid residues 118-130 of SEQ ID NO:52 represent the third complementarity determining region (CDR3).

Antibody 17.3 Clone 5C7 (Third)

The hybridoma designated 17.3 clone 5C7 (third) secretes a monoclonal antibody (mAb) specific for aripiprazole. The antibody is designated 17.3 clone 5C7 (third). The nucleotide sequence of mAb 17.3 clone 5C7 (third)'s light chain variable region ($V_L$) is designated SEQ ID NO:53 and that of the heavy chain variable region ($V_H$) is designated SEQ ID NO:54. Within mAb 17.3 clone 5C7 (third)'s $V_L$, nucleotides 130-162 of SEQ ID NO:53 represent the first complementarity determining region (CDR1); nucleotides 208-228 of SEQ ID NO:53 represent the second complementarity determining region (CDR2); and nucleotides 325-351 of SEQ ID NO:53 represent the third complementarity determining region (CDR3). Within mAb 17.3 clone 5C7 (third)'s $V_H$, nucleotides 133-162 of SEQ ID NO:54 represent the first complementarity determining region (CDR1); nucleotides 205-255 of SEQ ID NO:54 represent the second complementarity determining region (CDR2); and nucleotides 352-366 of SEQ ID NO:54 represent the third complementarity determining region (CDR3).

The corresponding predicted amino acid sequences of mAb 17.3 clone 5C7 (third)'s variable chain regions were also determined, and are designated SEQ ID NO:55 (light chain) and SEQ ID NO:56 (heavy chain). Within mAb 17.3 clone 5C7 (third)'s $V_L$, amino acid residues 44-54 of SEQ ID NO:55 represent the first complementarity determining region (CDR1); amino acid residues 70-76 of SEQ ID NO:55 represent the second complementarity determining region (CDR2); and amino acid residues 109-117 of SEQ ID NO:55 represent the third complementarity determining region (CDR3). Within mAb 17.3 clone 5C7 (third)'s $V_H$, amino acid residues 45-54 of SEQ ID NO:56 represent the first complementarity determining region (CDR1); amino acid residues 69-85 of SEQ ID NO:56 represent the second complementarity determining region (CDR2); and amino acid residues 118-122 of SEQ ID NO:56 represent the third complementarity determining region (CDR3).

EXAMPLE 2

Antibodies to Olanzapine

Antibody 11.1 Clone 35

The hybridoma designated 11.1 clone 35 secretes a monoclonal antibody (mAb) specific for olanzapine. The antibody is designated 11.1 clone 35. The nucleotide sequence of mAb 11.1 clone 35's light chain variable region ($V_L$) is designated SEQ ID NO:9 and that of the heavy chain variable region ($V_H$) is designated SEQ ID NO:10. Within mAb 11.1 clone 35's $V_L$, nucleotides 130-162 of SEQ ID NO:9 represent the first complementarity determining region (CDR1); nucleotides 208-228 of SEQ ID NO:9 represent the second complementarity determining region (CDR2); and nucleotides 325-351 of SEQ ID NO:9 represent the third complementarity determining region (CDR3). Within mAb 11.1 clone 35's $V_H$, nucleotides 133-162 of SEQ ID NO:10 represent the first complementarity determining region (CDR1); nucleotides 205-255 of SEQ ID NO:10 represent the second complementarity determining region (CDR2); and nucleotides 352-366 of SEQ ID NO:10 represent the third complementarity determining region (CDR3).

The corresponding predicted amino acid sequences of mAb 11.1 clone 35's variable chain regions were also determined, and are designated SEQ ID NO:11 (light chain) and SEQ ID NO:12 (heavy chain). Within mAb 11.1 clone 35's $V_L$, amino acid residues 44-54 of SEQ ID NO:11 represent the first complementarity determining region (CDR1); amino acid residues 70-76 of SEQ ID NO:11 represent the second complementarity determining region (CDR2); and amino acid residues 109-117 of SEQ ID NO:11 represent the third complementarity determining region (CDR3). Within mAb 11.1 clone 35's $V_H$, amino acid residues 45-54 of SEQ ID NO:12 represent the first complementarity determining region (CDR1); amino acid residues 69-85 of SEQ ID NO:12 represent the second complementarity determining region (CDR2); and amino acid residues 118-122 of SEQ ID NO:12 represent the third complementarity determining region (CDR3).

Antibody 11.1 Clone 61

The hybridoma designated 11.1 clone 61 secretes a monoclonal antibody (mAb) specific for olanzapine. The antibody is designated 11.1 clone 61. The nucleotide sequence of mAb 11.1 clone 61's light chain variable region ($V_L$) is designated SEQ ID NO:13 and that of the heavy chain variable region ($V_H$) is designated SEQ ID NO:14. Within mAb 11.1 clone 61's $V_L$, nucleotides 130-162 of SEQ ID NO:13 represent the first complementarity determining region (CDR1); nucleotides 208-228 of SEQ ID NO:13 represent the second complementarity determining region (CDR2); and nucleotides 325-351 of SEQ ID NO:13 represent the third complementarity determining region (CDR3). Within mAb 11.1 clone 61's $V_H$, nucleotides 133-162 of SEQ ID NO:14 represent the first complementarity determining region (CDR1); nucleotides 205-255 of SEQ ID NO:14 represent the second complementarity determining region (CDR2); and nucleotides 352-366 of SEQ ID NO:14 represent the third complementarity determining region (CDR3).

The corresponding predicted amino acid sequences of mAb 11.1 clone 61's variable chain regions were also determined, and are designated SEQ ID NO:15 (light chain) and SEQ ID NO:16 (heavy chain). Within mAb 11.1 clone 61's $V_L$, amino acid residues 44-54 of SEQ ID NO:15 represent the first complementarity determining region (CDR1); amino acid residues 70-76 of SEQ ID NO:15 represent the second complementarity determining region (CDR2); and amino acid residues 109-117 of SEQ ID NO:15 represent the third complementarity determining region (CDR3). Within mAb 11.1 clone 61's $V_H$, amino acid residues 45-54 of SEQ ID NO:16 represent the first complementarity determining region (CDR1); amino acid residues 69-85 of SEQ ID NO:16 represent the second complementarity determining region (CDR2); and amino acid residues 118-122 of SEQ ID NO:16 represent the third complementarity determining region (CDR3).

Antibody 15.5 Clone 3F11 (First)

The hybridoma designated 15.5 clone 3F11 (first) secretes a monoclonal antibody (mAb) specific for olanzapine. The antibody is designated 15.5 clone 3F11 (first). The nucleotide sequence of mAb 15.5 clone 3F11 (first)'s light chain variable region ($V_L$) is designated SEQ ID NO:29 and that of the heavy chain variable region ($V_H$) is designated SEQ ID NO:30. Within mAb 15.5 clone 3F11 (first)'s $V_L$, nucleotides 130-162 of SEQ ID NO:29 represent the first complementarity determining region (CDR1); nucleotides 208-228 of SEQ ID NO:29 represent the second complementarity determining region (CDR2); and nucleotides 325-351 of SEQ ID NO:29 represent the third complementarity determining region (CDR3). Within mAb 15.5 clone 3F11 (first)'s $V_H$, nucleotides 130-162 of SEQ ID NO:30 represent the first complementarity determining region (CDR1); nucleotides 205-252 of SEQ ID NO:30 represent the second complementarity determining region (CDR2); and nucleotides 355-381 of SEQ ID NO:30 represent the third complementarity determining region (CDR3).

The corresponding predicted amino acid sequences of mAb 15.5 clone 3F11 (first)'s variable chain regions were also determined, and are designated SEQ ID NO:31 (light chain) and SEQ ID NO:32 (heavy chain). Within mAb 15.5 clone 3F11 (first)'s $V_L$, amino acid residues 44-54 of SEQ ID NO:31 represent the first complementarity determining region (CDR1); amino acid residues 70-76 of SEQ ID NO:31 represent the second complementarity determining region (CDR2); and amino acid residues 109-117 of SEQ ID NO:31 represent the third complementarity determining region (CDR3). Within mAb 15.5 clone 3F11 (first)'s $V_H$, amino acid residues 44-54 of SEQ ID NO:32 represent the first complementarity determining region (CDR1); amino acid residues 69-84 of SEQ ID NO:32 represent the second complementarity determining region (CDR2); and amino acid residues 119-127 of SEQ ID NO:32 represent the third complementarity determining region (CDR3).

Antibody 15.5 Clone 3F11 (Second)

The hybridoma designated 15.5 clone 3F11 (second) secretes a monoclonal antibody (mAb) specific for olanzapine. The antibody is designated 15.5 clone 3F11 (second). The nucleotide sequence of mAb 15.5 clone 3F11 (second)'s light chain variable region ($V_L$) is designated SEQ ID NO:33 and that of the heavy chain variable region ($V_H$) is designated SEQ ID NO:34. Within mAb 15.5 clone 3F11 (second)'s $V_L$, nucleotides 130-162 of SEQ ID NO:33 represent the first complementarity determining region (CDR1); nucleotides 208-228 of SEQ ID NO:33 represent the second complementarity determining region (CDR2); and nucleotides 325-351 of SEQ ID NO:33 represent the third complementarity determining region (CDR3). Within mAb 15.5 clone 3F11 (second)'s $V_H$, nucleotides 133-162 of SEQ ID NO:34 represent the first complementarity determining region (CDR1); nucleotides 205-261 of SEQ ID NO:34 represent the second complementarity determining region (CDR2); and nucleotides 358-381 of SEQ ID NO:34 represent the third complementarity determining region (CDR3).

The corresponding predicted amino acid sequences of mAb 15.5 clone 3F11 (second)'s variable chain regions were also determined, and are designated SEQ ID NO:35 (light chain) and SEQ ID NO:36 (heavy chain). Within mAb 15.5 clone 3F11 (second)'s $V_L$, amino acid residues 44-54 of SEQ ID NO:35 represent the first complementarity determining region (CDR1); amino acid residues 70-76 of SEQ ID NO:35 represent the second complementarity determining region (CDR2); and amino acid residues 109-117 of SEQ ID NO:35 represent the third complementarity determining region (CDR3). Within mAb 15.5 clone 3F11 (second)'s $V_H$, amino acid residues 45-54 of SEQ ID NO:36 represent the first complementarity determining region (CDR1); amino acid residues 69-87 of SEQ ID NO:36 represent the second complementarity determining region (CDR2); and amino acid residues 120-127 of SEQ ID NO:36 represent the third complementarity determining region (CDR3).

Antibody 15.5 Sub-Clone 4G9-1

The hybridoma designated 15.5 sub-clone 4G9-1 secretes a monoclonal antibody (mAb) specific for olanzapine. The antibody is designated 15.5 sub-clone 4G9-1. The nucleotide sequence of mAb 15.5 sub-clone 4G9-1's light chain variable region ($V_L$) is designated SEQ ID NO:37 and that of the heavy chain variable region ($V_H$) is designated SEQ ID NO:38. Within mAb 15.5 sub-clone 4G9-1's $V_L$, nucleotides 130-162 of SEQ ID NO:37 represent the first complementarity determining region (CDR1); nucleotides 208-228 of SEQ ID NO:37 represent the second complementarity determining region (CDR2); and nucleotides 325-351 of SEQ ID NO:37 represent the third complementarity determining region (CDR3). Within mAb 15.5 sub-clone 4G9-1's $V_H$, nucleotides 130-162 of SEQ ID NO:38 represent the first complementarity determining region (CDR1); nucleotides 205-252 of SEQ ID NO:38 represent the second complementarity determining region (CDR2); and nucleotides 358-381 of SEQ ID NO:38 represent the third complementarity determining region (CDR3).

The corresponding predicted amino acid sequences of mAb 15.5 sub-clone 4G9-1's variable chain regions were also determined, and are designated SEQ ID NO:39 (light chain) and SEQ ID NO:40 (heavy chain). Within mAb 15.5 sub-clone 4G9-1's $V_L$, amino acid residues 44-54 of SEQ ID NO:39 represent the first complementarity determining region (CDR1); amino acid residues 70-76 of SEQ ID NO:39 represent the second complementarity determining region (CDR2); and amino acid residues 109-117 of SEQ ID NO:39 represent the third complementarity determining region (CDR3). Within mAb 15.5 sub-clone 4G9-1's $V_H$, amino acid residues 44-54 of SEQ ID NO:40 represent the first complementarity determining region (CDR1); amino acid residues 69-84 of SEQ ID NO:40 represent the second complementarity determining region (CDR2); and amino acid residues 120-127 of SEQ ID NO:40 represent the third complementarity determining region (CDR3).

EXAMPLE 3

Antibodies to Quetiapine

Antibody 13.2 Sub-Clone 89-3 (First)

The hybridoma designated 13.2 sub-clone 89-3 (first) secretes a monoclonal antibody (mAb) specific for quetiapine. The antibody is designated 13.2 sub-clone 89-3 (first). The nucleotide sequence of mAb 13.2 sub-clone 89-3 (first)'s light chain variable region ($V_L$) is designated SEQ ID NO:17 and that of the heavy chain variable region ($V_H$) is designated SEQ ID NO:18. Within mAb 13.2 sub-clone 89-3 (first)'s $V_L$, nucleotides 127-174 of SEQ ID NO:17 represent the first complementarity determining region (CDR1); nucleotides 220-240 of SEQ ID NO:17 represent the second complementarity determining region (CDR2); and nucleotides 337-363 of SEQ ID NO:17 represent the third complementarity determining region (CDR3). Within mAb 13.2 sub-clone 89-3 (first)'s $V_H$, nucleotides 133-162 of SEQ ID NO:18 represent the first complementarity determining region (CDR1); nucleotides 205-255 of SEQ ID NO:18 represent the second complementarity determining region (CDR2); and nucleotides 352-387 of SEQ ID NO:18 represent the third complementarity determining region (CDR3).

The corresponding predicted amino acid sequences of mAb 13.2 sub-clone 89-3 (first)'s variable chain regions were also determined, and are designated SEQ ID NO:19 (light chain) and SEQ ID NO:20 (heavy chain). Within mAb 13.2 sub-clone 89-3 (first)'s $V_L$, amino acid residues 43-58 of SEQ ID NO:19 represent the first complementarity determining region (CDR1); amino acid residues 74-80 of SEQ ID NO:19 represent the second complementarity determining region (CDR2); and amino acid residues 113-121 of SEQ ID NO:19 represent the third complementarity determining region (CDR3). Within mAb 13.2 sub-clone 89-3 (first)'s $V_H$, amino acid residues 45-54 of SEQ ID NO:20 represent the first complementarity determining region (CDR1); amino acid residues 69-85 of SEQ ID NO:20 represent the second complementarity determining region (CDR2); and amino acid residues 118-129 of SEQ ID NO:20 represent the third complementarity determining region (CDR3).

Antibody 13.2 Sub-Clone 89-3 (Second)

The hybridoma designated 13.2 sub-clone 89-3 (second) secretes a monoclonal antibody (mAb) specific for quetiapine. The antibody is designated 13.2 sub-clone 89-3 (second). The nucleotide sequence of mAb 13.2 sub-clone 89-3 (second)'s light chain variable region ($V_L$) is designated SEQ ID NO:21 and that of the heavy chain variable region ($V_H$) is designated SEQ ID NO:22. Within mAb 13.2 sub-clone 89-3 (second)'s $V_L$, nucleotides 127-174 of SEQ ID NO:21 represent the first complementarity determining region (CDR1); nucleotides 220-240 of SEQ ID NO:21 represent the second complementarity determining region (CDR2); and nucleotides 337-363 of SEQ ID NO:21 represent the third complementarity determining region (CDR3). Within mAb 13.2 sub-clone 89-3 (second)'s $V_H$, nucleotides 133-162 of SEQ ID NO:22 represent the first complementarity determining region (CDR1); nucleotides 205-255 of SEQ ID NO:22 represent the second complementarity determining region (CDR2); and nucleotides 367-387 of SEQ ID NO:22 represent the third complementarity determining region (CDR3).

The corresponding predicted amino acid sequences of mAb 13.2 sub-clone 89-3 (second)'s variable chain regions were also determined, and are designated SEQ ID NO:23 (light chain) and SEQ ID NO:24 (heavy chain). Within mAb 13.2 sub-clone 89-3 (second)'s $V_L$, amino acid residues 43-58 of SEQ ID NO:23 represent the first complementarity determining region (CDR1); amino acid residues 74-80 of SEQ ID NO:23 represent the second complementarity determining region (CDR2); and amino acid residues 113-121 of SEQ ID NO:23 represent the third complementarity determining region (CDR3). Within mAb 13.2 sub-clone 89-3 (second)'s $V_H$, amino acid residues 45-54 of SEQ ID NO:24 represent the first complementarity determining region (CDR1); amino acid residues 69-85 of SEQ ID NO:24 represent the second complementarity determining region (CDR2); and amino acid residues 123-129 of SEQ ID NO:24 represent the third complementarity determining region (CDR3).

Antibody 13.2 Sub-Clone 89-5

The hybridoma designated 13.2 sub-clone 89-5 secretes a monoclonal antibody (mAb) specific for quetiapine. The antibody is designated 13.2 sub-clone 89-5. The nucleotide sequence of mAb 13.2 sub-clone 89-5's light chain variable region ($V_L$) is designated SEQ ID NO:25 and that of the heavy chain variable region ($V_H$) is designated SEQ ID NO:26. Within mAb 13.2 sub-clone 89-5's $V_L$, nucleotides 127-174 of SEQ ID NO:25 represent the first complementarity determining region (CDR1); nucleotides 220-240 of SEQ ID NO:25 represent the second complementarity determining region (CDR2); and nucleotides 337-363 of SEQ ID NO:25 represent the third complementarity determining region (CDR3). Within mAb 13.2 sub-clone 89-5's $V_H$, nucleotides 133-162 of SEQ ID NO:26 represent the first complementarity determining region (CDR1); nucleotides 205-255 of SEQ ID NO:26 represent the second complementarity determining region (CDR2); and nucleotides 367-387 of SEQ ID NO:26 represent the third complementarity determining region (CDR3).

The corresponding predicted amino acid sequences of mAb 13.2 sub-clone 89-5's variable chain regions were also determined, and are designated SEQ ID NO:27 (light chain) and SEQ ID NO:28 (heavy chain). Within mAb 13.2 sub-clone 89-5's $V_L$, amino acid residues 43-58 of SEQ ID NO:27 represent the first complementarity determining region (CDR1); amino acid residues 74-80 of SEQ ID NO:27 represent the second complementarity determining region (CDR2); and amino acid residues 113-121 of SEQ ID NO:27 represent the third complementarity determining region (CDR3). Within mAb 13.2 sub-clone 89-5's $V_H$, amino acid residues 45-54 of SEQ ID NO:28 represent the first complementarity determining region (CDR1); amino acid residues 69-85 of SEQ ID NO:28 represent the second complementarity determining region (CDR2); and amino acid residues 123-129 of SEQ ID NO:28 represent the third complementarity determining region (CDR3).

EXAMPLE 4

Antibodies to Risperidone/Paliperidone

Antibody 5_9

The hybridoma designated 5_9 secretes a monoclonal antibody (mAb) specific for risperidone (and its metabolite paliperidone). The antibody is designated 5-9. The nucleotide sequence of mAb 5-9's light chain variable region ($V_L$) is designated SEQ ID NO:1 and that of the heavy chain variable region ($V_H$) is designated SEQ ID NO:2. Within mAb 5-9's $V_L$, nucleotides 130-180 of SEQ ID NO:1 represent the first complementarity determining region (CDR1); nucleotides 226-246 of SEQ ID NO:1 represent the second complementarity determining region (CDR2); and nucleotides 343-369 of SEQ ID NO:1 represent the third complementarity determining region (CDR3). Within mAb 5-9's $V_H$, nucleotides 133-162 of SEQ ID NO:2 represent the first complementarity determining region (CDR1); nucleotides 205-255 of SEQ ID NO:2 represent the second complementarity determining region (CDR2); and nucleotides 352-366 of SEQ ID NO:2 represent the third complementarity determining region (CDR3).

The corresponding predicted amino acid sequences of mAb 5-9's variable chain regions were also determined, and are designated SEQ ID NO:3 (light chain) and SEQ ID NO:4 (heavy chain). Within mAb 5-9's $V_L$, amino acid residues 44-60 of SEQ ID NO:3 represent the first complementarity determining region (CDR1); amino acid residues 76-82 of SEQ ID NO:3 represent the second complementarity determining region (CDR2); and amino acid residues 115-123 of SEQ ID NO:3 represent the third complementarity determining region (CDR3). Within mAb 5-9's $V_H$, amino acid residues 45-54 of SEQ ID NO:4 represent the first complementarity determining region (CDR1); amino acid residues 69-85 of SEQ ID NO:4 represent the second complementarity determining region (CDR2); and amino acid residues 118-122 of SEQ ID NO:4 represent the third complementarity determining region (CDR3).

Antibody 5_5

The hybridoma designated 5_5 secretes a monoclonal antibody (mAb) specific for risperidone (and its metabolite paliperidone). The antibody is designated 5-5. The nucleotide sequence of mAb 5-5's light chain variable region ($V_L$) is designated SEQ ID NO:5 and that of the heavy chain variable region ($V_H$) is designated SEQ ID NO:6. Within mAb 5-5's $V_L$, nucleotides 130-180 of SEQ ID NO:5 represent the first complementarity determining region (CDR1); nucleotides 226-246 of SEQ ID NO:5 represent the second complementarity determining region (CDR2); and nucleotides 343-369 of SEQ ID NO:5 represent the third complementarity determining region (CDR3). Within mAb 5-9's $V_H$, nucleotides 133-162 of SEQ ID NO:6 represent the first complementarity determining region (CDR1); nucleotides 205-255 of SEQ ID NO:6 represent the second complementarity determining region (CDR2); and nucleotides 352-366 of SEQ ID NO:6 represent the third complementarity determining region (CDR3).

The corresponding predicted amino acid sequences of mAb 5-5's variable chain regions were also determined, and are designated SEQ ID NO:7 (light chain) and SEQ ID NO:8 (heavy chain). Within mAb 5-5's $V_L$, amino acid residues 44-60 of SEQ ID NO:7 represent the first complementarity determining region (CDR1); amino acid residues 76-82 of SEQ ID NO:7 represent the second complementarity determining region (CDR2); and amino acid residues 115-123 of SEQ ID NO:7 represent the third complementarity determining region (CDR3). Within mAb 5-5's $V_H$, amino acid residues 45-54 of SEQ ID NO:8 represent the first complementarity determining region (CDR1); amino acid residues 69-85 of SEQ ID NO:8 represent the second complementarity determining region (CDR2); and amino acid residues 118-122 of SEQ ID NO:8 represent the third complementarity determining region (CDR3).

EXAMPLE 5

Competitive Immunoassays for Olanzapine and Multiplex Competitive Immunoassay for Aripiprazole, Olanzapine, Quetiapine, and Risperidone/Paliperidone Following a series of immunizations with olanzapine immunogens, mouse tail bleeds were tested for reactivity using an ELISA. Hybridoma supernatants were also tested, and the ELISA data shown in Tables 1 and 2 below shows reactivity of several hybridomas (fusion partner was NSO cells).

TABLE 1

| | | | | | | Plate 2 | | | | | | | |
|---|---|---|---|---|---|---|---|---|---|---|---|---|---|
| Dilution | 1 | 2 | 3 | 4 | 5 | 6 | 7 | 8 | 9 | 10 | 11 | 12 | |
| 1/400 | 25 | 26 | 27 | 28 | 29 | 30 | 31 | 21 | 33 | 34 | 35 | 36 | Ag = Bt-Compound #11 |
| 1/1200 | | | | | | | | | | | | | |
| 1/3600 | | | | | | | | | | | | | |
| 1/10800 | | | | | | | | | | | | | |

TABLE 1-continued

| | Plate 2 | | | | | | | | | | | | |
|---|---|---|---|---|---|---|---|---|---|---|---|---|
| Dilution | 1 | 2 | 3 | 4 | 5 | 6 | 7 | 8 | 9 | 10 | 11 | 12 |
| 1/400 | 37 | 38 | 39 | 40 | 41 | 42 | 43 | 44 | 45 | 46 | 47 | 48 |
| 1/1200 | | | | | | | | | | | | |
| 1/3600 | | | | | | | | | | | | |
| 1/10800 | | | | | | | | | | | | |
| 1/400 | 0.0136 | 0.0432 | 0.131 | 0.0654 | 0.4092 | 0.039 | 0.016 | 0.1408 | 0.0712 | 1.4864 | 2.0086 | 0.0861 |
| 1/1200 | 0.0113 | 0.0194 | 0.0477 | 0.0291 | 0.1293 | 0.031 | 0.012 | 0.0374 | 0.0126 | 0.4411 | 0.8874 | 0.0362 |
| 1/3600 | 0.0092 | 0.0118 | 0.0233 | 0.0153 | 0.0462 | 0.013 | 0.009 | 0.0314 | 0.0275 | 0.2073 | 0.3555 | 0.0217 |
| 1/10800 | 0.0105 | 0.0111 | 0.0159 | 0.0107 | 0.0224 | 0.012 | 0.009 | 0.0172 | 0.0168 | 0.0972 | 0.147 | 0.0141 |
| 1/400 | 0.0333 | 0.1512 | 1.1412 | 1.0762 | 0.3042 | 0.04 | 0.449 | 0.1619 | 1.8038 | 0.0933 | 0.7666 | 1.258 |
| 1/1200 | 0.0144 | 0.055 | 0.4575 | 0.3223 | 0.0907 | 0.016 | 0.144 | 0.0402 | 0.1536 | 0.0288 | 0.2956 | 0.4374 |
| 1/3600 | 0.008 | 0.0333 | 0.2036 | 1.1077 | 0.0361 | 0.011 | 0.051 | 0.0206 | 0.708 | 0.0165 | 0.1212 | 0.2072 |
| 1/10800 | 0.0109 | 0.0181 | 0.0885 | 0.0581 | 0.027 | 0.01 | 0.045 | 0.0217 | 0.5338 | 0.0132 | 0.0585 | 0.0954 |

Ag = Bt-Compound #11

TABLE 2

| | Plate 3 | | | | | | | | | | | | |
|---|---|---|---|---|---|---|---|---|---|---|---|---|
| Dilution | 1 | 2 | 3 | 4 | 5 | 6 | 7 | 8 | 9 | 10 | 11 | 12 |
| 100 | 152 | 104 | 283 | 258 | 3A3 | YES | 3F11 | 489 | 5O11 | 6G2 | 813 | Empty |
| 100 | | | | | | | | | | | | |
| 300 | | | | | | | | | | | | |
| 300 | | | | | | | | | | | | |
| 900 | | | | | | | | | | | | |
| 900 | | | | | | | | | | | | |
| 2700 | | | | | | | | | | | | |
| 2700 | | | | | | | | | | | | |
| 100 | 0.0628 | 0.5834 | 2.9908 | 1.9083 | 0.7869 | 2.7664 | 2.295 | 1.027 | 0.1174 | 0.8223 | 0.041 | 0 |
| 100 | 0.0527 | 0.428 | 2.7862 | 1.3797 | 0.6634 | 2.3072 | 2.0249 | 0.934 | 0.1115 | 0.7692 | 0.0385 | 0.0057 |
| 300 | 0.0202 | 0.1452 | 1.3705 | 6.5961 | 0.2337 | 1.3963 | 0.8952 | 0.2999 | 0.0375 | 0.2486 | 0.0177 | 0.0031 |
| 300 | 0.0208 | 0.1468 | 1.3166 | 0.5235 | 0.2173 | 1.1112 | 0.9114 | 0.3116 | 0.0408 | 0.2483 | 0.0174 | 0.0052 |
| 900 | 0.0132 | 0.0242 | 0.4925 | 0.1967 | 0.0849 | 0.4472 | 0.2986 | 0.0896 | 0.0179 | 0.0851 | 0.012 | 0.0039 |
| 900 | 0.0148 | 0.0654 | 0.4651 | 0.1731 | 0.0839 | 0.4471 | 0.3498 | 0.0951 | 0.016 | 0.0853 | 0.0128 | 0.0066 |
| 2700 | 0.0109 | 0.4259 | 0.1877 | 0.0713 | 0.6334 | 0.1709 | 0.1381 | 0.0352 | 0.0111 | 0.036 | 0.0094 | 0.0041 |
| 2700 | 0.0122 | 0.028 | 0.1835 | 0.0903 | 0.0404 | 0.1924 | 0.1502 | 0.0408 | 0.0113 | 0.0325 | 0.0084 | 0.005 |

Figure 2:
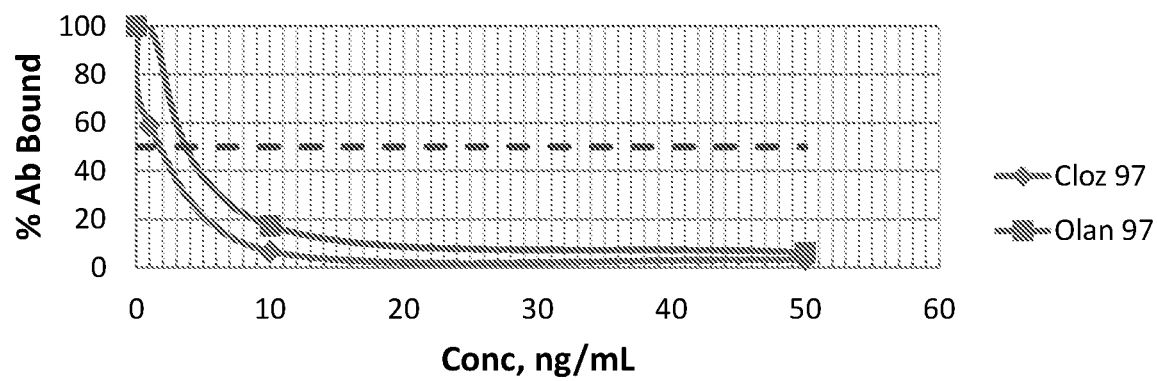
Figure 3:
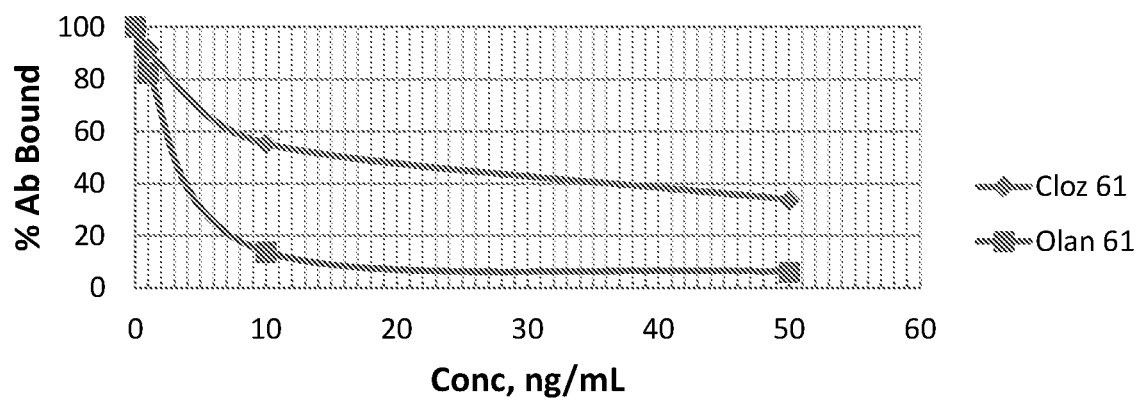

Supernatant was then tested by competition ELISA to determine if the signals were specific to olanzapine. FIGS. 1-3 show the results from three representative hybridomas resulting from mouse fusion 11.1. Data shows specific reactivity to olanzapine with varied reactivity to clozapine.

Figure 4:
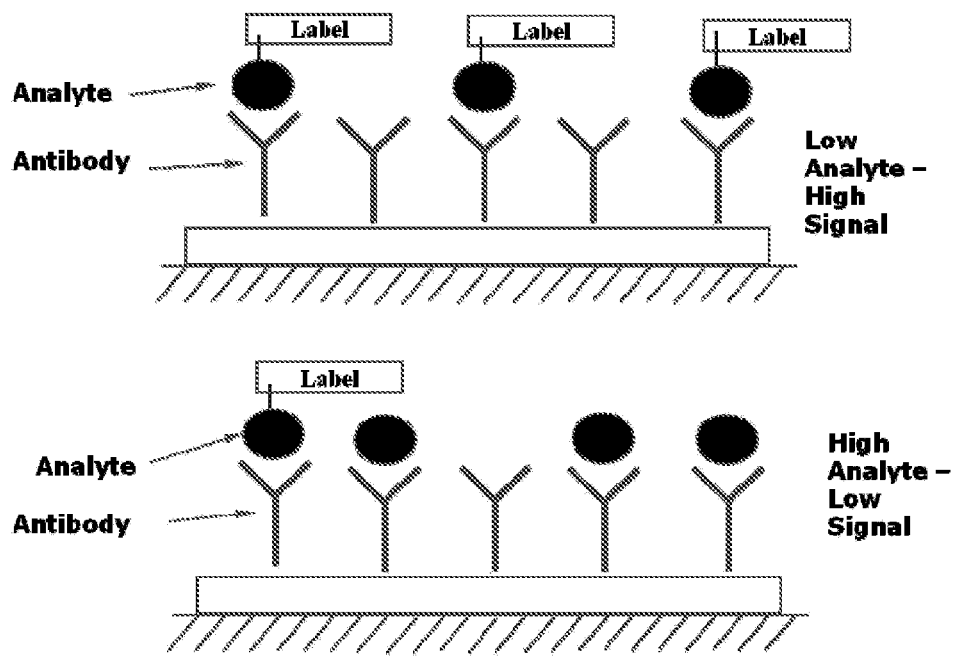
FIG. 4 shows the competitive immunoassay format used on a lateral flow assay device.
Figure 5:
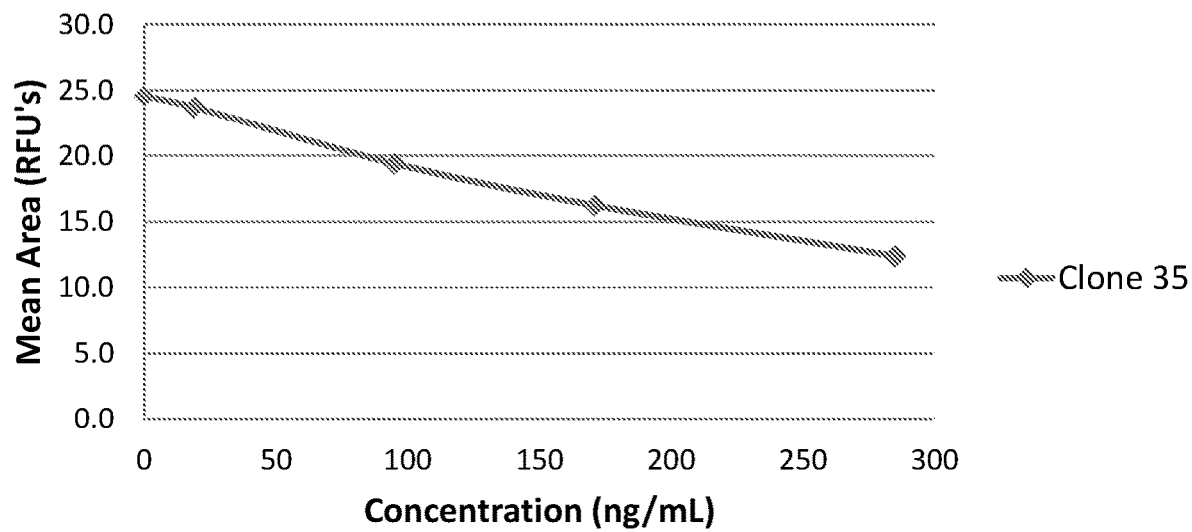
FIG. 5 shows a typical dose response curve generated with olanzapine antibody clone 35.
Figure 6:
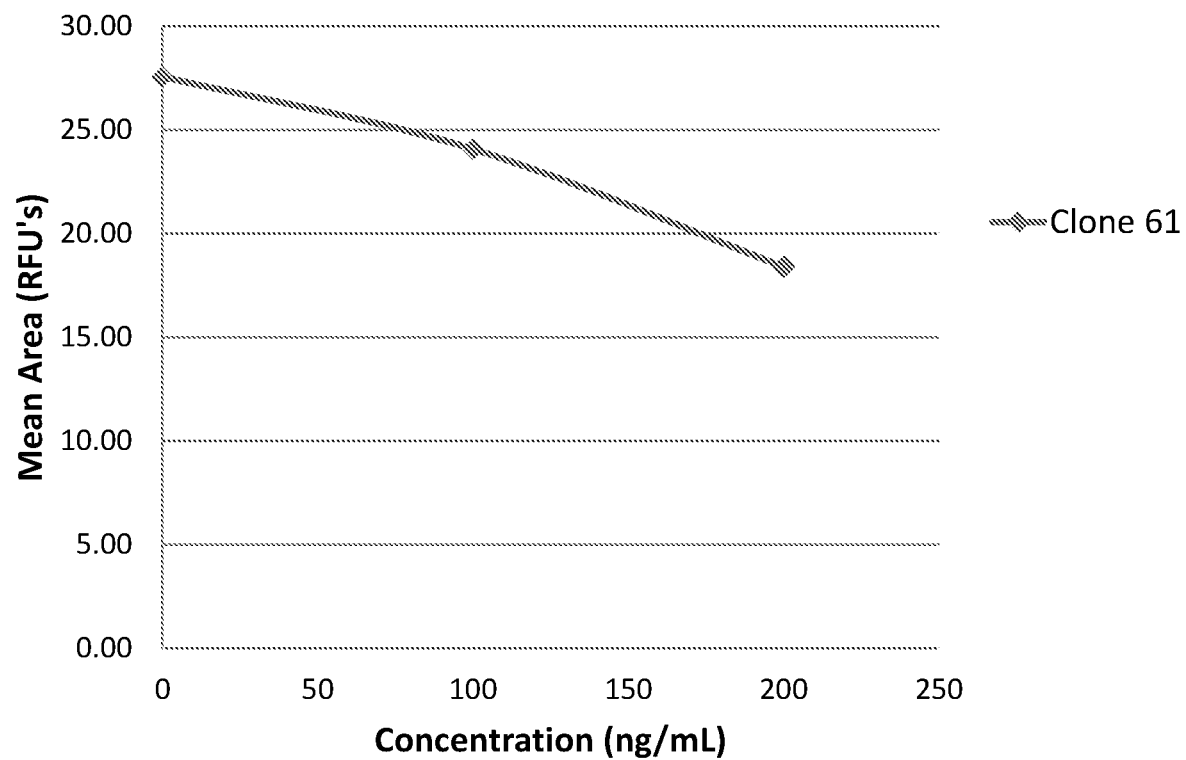
FIG. 6 shows a typical dose response curve generated with olanzapine antibody clone 61.
Figure 7:
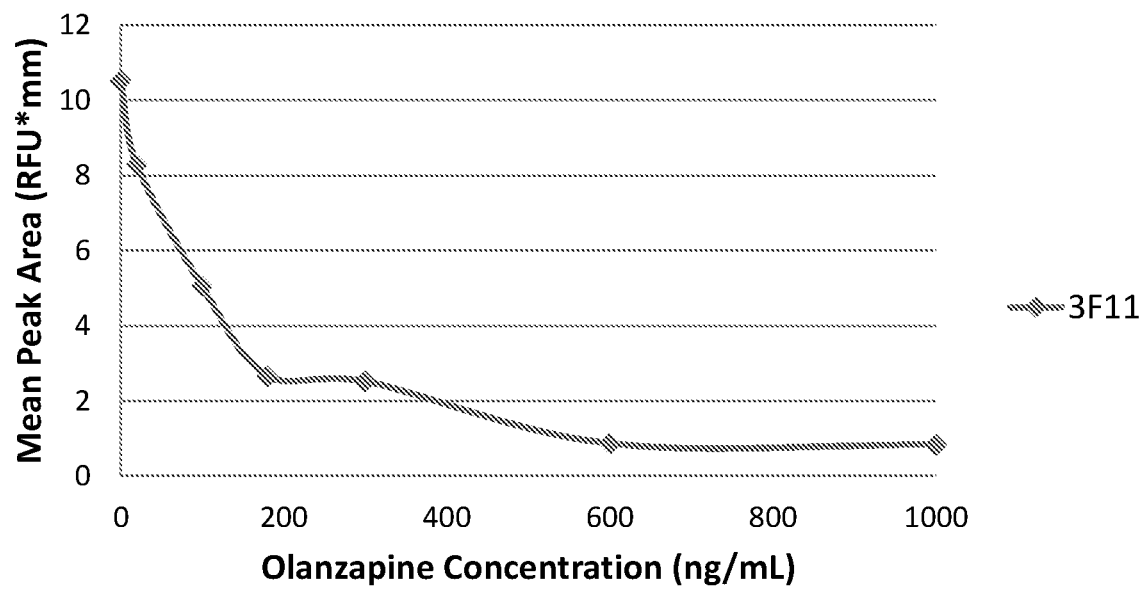
FIG. 7 shows a typical dose response curve generated with olanzapine antibody 3F11.

FIG. 4 shows the competitive immunoassay format used on a lateral flow assay device in which the capture antibody, an olanzapine clone, was deposited on a chip along with a detection conjugate consisting of olanzapine conjugated to a fluorophore. In this competitive format as show in FIG. 4, a low level of analyte (olanzapine) results in high signal, whereas a high level of analyte (olanzapine) results in low signal. The amount of olanzapine in the sample can be calculated from the loss of fluorescence compared to a control sample with no drug present. A typical dose response curve generated with olanzapine clone 35 is shown in FIG. 5, with olanzapine clone 61 is shown in FIG. 6, and with olanzapine clone 3F11 is shown in FIG. 7.

Figure 8:
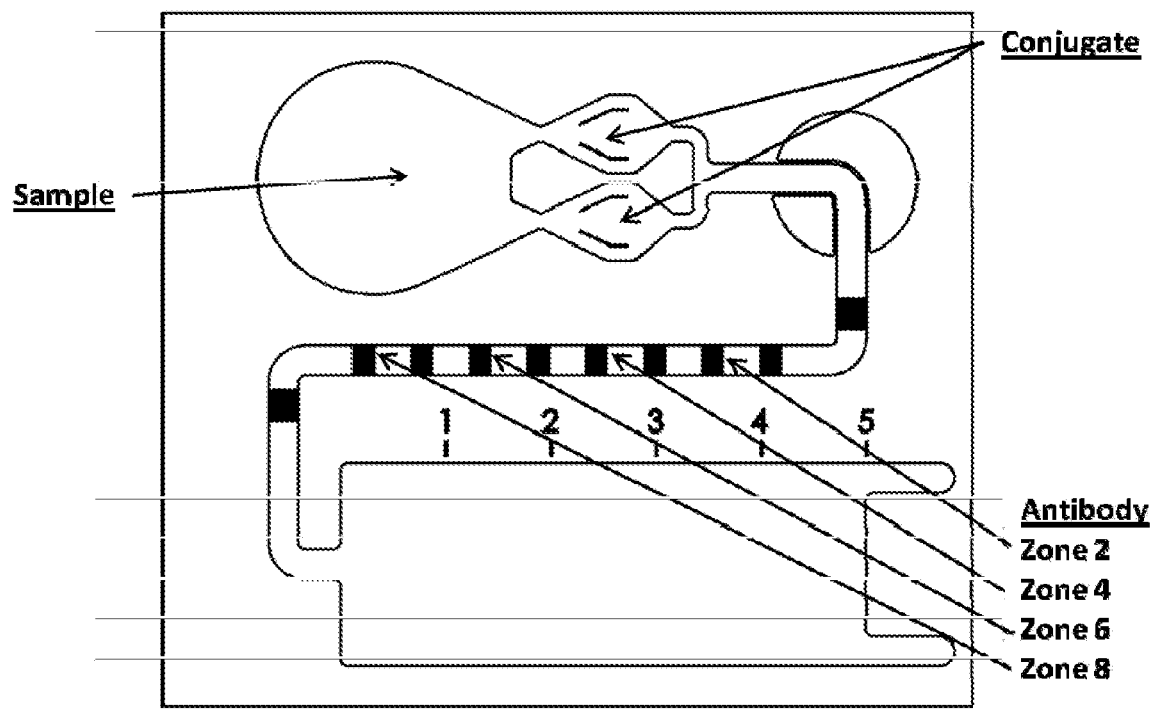
FIG. 8 shows the chip design of a lateral flow assay device according to the subject invention.
Figure 9:
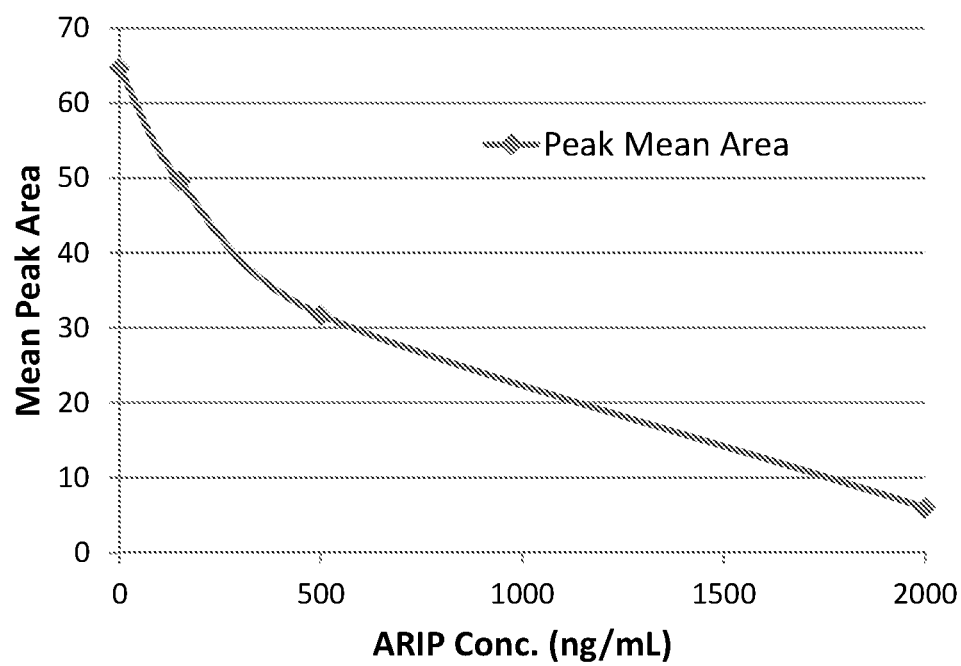
FIG. 9 shows a typical dose response curve for an aripiprazole positive control generated with antibody 5C7 and a labeled aripiprazole competitive binding partner.
Figure 10:
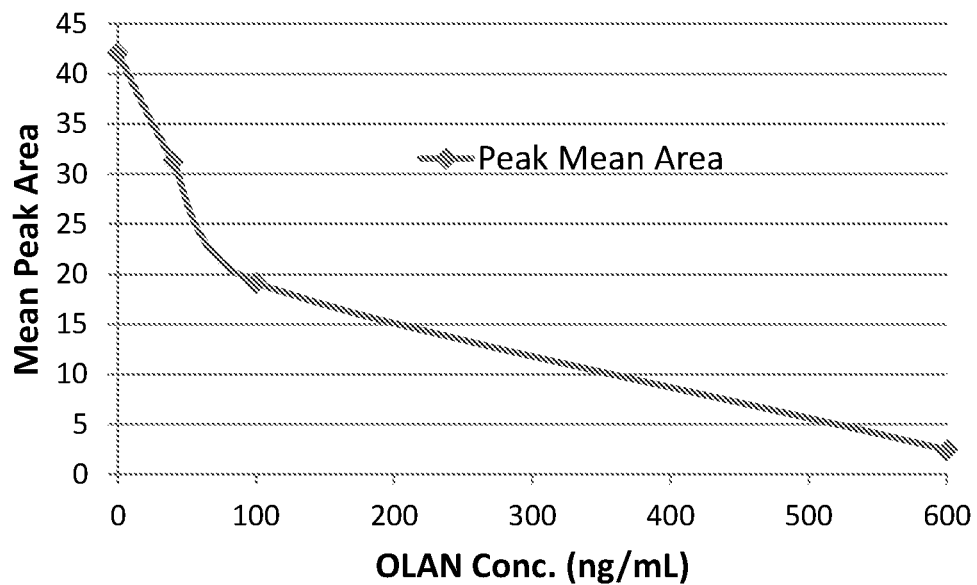
FIG. 10 shows a typical dose response curve for an olanzapine positive control generated with antibody 4G9-1 and a labeled olanzapine competitive binding partner.
Figure 11:
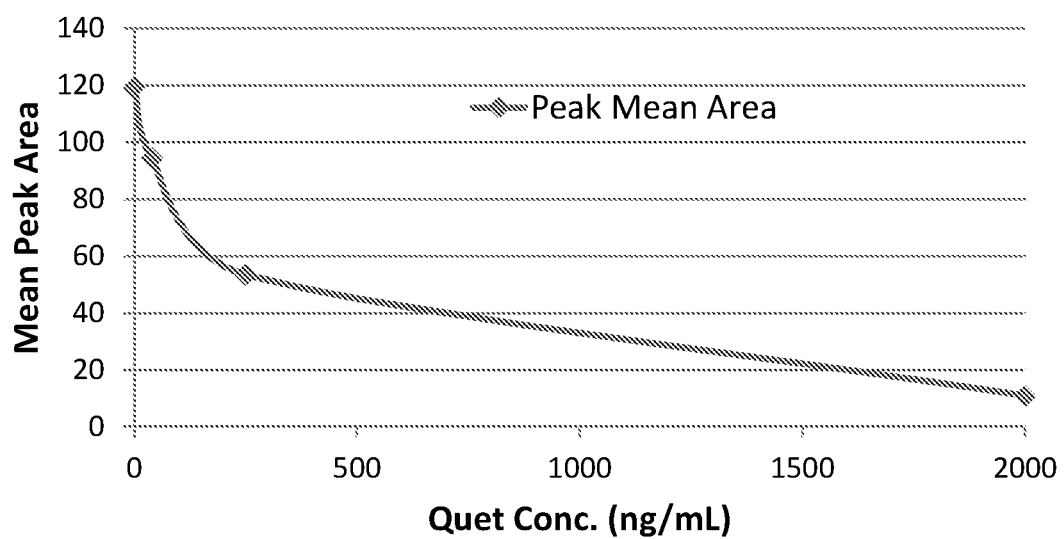
FIG. 11 shows a typical dose response curve for a quetiapine positive control generated with antibody 11 and a labeled quetiapine competitive binding partner.

FIG. 8 shows the chip design of a lateral flow assay device according to one embodiment of the subject invention. The device includes a zone or area for receiving the sample, a conjugate zone (which contains desired labeled competitive binding partner(s)), and a reaction zone (eight areas within the reaction zone are indicated; each area can contain a separate desired antibody). Sample flows from the sample zone through the conjugate zone and to the reaction zone.

Figure 12:
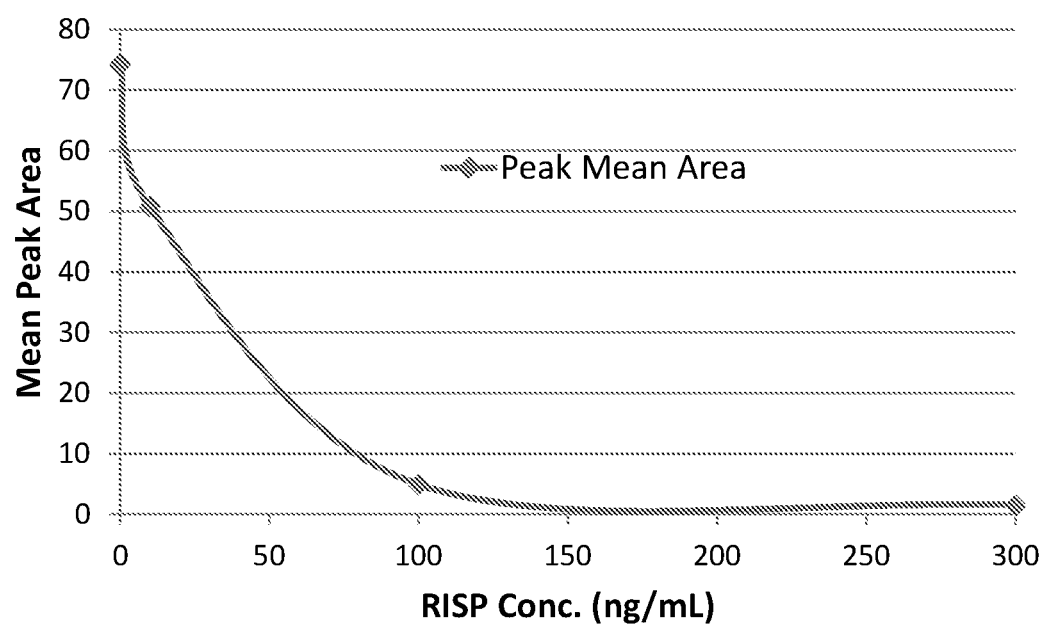
FIG. 12 shows a typical dose response curve for a risperidone positive control generated with antibody 5-9 and a labeled risperidone competitive binding partner.

FIGS. 9-12 show typical dose response curves for an aripiprazole positive control (sample containing aripiprazole) generated with antibody 5C7 deposited in reaction zone 2 and a labeled aripiprazole competitive binding partner in the conjugate zone (FIG. 9), an olanzapine positive control (sample containing olanzapine) generated with antibody 4G9-1 deposited in reaction zone 4 and a labeled olanzapine competitive binding partner in the conjugate zone (FIG. 10), a quetiapine positive control (sample containing quetiapine) generated with antibody 11 deposited in reaction zone 6 and a labeled quetiapine competitive binding partner in the conjugate zone (FIG. 11), and a risperidone positive control (sample containing risperidone) generated with antibody 5-9 deposited in reaction zone 8 and a labeled risperidone competitive binding partner in the conjugate zone (FIG. 12). The labeled competitive binding partners in the conjugate zone compete with the drugs present in the samples for binding to the antibodies. The amount of label is detected and is an indication of the amount of drug present in the sample (the amount of signal being inversely proportional to the amount of drug in the sample—see FIG. 4).

In order to confirm that conjugates of labeled competitive binding partners do not bind to antibodies deposited in the reaction zones, negative controls were conducted by using samples containing no drugs. Referring to Table 3, a sample containing no aripiprazole is deposited in the sample zone and moves by capillary action through the conjugate zone (this time containing labeled olanzapine, labeled quetiapine, and labeled risperidone, but no labeled aripiprazole) and to the reaction zone. The reaction zone again contains aripiprazole antibody (5C7) in reaction zone 2. Table 3 below shows the results, confirming that there is no dose response and the olanzapine, quetiapine, and risperidone conjugates that move by capillary action through the reaction zone do not bind to the aripiprazole antibody.

TABLE 3

| Aripiprazole-Clone 5C7-Math Model 1 (0 ng/mL Conc.) | | | | | | |
|---|---|---|---|---|---|---|
| Assay-MM | Conj | Reaction Zone | Read Position | Peak Mean Area | Peak Mean Height | Mean Background |
| ARIP-MM1 | OLAN, QUET, RISP | ARIP | 2 | 0.77 | 1.56 | 3.99 |
| ARIP-MM1 | OLAN, QUET, RISP | | 4 | −0.02 | 0.06 | 4.14 |
| ARIP-MM1 | OLAN, QUET, RISP | | 6 | 0.09 | 0.10 | 4.29 |
| ARIP-MM1 | OLAN, QUET, RISP | | 8 | 0.13 | 0.12 | 4.61 |

Other Conjugates do not bind to Aripiprazole

Referring to Table 4, a sample containing no olanzapine is deposited in the sample zone and moves by capillary action through the conjugate zone (this time containing labeled aripiprazole, labeled quetiapine, and labeled risperidone, but no labeled olanzapine) and to the reaction zone. The reaction zone again contains olanzapine antibody (4G9-1) in reaction zone 4. Table 4 below shows the results, confirming that there is no dose response and the aripiprazole, quetiapine, and risperidone conjugates that move by capillary action through the reaction zone do not bind to the olanzapine antibody.

TABLE 4

| OLAN-Clone 4G9-1-Math Model 1 (0 ng/mL Conc.) | | | | | | |
|---|---|---|---|---|---|---|
| Assay-MM | Conj | Reaction Zone | Read Position | Peak Mean Area | Peak Mean Height | Mean Background |
| OLAN-MM1 | ARIP, QUET, RISP | | 2 | −0.03 | 0.05 | 4.38 |
| OLAN-MM1 | ARIP, QUET, RISP | OLAN | 4 | 0.74 | 1.10 | 4.56 |
| OLAN-MM1 | ARIP, QUET, RISP | | 6 | 0.06 | 0.09 | 4.79 |
| OLAN-MM1 | ARIP, QUET, RISP | | 8 | 0.11 | 0.13 | 5.17 |

Other Conjugates do not bind to Olanzapine

Referring to Table 5, a sample containing no quetiapine is deposited in the sample zone and moves by capillary action through the conjugate zone (this time containing labeled aripiprazole, labeled olanzapine, and labeled risperidone, but no labeled quetiapine) and to the reaction zone. The reaction zone again contains quetiapine antibody (11) in reaction zone 6. Table 5 below shows the results, confirming that there is no dose response and the aripiprazole, olanzapine, and risperidone conjugates that move by capillary action through the reaction zone do not bind to the quetiapine antibody

TABLE 5

| Quetiapine-Clone 11-Math Model 1 (0 ng/mL Conc.) | | | | | | |
|---|---|---|---|---|---|---|
| Assay-MM | Conj | Reaction Zone | Read Position | Peak Mean Area | Peak Mean Height | Mean Background |
| QUET-MM1 | ARIP, OLAN, RISP | | 2 | −0.01 | 0.07 | 3.85 |
| QUET-MM1 | ARIP, OLAN, RISP | | 4 | 0.01 | 0.12 | 4.01 |
| QUET-MM1 | ARIP, OLAN, RISP | QUET | 6 | 0.03 | 0.08 | 4.24 |
| QUET-MM1 | ARIP, OLAN, RISP | | 8 | 0.04 | 0.07 | 4.56 |

Other Conjugates do not bind to Quetiapine

Referring to Table 6, a sample containing no risperidone is deposited in the sample zone and moves by capillary action through the conjugate zone (this time containing labeled aripiprazole, labeled olanzapine, and labeled quetiapine, but no labeled risperidone) and to the reaction zone. The reaction zone again contains risperidone antibody (5-9) in reaction zone 8. Table 6 below shows the results, confirming that there is no dose response and the aripiprazole, olanzapine, and quetiapine conjugates that move by capillary action through the reaction zone do not bind to the risperidone antibody.

TABLE 6

| Risperidone-Clone 5-9-Math Model 1 (0 ng/mL Conc.) | | | | | | |
|---|---|---|---|---|---|---|
| Assay-MM | Conj | Reaction Zone | Read Position | Peak Mean Area | Peak Mean Height | Mean Background |
| RISP-MM1 | ARIP, OLAN, QUET | | 2 | 0.02 | 0.11 | 7.43 |
| RISP-MM1 | ARIP, OLAN, QUET | | 4 | 0.05 | 0.14 | 7.73 |
| RISP-MM1 | ARIP, OLAN, QUET | | 6 | 0.20 | 0.19 | 8.11 |
| RISP-MM1 | ARIP, OLAN, QUET | RISP | 8 | 1.97 | 3.23 | 8.85 |

Other Conjugates do not bind to Risperidone

In order to confirm that conjugates of labeled competitive binding partners bind only to their respective antibodies deposited in the reaction zones, additional negative controls were conducted by again using samples containing no drugs. Referring to Table 7, a sample containing no aripiprazole is deposited in the sample zone and moves by capillary action through the conjugate zone (this time containing labeled aripiprazole) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 7 below shows the results, confirming that there is no dose response except to the aripiprazole antibody 5C7 (in reaction zone 2).

TABLE 7

| Aripiprazole-Clone 5C7-Math Model 1 (0 ng/mL Conc.) | | | | | | |
|---|---|---|---|---|---|---|
| Assay-MM | Conj | Reaction Zone | Read Position | Peak Mean Area | Peak Mean Height | Mean Background |
| ARIP-MM1 | ARIP, OLAN, QUET, RISP | ARIP | 2 | 60.34 | 97.53 | 5.44 |
| ARIP-MM1 | ARIP, OLAN, QUET, RISP | | 4 | 2.86 | 3.91 | 11.66 |
| ARIP-MM1 | ARIP, OLAN, QUET, RISP | | 6 | 1.12 | 1.23 | 11.03 |
| ARIP-MM1 | ARIP, OLAN, QUET, RISP | | 8 | 3.14 | 4.19 | 12.94 |

Only the Aripiprazole Reaction Zone is binding

Referring to Table 8, a sample containing no olanzapine is deposited in the sample zone and moves by capillary action through the conjugate zone (this time containing labeled olanzapine) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 8 below shows the results, confirming that there is no dose response except to the olanzapine antibody 4G9-1 (in reaction zone 4).

TABLE 8

| OLAN-Clone 4G9-1-Math Model 1 (0 ng/mL Conc.) | | | | | | |
|---|---|---|---|---|---|---|
| Assay-MM | Conj | Reaction Zone | Read Position | Peak Mean Area | Peak Mean Height | Mean Background |
| OLAN-MM1 | ARIP, OLAN, QUET, RISP | | 2 | 0.02 | 0.08 | 4.86 |
| OLAN-MM1 | ARIP, OLAN, QUET, RISP | OLAN | 4 | 34.23 | 51.80 | 5.39 |
| OLAN-MM1 | ARIP, OLAN, QUET, RISP | | 6 | 0.22 | 0.32 | 5.39 |
| OLAN-MM1 | ARIP, OLAN, QUET, RISP | | 8 | 0.15 | 0.17 | 5.59 |

Only the Olanzapine Reaction Zone is binding

Referring to Table 9, a sample containing no quetiapine is deposited in the sample zone and moves by capillary action through the conjugate zone (this time containing labeled quetiapine) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 9 below shows the results, confirming that there is no dose response except to the quetiapine antibody 11 (in reaction zone 6).

TABLE 9

Quetiapine-Clone 11-Math Model 1 (0 ng/mL Conc.)

| Assay-MM | Conj | Reaction Zone | Read Position | Peak Mean Area | Peak Mean Height | Mean Background |
|---|---|---|---|---|---|---|
| QUET-MM1 | ARIP, OLAN, QUET, RISP | | 2 | 0.13 | 0.41 | 10.02 |
| QUET-MM1 | ARIP, OLAN, QUET, RISP | | 4 | 0.08 | 0.23 | 10.47 |
| QUET-MM1 | ARIP, OLAN, QUET, RISP | QUET | 6 | 140.35 | 181.33 | 7.91 |
| QUET-MM1 | ARIP, OLAN, QUET, RISP | | 8 | 1.58 | 2.61 | 11.53 |

Only the Quetiapine Reaction Zone is binding

Referring to Table 10, a sample containing no risperidone is deposited in the sample zone and moves by capillary action through the conjugate zone (this time containing labeled risperidone) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 10 below shows the results, confirming that there is no dose response except to the risperidone antibody 5-9 (in reaction zone 8).

TABLE 10

Risperidone-Clone 5-9-Math Model 1 (0 ng/mL Conc.)

| Assay-MM | Conj | Reaction Zone | Read Position | Peak Mean Area | Peak Mean Height | Mean Background |
|---|---|---|---|---|---|---|
| RISP-MM1 | ARIP, OLAN, QUET, RISP | | 2 | 1.03 | 1.51 | 9.07 |
| RISP-MM1 | ARIP, OLAN, QUET, RISP | | 4 | 0.65 | 0.91 | 9.60 |
| RISP-MM1 | ARIP, OLAN, QUET, RISP | | 6 | 2.61 | 6.39 | 10.48 |
| RISP-MM1 | ARIP, OLAN, QUET, RISP | RISP | 8 | 55.98 | 100.91 | 11.58 |

Only the Risperidone Reaction Zone is binding

The results shown above confirm that conjugates of labeled competitive binding partners bind only to their respective antibodies in the reaction zone.

Figure 13:
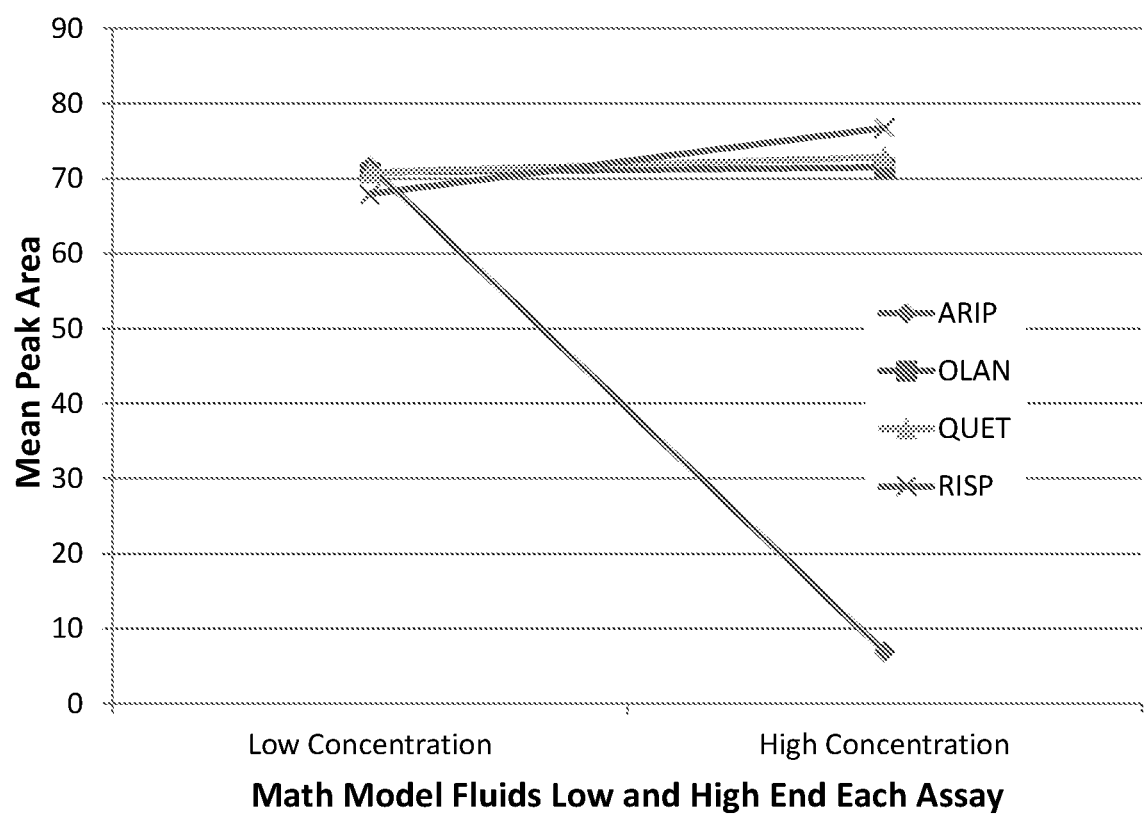
FIG. 13 shows a typical dose response curve for a sample containing aripiprazole generated with aripiprazole antibody 5C7 in the presence of labeled aripiprazole competitive binding partner, with no dose response curve for olanzapine, quetiapine, or risperidone in the presence of a labeled competitive binding partner for each.

FIGS. 13-16 show typical dose response curves in specific antibody reaction zones, and proof of dose response low/high concentration for each specific assay in the presence of other conjugates. In FIG. 13, a sample containing aripiprazole is deposited in the sample zone and moves by capillary action through the conjugate zone (this time containing labeled aripiprazole, labeled olanzapine, labeled quetiapine, and labeled risperidone) and to the reaction zone. The reaction zone again contains aripiprazole antibody (5C7) in reaction zone 2. A typical dose response curve was generated as is shown in FIG. 13 only for aripiprazole, and not for olanzapine, quetiapine, or risperidone.

Figure 14:
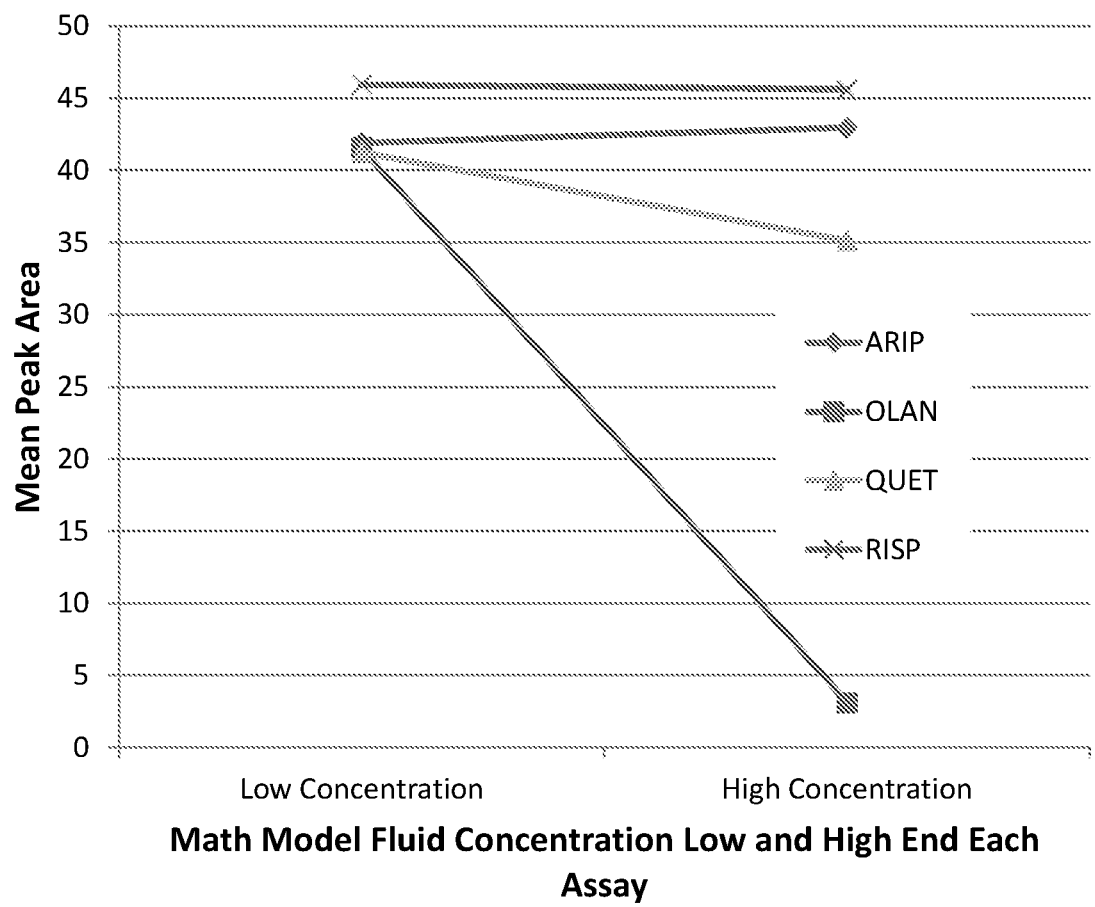
FIG. 14 shows a typical dose response curve for a sample containing olanzapine generated with olanzapine antibody 4G9-1 in the presence of a labeled olanzapine competitive binding partner, with no dose response curve for aripiprazole, quetiapine, or risperidone in the presence of a labeled competitive binding partner for each.

In FIG. 14, a sample containing olanzapine is deposited in the sample zone and moves by capillary action through the conjugate zone (this time containing labeled aripiprazole, labeled olanzapine, labeled quetiapine, and labeled risperidone) and to the reaction zone. The reaction zone again contains olanzapine antibody (4G9-1) in reaction zone 4. A typical dose response curve was generated as is shown in FIG. 14 only for olanzapine, and not for aripiprazole, quetiapine, or risperidone.

Figure 15:
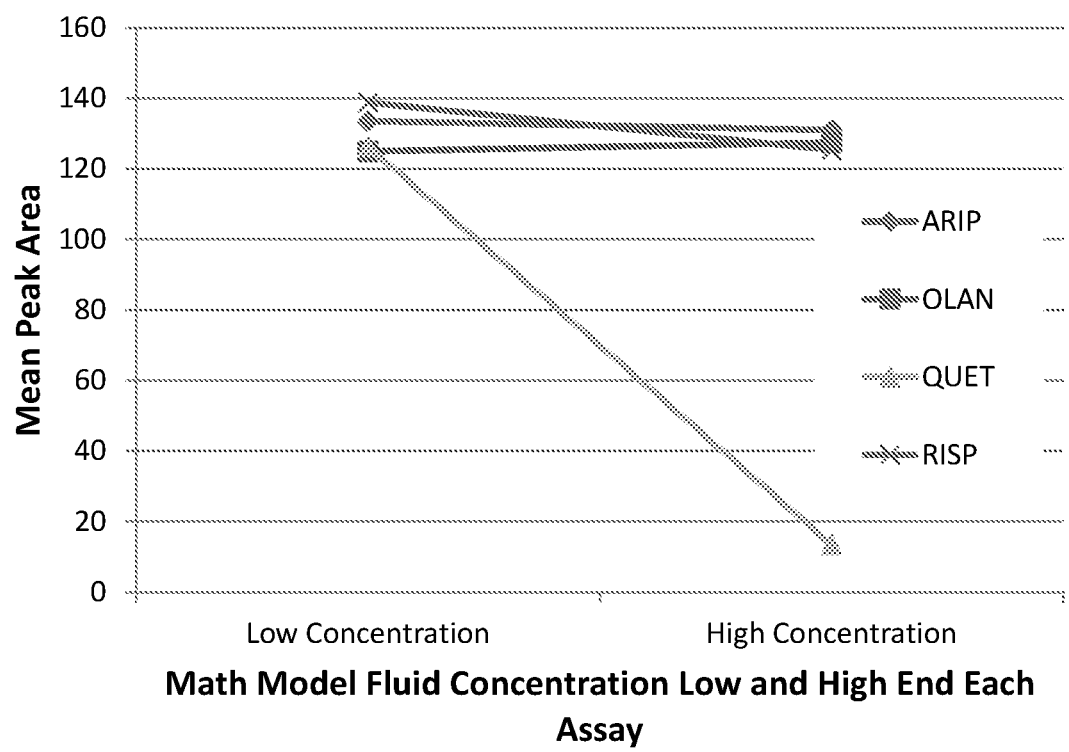
FIG. 15 shows a typical dose response curve for a sample containing quetiapine generated with quetiapine antibody 11 in the presence of a labeled quetiapine competitive binding partner, with no dose response curve for aripiprazole, olanzapine, or risperidone in the presence of a labeled competitive binding partner for each.

In FIG. 15, a sample containing quetiapine is deposited in the sample zone and moves by capillary action through the conjugate zone (this time containing labeled aripiprazole, labeled olanzapine, labeled quetiapine, and labeled risperidone) and to the reaction zone. The reaction zone again contains quetiapine antibody (11) in reaction zone 6. A typical dose response curve was generated as is shown in FIG. 15 only for quetiapine, and not for aripiprazole, olanzapine, or risperidone.

Figure 16:
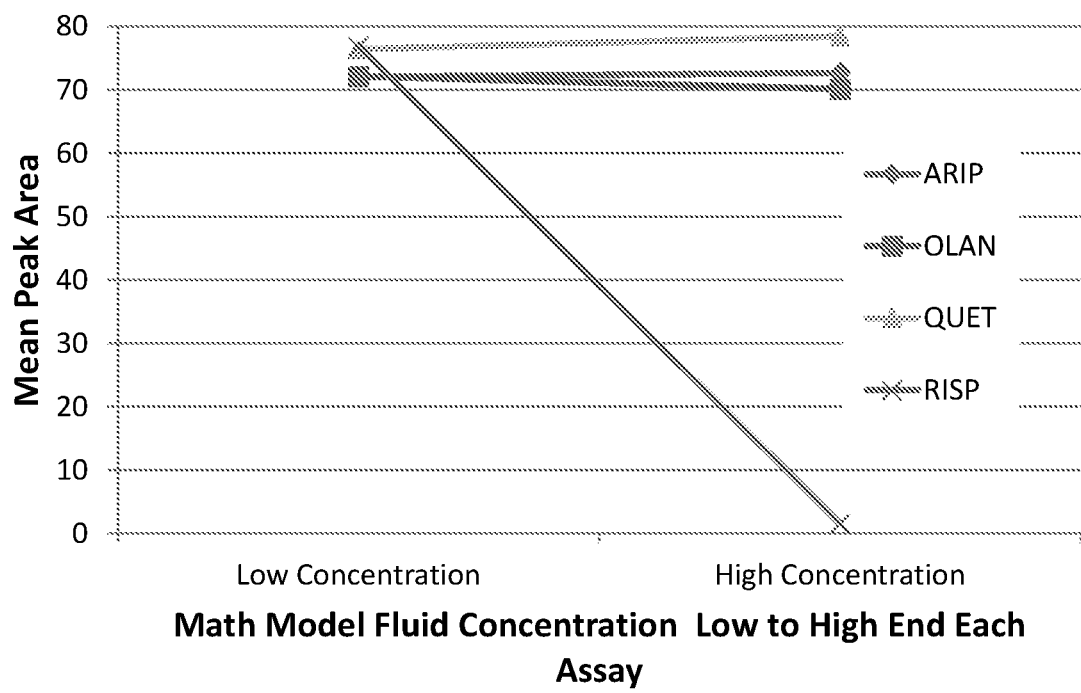
FIG. 16 shows a typical dose response curve for a sample containing risperidone generated with risperidone antibody 5-9 in the presence of a labeled risperidone competitive binding partner, with no dose response curve for aripiprazole, olanzapine, or quetiapine in the presence of a labeled competitive binding partner for each.

In FIG. 16, a sample containing risperidone is deposited in the sample zone and moves by capillary action through the conjugate zone (this time containing labeled aripiprazole, labeled olanzapine, labeled quetiapine, and labeled risperidone) and to the reaction zone. The reaction zone again contains risperidone antibody (5-9) in reaction zone 8. A typical dose response curve was generated as is shown in FIG. 16 only for risperidone, and not for aripiprazole, olanzapine, or quetiapine.

Figure 17:
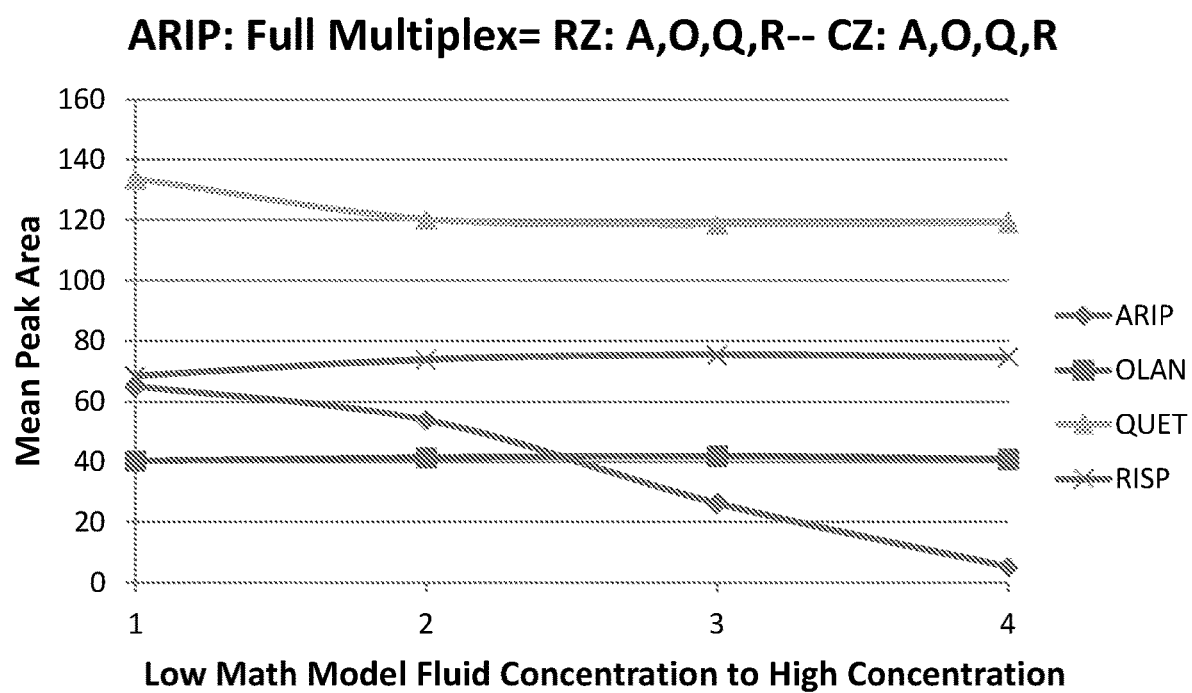
FIG. 17 shows a typical dose response curve for a sample containing aripiprazole generated with aripiprazole antibody 5C7 in the presence of a labeled aripiprazole competitive binding partner, with no dose response curve for olanzapine, quetiapine, or risperidone in the presence of antibody and labeled competitive binding partner for each.
Figure 18:
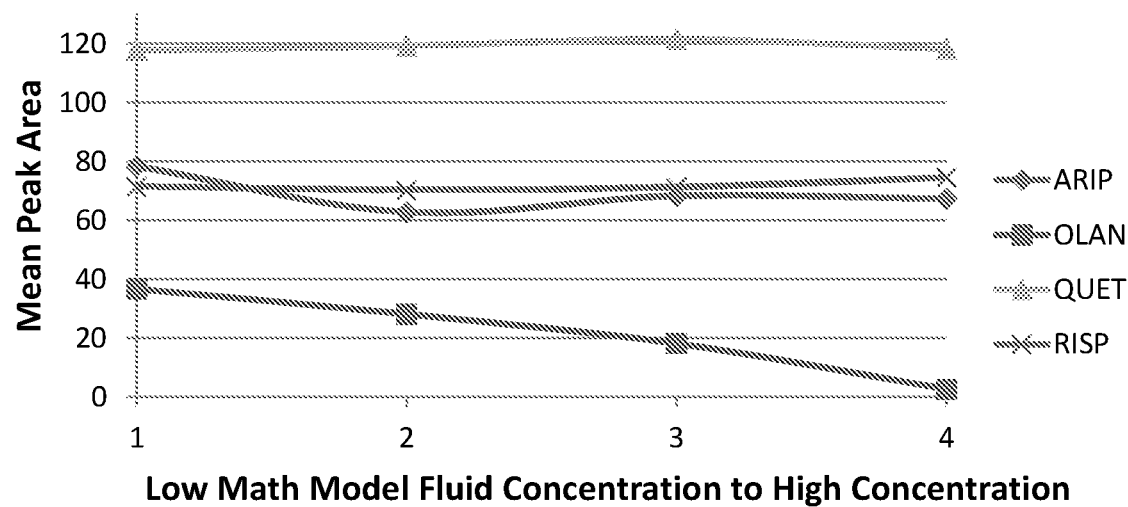
FIG. 18 shows a typical dose response curve for a sample containing olanzapine generated with olanzapine antibody 4G9-1 in the presence of a labeled olanzapine competitive binding partner, with no dose response curve for aripiprazole, quetiapine, or risperidone in the presence of antibody and labeled competitive binding partner for each.
Figure 19:
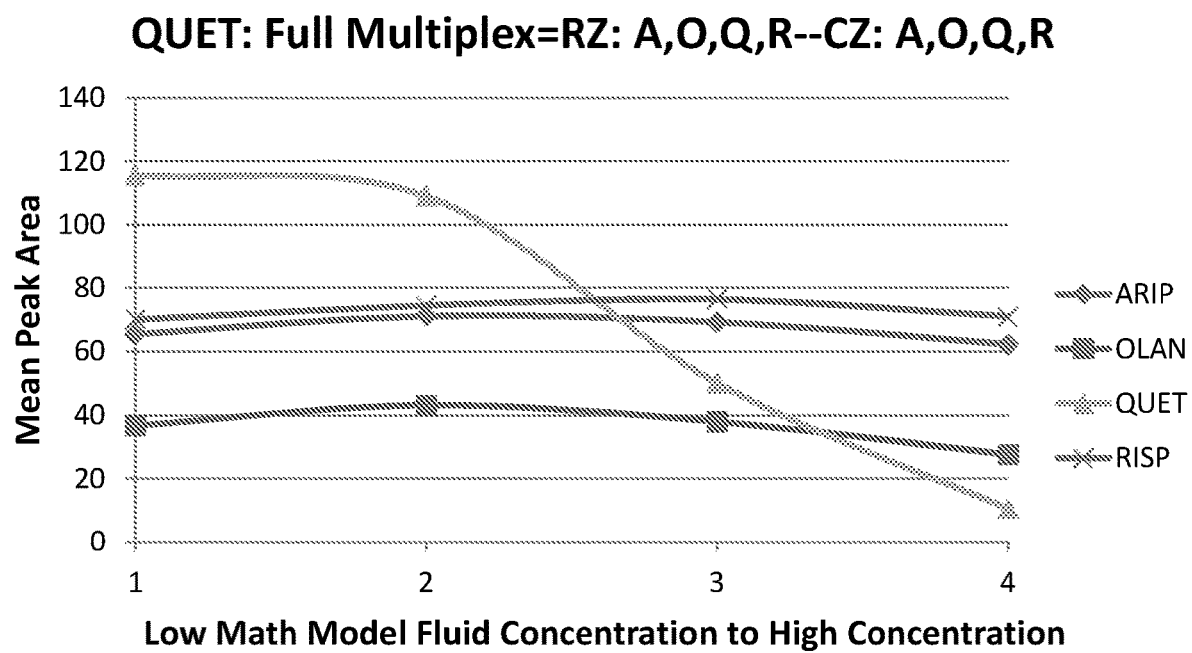
FIG. 19 shows a typical dose response curve for a sample containing quetiapine generated with quetiapine antibody 11 in the presence of labeled quetiapine competitive binding partner, with no dose response curve for aripiprazole, olanzapine, or risperidone in the presence of antibody and labeled competitive binding partner for each.
Figure 20:
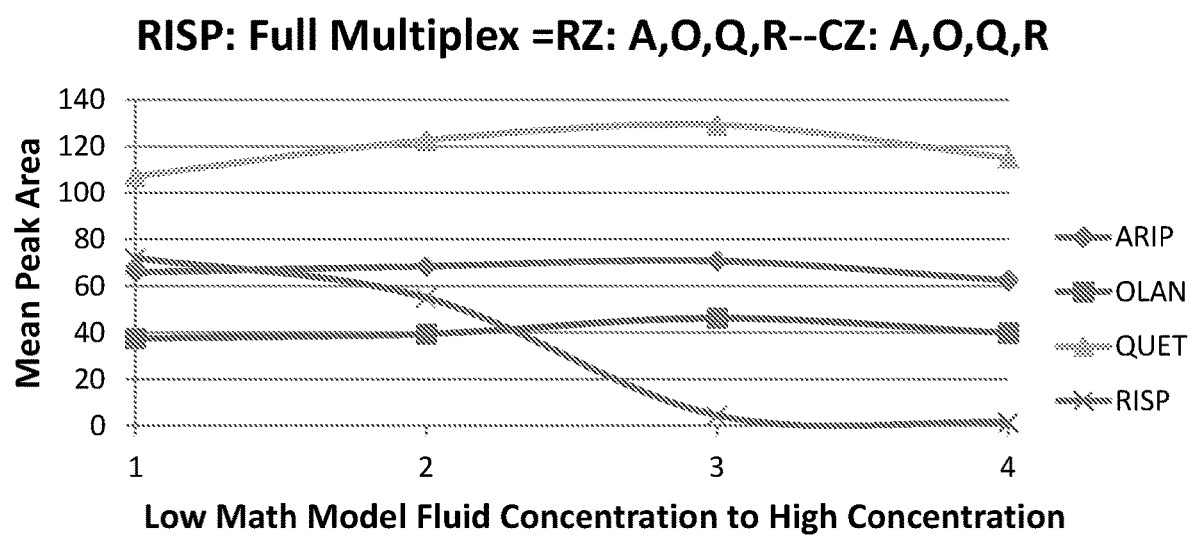
FIG. 20 shows a typical dose response curve for a sample containing risperidone generated with risperidone antibody 5-9 in the presence of a labeled risperidone competitive binding partner, with no dose response curve for aripiprazole, olanzapine, or quetiapine in the presence of antibody and labeled competitive binding partner for each.

FIGS. 17-20 show typical dose response curves for each assay in the presence of other conjugates and antibodies. In FIG. 17, a sample containing aripiprazole is deposited in the sample zone and moves by capillary action through the conjugate zone (again containing labeled aripiprazole, labeled olanzapine, labeled quetiapine, and labeled risperidone) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. A typical dose response curve was generated for aripiprazole, as is shown in FIG. 17. When a sample containing olanzapine was deposited in the sample zone of this chip, a typical dose response curve was generated for olanzapine as shown in FIG. 18. When a sample containing quetiapine was deposited in the sample zone of this chip, a typical dose response curve for quetiapine was generated as shown in FIG. 19. When a sample containing risperidone was deposited in the sample zone of this chip, a typical dose response curve for risperidone was generated as shown in FIG. 20.

Figure 21:
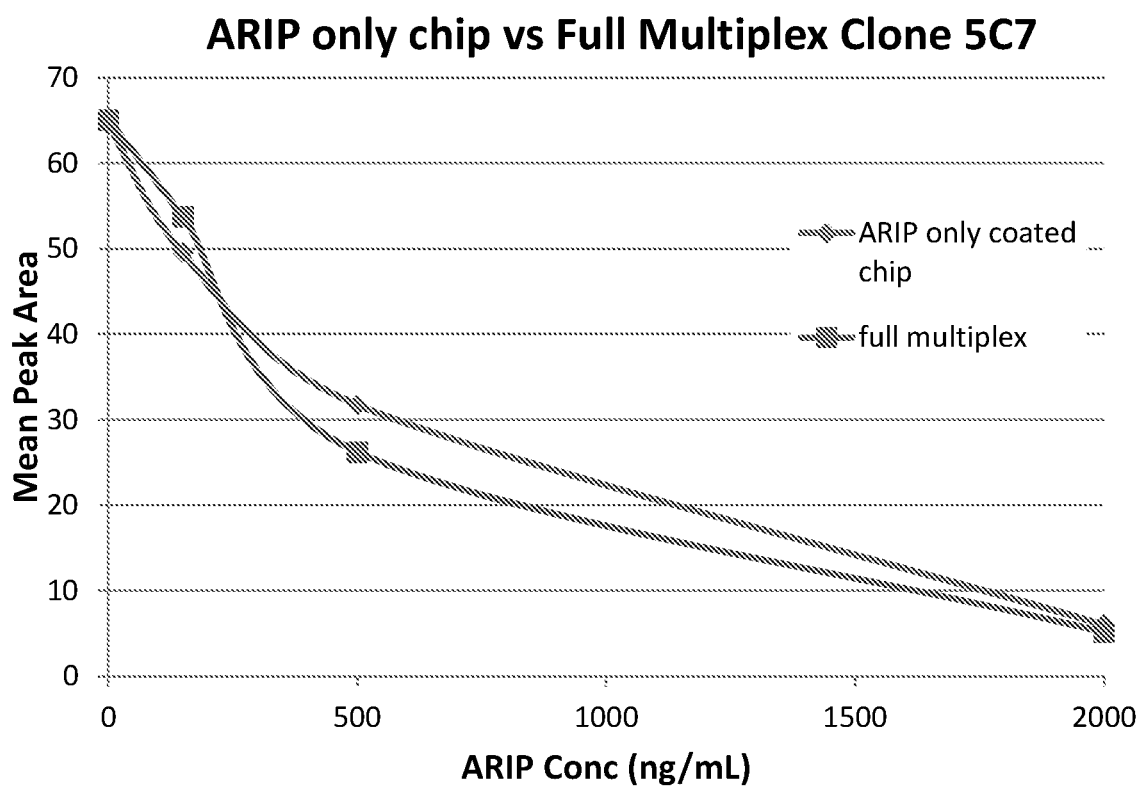
FIG. 21 shows a comparison of the aripiprazole dose response curve generated as a positive control to the aripiprazole dose response curve generated in the multiplex format.
Figure 22:
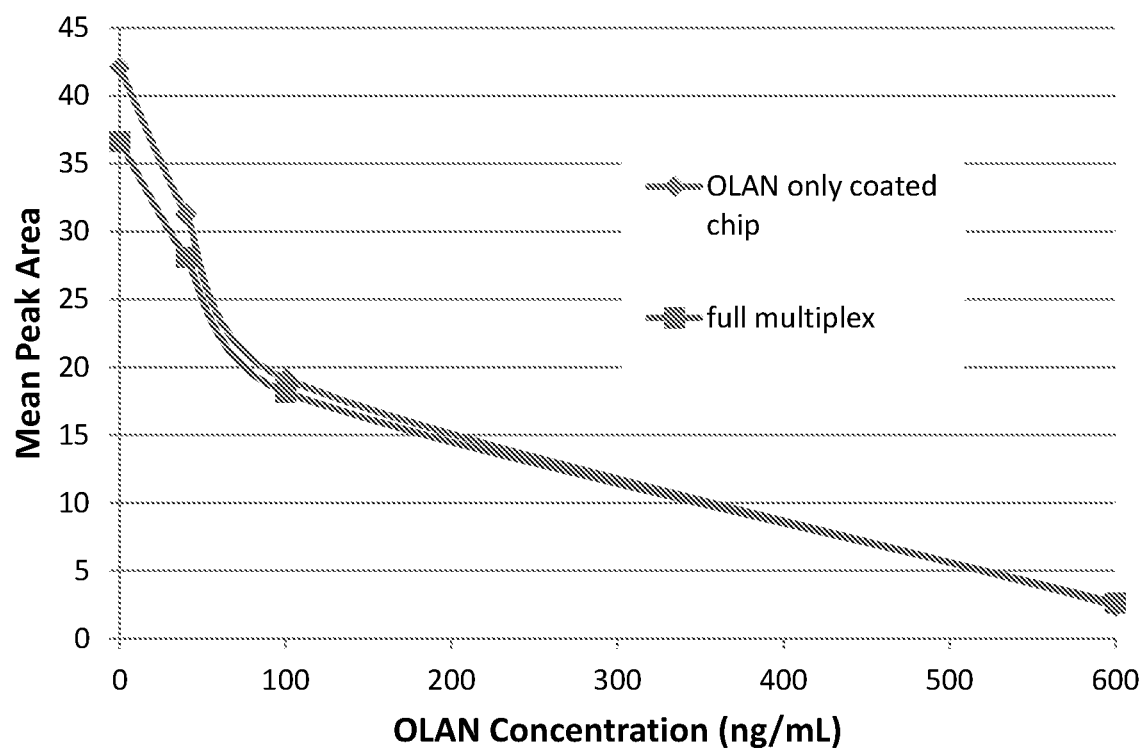
FIG. 22 shows a comparison of the olanzapine dose response curve generated as a positive control to the olanzapine dose response curve generated in the multiplex format.
Figure 23:
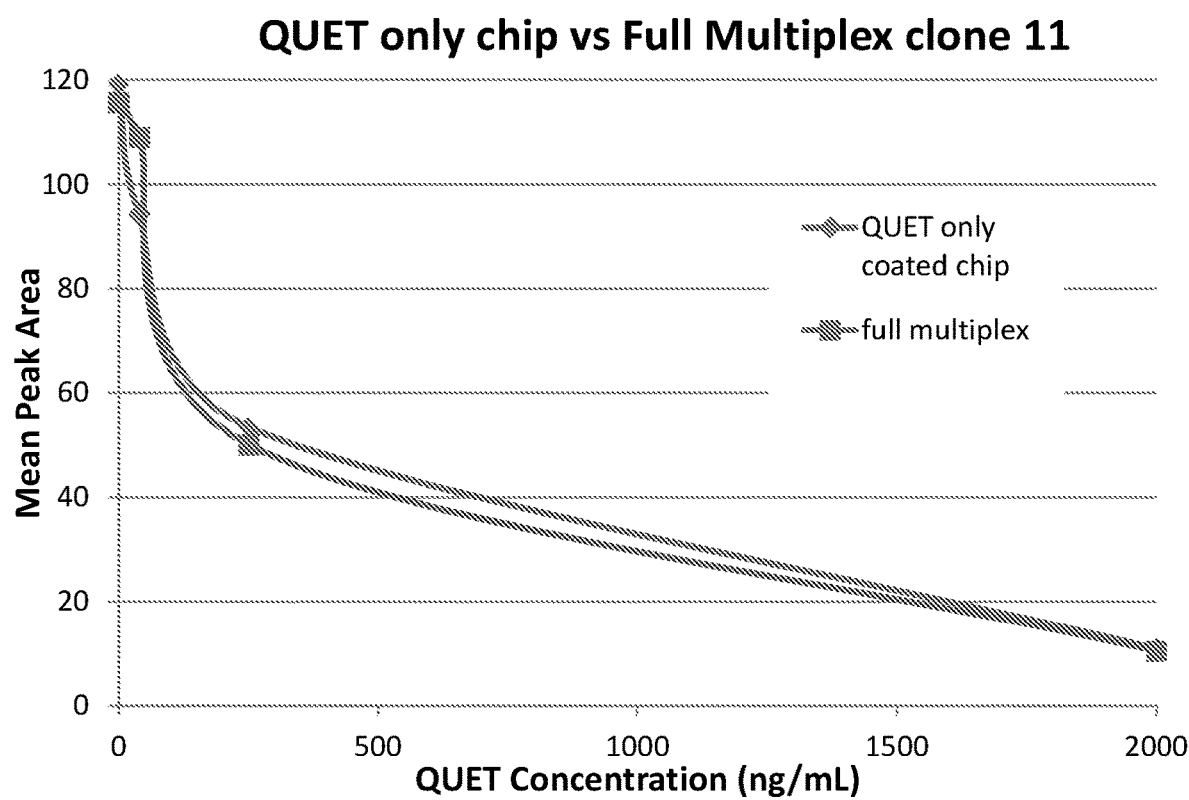
FIG. 23 shows a comparison of the quetiapine dose response curve generated as a positive control to the quetiapine dose response curve generated in the multiplex format.
Figure 24:
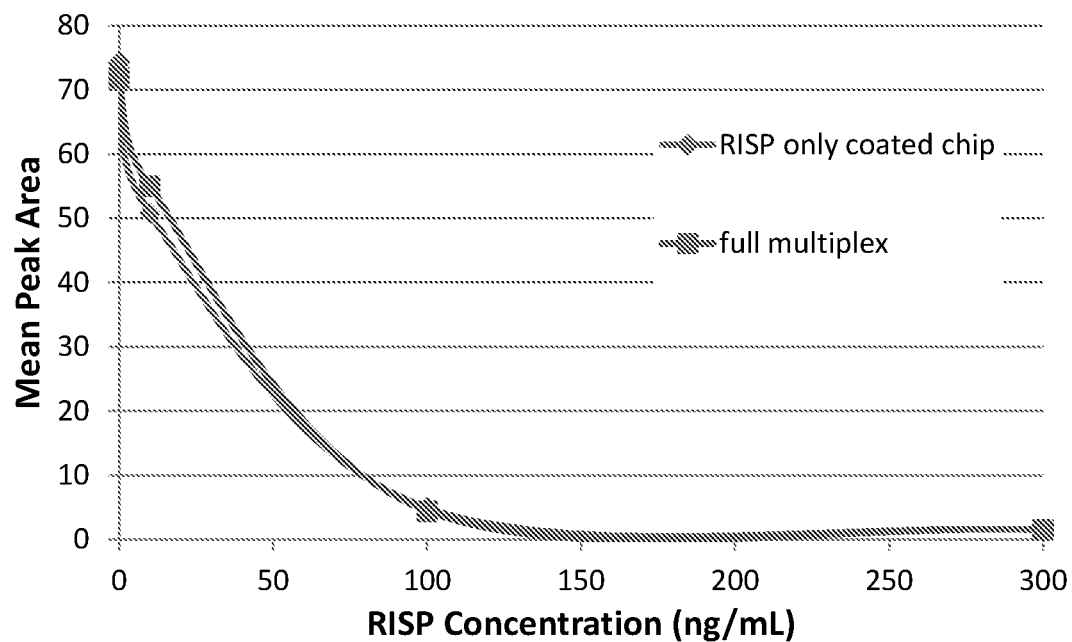
FIG. 24 shows a comparison of the risperidone dose response curve generated as a positive control to the risperidone dose response curve generated in the multiplex format.

FIGS. 21-24 show comparisons of dose response curves generated as positive controls (FIGS. 9-12) to dose response curves generated in the multiplex format (FIGS. 17-20). The comparison for aripiprazole is shown in FIG. 21; for olanzapine in FIG. 22; for quetiapine in FIG. 23; and for risperidone in FIG. 24. These figures show that the positive control curves are similar to the multiplex curves.

These data show that a lateral flow assay device of the subject invention can be used to detect multiple anti-psychotic drugs using a single sample from a patient on one portable, point-of-care device.

What is claimed is:

1. An isolated antibody or a binding fragment thereof, which binds to olanzapine, comprising:

a) a light chain variable region comprising a first complementarity-determining region (CDR1), a second complementarity-determining region (CDR2) a third complementarity-determining region (CDR3) of SEQ ID NO: 11 and having at least 90% sequence identity to the amino acid sequence of SEQ ID NO:11, and a heavy chain variable region comprising CDR1, CDR2 and CDR3 of SEQ ID NO: 12 and having at least 90% sequence identity to the amino acid sequence of SEQ ID NO:12, wherein (i) the light chain CDR1 comprises amino acid residues 44 to 54 of SEQ ID NO:11, (ii) the light chain CDR2 comprises amino acid residues 70 to 76 of SEQ ID NO:11, (iii) the light chain CDR3 comprises amino acid residues 109 to 117 of SEQ ID NO:11, (iv) the heavy chain CDR1 comprises amino acid residues 45 to 54 of SEQ ID NO:12, (v) the heavy chain CDR2 comprises amino acid residues 69 to 85 of SEQ ID NO:12, and (vi) the heavy chain CDR3 comprises amino acid residues 118 to 122 of SEQ ID NO:12;

b) a light chain variable region comprising CDR1, CDR2 and CDR3 of SEQ ID NO: 15 and having at least 90% sequence identity to the amino acid sequence of SEQ ID NO:15 and a heavy chain variable region comprising CDR1, CDR2 and CDR3 of SEQ ID NO: 16 and having at least 90% sequence identity to the amino acid sequence of SEQ ID NO:16, wherein (i) the light chain CDR1 comprises amino acid residues 44 to 54 of SEQ ID NO:15; (ii) the light chain CDR2 comprises amino acid residues 70 to 76 of SEQ ID NO:15, (iii) the light chain CDR3 comprises amino acid residues 109 to 117 of SEQ ID NO:15, (iv) the heavy chain CDR1 comprises amino acid residues 45 to 54 of SEQ ID NO:16, (v) the heavy chain CDR2 comprises amino acid residues 69 to 85 of SEQ ID NO:16, and (vi) the heavy chain CDR3 comprises amino acid residues 118 to 122 of SEQ ID NO:16;

c) a light chain variable region comprising CDR1, CDR2 and CDR3 of SEQ ID NO: 31 and having at least 90% sequence identity to the amino acid sequence of SEQ ID NO:31 and a heavy chain variable region comprising CDR1, CDR2 and CDR3 of SEQ ID NO: 32 and having at least 90% sequence identity to the amino acid sequence of SEQ ID NO:32, wherein (i) the light chain CDR1 comprises amino acid residues 44 to 54 of SEQ ID NO:31, (ii) the light chain CDR2 comprises amino acid residues 70 to 76 of SEQ ID NO:31, (iii) the light chain CDR3 comprises amino acid residues 109 to 117 of SEQ ID NO:31, (iv) the heavy chain CDR1 comprises amino acid residues 44 to 54 of SEQ ID NO:32, (v) the heavy chain CDR2 comprises amino acid residues 69 to 84 of SEQ ID NO:32; and (vi) the heavy chain CDR3 comprises amino acid residues 119 to 127 of SEQ ID NO:32;

d) a light chain variable region comprising CDR1, CDR2 and CDR3 of SEQ ID NO: 35 and having at least 90% sequence identity to the amino acid sequence of SEQ ID NO:35 and a heavy chain variable region comprising CDR1, CDR2 and CDR3 of SEQ ID NO: 36 and having at least 90% sequence identity to the amino acid sequence of SEQ ID NO:36, wherein (i) the light chain CDR1 comprises amino acid residues 44 to 54 of SEQ ID NO:35, (ii) the light chain CDR2 comprises amino acid residues 70 to 76 of SEQ ID NO:35 (Hi) the light chain CDR3 comprises amino acid residues 109 to 117 of SEQ ID NO:35, (iv) the heavy chain CDR1 comprises amino acid residues 45 to 54 of SEQ ID NO:36, (v) the heavy chain CDR2 comprises amino acid residues 69 to 87 of SEQ ID NO:36, and (vi) the heavy chain CDR3 comprises amino acid residues 120 to 127 of SEQ ID NO:36; or e) a light chain variable region comprising CDR1, CDR2 and CDR3 of SEQ ID NO: 39 and having at least 90% sequence identity to the amino acid sequence of SEQ ID NO:39 and a heavy chain variable region comprising CDR1, CDR2 and CDR3 of SEQ ID NO: 40 and having at least 90% sequence identity to the amino acid sequence of SEQ ID NO:40, wherein (i) the light chain CDR1 comprises amino acid residues 44 to 54 of SEQ ID NO:39, (ii) the light chain CDR2 comprises amino acid residues 70 to 76 of SEQ ID NO:39, (iii) the light chain CDR3 comprises amino acid residues 109 to 117 of SEQ ID NO:39, (iv) the heavy chain CDR1 comprises amino acid residues 44 to 54 of SEQ ID NO:40, (v) the heavy chain CDR2 comprises amino acid residues 69 to 84 of SEQ ID NO:40, and (vi) the heavy chain CDR3 sequence comprising amino acid residues 120 to 127 of SEQ ID NO:40.

2. The isolated antibody or the binding fragment thereof of claim 1, wherein the light chain variable region has at least 95% sequence identity to the amino acid sequence of SEQ ID NO:11 and the heavy chain variable region has at least 95% sequence identity to the amino acid sequence of SEQ ID NO:12.

3. The isolated antibody or the binding fragment thereof of claim 1, wherein the light chain variable region has at least 95% sequence identity to the amino acid sequence of SEQ ID NO:15 and the heavy chain variable region has at least 95% sequence identity to the amino acid sequence of SEQ ID NO:16.

4. The isolated antibody or the binding fragment thereof of claim 1, wherein the light chain variable region has at least 95% sequence identity to the amino acid sequence of SEQ ID NO:31 and the heavy chain variable region has at least 95% sequence identity to the amino acid sequence of SEQ ID NO:32.

5. The isolated antibody or the binding fragment thereof of claim 1, wherein the light chain variable region has at least 95% sequence identity to the amino acid sequence of SEQ ID NO:35 and the heavy chain variable region has at least 95% sequence identity to the amino acid sequence of SEQ ID NO:36.

6. The isolated antibody or the binding fragment thereof of claim 1, wherein the light chain variable region has at least 95% sequence identity to the amino acid sequence of SEQ ID NO:39 and the heavy chain variable region has at least 95% sequence identity to the amino acid sequence of SEQ ID NO:40.

7. The isolated antibody or the binding fragment thereof of claim 1, wherein the binding fragment is selected from the group of fragments consisting of Fv, F(ab'), F(ab')2, scFv, minibody and diabody fragments.

8. The isolated antibody or the binding fragment thereof of claim 1, wherein the antibody is a monoclonal antibody.

9. An assay kit comprising the isolated antibody or the binding fragment thereof of claim 1.

10. An assay device comprising a lateral flow assay device and the isolated antibody or the binding fragment thereof of claim 1, wherein the isolated antibody or the binding fragment is disposed on the lateral flow assay device.

11. The assay device of claim 10, wherein the assay device is a porous lateral flow assay device.

12. The assay device of claim 10, wherein the assay device is a non-porous lateral flow assay device.

13. A method of detecting olanzapine in a sample, the method comprising:
(i) contacting the sample with the isolated antibody or the binding fragment thereof of claim 1 labeled with a detectable marker, wherein the labeled antibody or the labeled binding fragment thereof and olanzapine present in the sample form a labeled complex; and
(ii) detecting the labeled complex, thereby detecting olanzapine in the sample.

14. A competitive immunoassay method for detecting olanzapine in a sample, the method comprising:
(i) contacting the sample with the isolated antibody or the binding fragment thereof of claim 1, and with olanzapine or a competitive binding partner of olanzapine, wherein one of the isolated antibody or the binding fragment thereof and the olanzapine or the competitive binding partner thereof is labeled with a detectable marker, wherein olanzapine in the sample competes with the olanzapine or the competitive binding partner thereof for binding to the isolated antibody or the binding fragment to foam a complex;
(ii) detecting the amount of the detectable marker bound to the complex; and
(iii) determining the amount of olanzapine in the sample based on the amount of bound detectable marker.

15. The method of claim 13 or 14, further comprising detecting the presence of one or more analytes in addition to olanzapine.

16. The method of claim 15, wherein the one or more analytes are anti-psychotic drugs other than olanzapine.

17. The method of claim 16, wherein the anti-psychotic drugs other than olanzapine are selected from the group consisting of: risperidone, paliperidone, quetiapine, aripiprazole, and metabolites thereof.

18. The method of claim 14, wherein the olanzapine or the competitive binding partner thereof is labeled with the detectable marker.

19. The method of claim 14, wherein the isolated antibody or the binding fragment thereof is labeled with the detectable marker.

20. The method of claim 14, wherein the immunoassay is performed on a lateral flow assay device and the sample is applied to the device.

* * * * *

SEQUENCE LISTING

<160> NUMBER OF SEQ ID NOS: 56

<210> SEQ ID NO 1
<211> LENGTH: 399
<212> TYPE: DNA
<213> ORGANISM: Artificial Sequence
<220> FEATURE:
<223> OTHER INFORMATION: Antibody Sequence

<400> SEQUENCE: 1

```
atggaatcac agactcaggt cctcatgtcc ctgctgctct ggatatctgg tacctatggg      60
gacattgtga tgacacagtc tccatcctcc ctgagtgtgg caacaggaga taaggtcact     120
atgagctgca gtccagtca gagtctgttc aacagtagaa accaaaagag ctacttggcc     180
tggtaccagc agaagccatg gcagcctcct aaactgctga tctacggggc atccactagg     240
gaatctgggg tccctgatcg cttcacaggc agtggatctg gaacagattt cactctcacc     300
atcagcagtg tgcaggctga agacctggca atttattact gtcagaatga ttatagttat     360
ccattcacgt tcggcacggg gacaaaattg gaaataaga                           399
```

<210> SEQ ID NO 2
<211> LENGTH: 399
<212> TYPE: DNA
<213> ORGANISM: Artificial Sequence
<220> FEATURE:
<223> OTHER INFORMATION: Antibody Sequence

<400> SEQUENCE: 2

```
atgggattca gcaggatctt tctcttcctc ctgtcagtaa ctacaggtgt ccactcccag      60
gcttttctac aacaatctgg ggctgagctg gtgaggcctg gggcctcagt gaagatgtcc     120
tgcaaggcct ctggctccac atttaccagt tacaatatac actgggtcaa gcagacacct     180
agacagggcc tggaatggat tggagctatt tatccaggaa atggtgatac ttcctacaat     240
cagaagttca gggcagggc cacactgact atagacaaat cctccagcac agcctacatg     300
cagctcagca gcctgacatc tgaagactct gcggtctatt tctgtgctaa ctggggcttt     360
gagtactggg gtcaaggcac cactctctca gtctcctca                           399
```

<210> SEQ ID NO 3
<211> LENGTH: 133
<212> TYPE: PRT
<213> ORGANISM: Artificial Sequence
<220> FEATURE:
<223> OTHER INFORMATION: Antibody Sequence

<400> SEQUENCE: 3

Met Glu Ser Gln Thr Gln Val Leu Met Ser Leu Leu Trp Ile Ser
1               5                   10                  15

Gly Thr Tyr Gly Asp Ile Val Met Thr Gln Ser Pro Ser Ser Leu Ser
                20                  25                  30

Val Ala Thr Gly Asp Lys Val Thr Met Ser Cys Lys Ser Ser Gln Ser
            35                  40                  45

Leu Phe Asn Ser Arg Asn Gln Lys Ser Tyr Leu Ala Trp Tyr Gln Gln
    50                  55                  60

Lys Pro Trp Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Ile Tyr

```
              100                 105                 110
Tyr Cys Gln Asn Asp Tyr Ser Tyr Pro Phe Thr Phe Gly Thr Gly Thr
        115                 120                 125

Lys Leu Glu Ile Arg
        130

<210> SEQ ID NO 4
<211> LENGTH: 133
<212> TYPE: PRT
<213> ORGANISM: Artificial Sequence
<220> FEATURE:
<223> OTHER INFORMATION: Antibody Sequence

<400> SEQUENCE: 4

Met Gly Phe Ser Arg Ile Phe Leu Phe Leu Leu Ser Val Thr Thr Gly
1               5                   10                  15

Val His Ser Gln Ala Phe Leu Gln Gln Ser Gly Ala Glu Leu Val Arg
            20                  25                  30

Pro Gly Ala Ser Val Lys Met Ser Cys Lys Ala Ser Gly Ser Thr Phe
        35                  40                  45

Thr Ser Tyr Asn Ile His Trp Val Lys Gln Thr Pro Arg Gln Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Arg Ala Thr Leu Thr Ile Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Asn Trp Gly Phe Glu Tyr Trp Gly Gln Gly Thr Thr
        115                 120                 125

Leu Ser Val Ser Ser
        130

<210> SEQ ID NO 5
<211> LENGTH: 399
<212> TYPE: DNA
<213> ORGANISM: Artificial Sequence
<220> FEATURE:
<223> OTHER INFORMATION: Antibody Sequence

<400> SEQUENCE: 5
atggaatcac agactcaggt cctcatgtcc ctgctgctct ggatatctgg tacctatggg      60
gacattgtga tgacacagtc tccatcctcc ctgagtgtgg caacaggaga taaggtcact     120
atgagctgca gtccagtca gagtctgttc aacagtagaa accaaaagag ctacttggcc      180
tggtaccagc agaagccatg gcagcctcct aaactgctga tctacggggc atccactagg     240
gaatctgggg tccctgatcg cttcacaggc agtggatctg gaacagattt cactctcacc     300
atcagcagtg tgcaggctga agacctggca atttattact gtcagaatga ttatagttat     360
ccattcacgt tcggcacggg gacaaaattg gaaataaga                            399

<210> SEQ ID NO 6
<211> LENGTH: 399
<212> TYPE: DNA
<213> ORGANISM: Artificial Sequence
<220> FEATURE:
<223> OTHER INFORMATION: Antibody Sequence

<400> SEQUENCE: 6
```

```
atgggattca gcaggatctt tctcttcctc ctgtcagtaa ctacaggtgt ccactcccag    60
gcttttctac aacaatctgg ggctgagctg gtgaggcctg gggcctcagt gaagatgtcc   120
tgcaaggcct ctggctccac atttaccagt tacaatatac actgggtcaa gcagacacct   180
agacagggcc tggaatggat tggagctatt tatccaggaa atggtgatac ttcctacaat   240
cagaagttca aggcagggc cacactgact atagacaaat cctccagcac agcctacatg   300
cagctcagca gcctgacatc tgaagactct gcggtctatt tctgtgctaa ctggggcttt   360
gagtactggg gtcaaggcac cactctctca gtctcctca                           399
```

<210> SEQ ID NO 7
<211> LENGTH: 133
<212> TYPE: PRT
<213> ORGANISM: Artificial Sequence
<220> FEATURE:
<223> OTHER INFORMATION: Antibody Sequence

<400> SEQUENCE: 7

```
Met Glu Ser Gln Thr Gln Val Leu Met Ser Leu Leu Trp Ile Ser
1               5                   10                  15

Gly Thr Tyr Gly Asp Ile Val Met Thr Gln Ser Pro Ser Ser Leu Ser
            20                  25                  30

Val Ala Thr Gly Asp Lys Val Thr Met Ser Cys Lys Ser Ser Gln Ser
        35                  40                  45

Leu Phe Asn Ser Arg Asn Gln Lys Ser Tyr Leu Ala Trp Tyr Gln Gln
    50                  55                  60

Lys Pro Trp Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Ile Tyr
            100                 105                 110

Tyr Cys Gln Asn Asp Tyr Ser Tyr Pro Phe Thr Phe Gly Thr Gly Thr
        115                 120                 125

Lys Leu Glu Ile Arg
    130
```

<210> SEQ ID NO 8
<211> LENGTH: 133
<212> TYPE: PRT
<213> ORGANISM: Artificial Sequence
<220> FEATURE:
<223> OTHER INFORMATION: Antibody Sequence

<400> SEQUENCE: 8

```
Met Gly Phe Ser Arg Ile Phe Leu Phe Leu Leu Ser Val Thr Thr Gly
1               5                   10                  15

Val His Ser Gln Ala Phe Leu Gln Gln Ser Gly Ala Glu Leu Val Arg
            20                  25                  30

Pro Gly Ala Ser Val Lys Met Ser Cys Lys Ala Ser Gly Ser Thr Phe
        35                  40                  45

Thr Ser Tyr Asn Ile His Trp Val Lys Gln Thr Pro Arg Gln Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Arg Ala Thr Leu Thr Ile Asp Lys Ser Ser Ser
                85                  90                  95
```

Thr Ala Tyr Met Gln Leu Ser Ser Leu Thr Ser Glu Asp Ser Ala Val
            100                 105                 110

Tyr Phe Cys Ala Asn Trp Gly Phe Glu Tyr Trp Gly Gln Gly Thr Thr
        115                 120                 125

Leu Ser Val Ser Ser
    130

<210> SEQ ID NO 9
<211> LENGTH: 381
<212> TYPE: DNA
<213> ORGANISM: Artificial Sequence
<220> FEATURE:
<223> OTHER INFORMATION: Antibody Sequence

<400> SEQUENCE: 9
atggagtcac agactcaggt ctttgtattc gtgttgctct ggttgtctgg tggagatgga        60
gacattgtga tgacccagtc tcaaaaattc atgtccacat cactaggaga cagggtcagc       120
atcacctgca aggccagtca gaatgtggga atttatgttt cctggtatca acagaaacca       180
gggaaatctc ctaaagcact aatttactgg tcttcaaacc ggttcactgg agtccctgat       240
cgtttcacag gcagtggatc tgggacagac ttcactctca ccatcaccga tgtgcagtct       300
gaagacttgg cagattattt ctgtgagcaa tatagcagcg atccgtatac gttcggatcg       360
gggaccaagc tggaaataaa a                                                 381

<210> SEQ ID NO 10
<211> LENGTH: 399
<212> TYPE: DNA
<213> ORGANISM: Artificial Sequence
<220> FEATURE:
<223> OTHER INFORMATION: Antibody Sequence

<400> SEQUENCE: 10
atggaaagac actggatctt tctcttcctg ttgtcagtaa ctgcaggtgt ccactcccag        60
gtccaactgc agcagtctgc ggctgaactg gcaagacctg ggcctcagt gaagatgtcc       120 tgcaagactt ctggctacac cttcactagc gaccggatgc actgggtaat acagaggcct       180
ggacagggtc tggagtggat tggatacatt cttcctagaa atgtttatac taaatacaat       240
aaaaagttca aggacaaggc acattgact gcagacacat cctccagtat agcctacatc       300
caactgagca gcctgacatc tgaagactct gcagtctatt actgtgtaaa gtctgacggg       360
ggctactggg gccaaggcac cactctcaca gtctcctca                              399

<210> SEQ ID NO 11
<211> LENGTH: 127
<212> TYPE: PRT
<213> ORGANISM: Artificial Sequence
<220> FEATURE:
<223> OTHER INFORMATION: Antibody Sequence

<400> SEQUENCE: 11

Met Glu Ser Gln Thr Gln Val Phe Val Phe Val Leu Leu Trp Leu Ser
1               5                   10                  15

Gly Gly Asp Gly Asp Ile Val Met Thr Gln Ser Gln Lys Phe Met Ser
            20                  25                  30

Thr Ser Leu Gly Asp Arg Val Ser Ile Thr Cys Lys Ala Ser Gln Asn
        35                  40                  45

Val Gly Ile Tyr Val Ser Trp Tyr Gln Gln Lys Pro Gly Lys Ser Pro
    50                  55                  60

Lys Ala Leu Ile Tyr Trp Ser Ser Asn Arg Phe Thr Gly Val Pro Asp
65                  70                  75                  80

Arg Phe Thr Gly Ser Gly Ser Gly Thr Asp Phe Thr Leu Thr Ile Thr
                85                  90                  95

Asp Val Gln Ser Glu Asp Leu Ala Asp Tyr Phe Cys Glu Gln Tyr Ser
            100                 105                 110

Ser Asp Pro Tyr Thr Phe Gly Ser Gly Thr Lys Leu Glu Ile Lys
        115                 120                 125

<210> SEQ ID NO 12
<211> LENGTH: 133
<212> TYPE: PRT
<213> ORGANISM: Artificial Sequence
<220> FEATURE:
<223> OTHER INFORMATION: Antibody Sequence

<400> SEQUENCE: 12

Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
            20                  25                  30

Pro Gly Ala Ser Val Lys Met Ser Cys Lys Thr Ser Gly Tyr Thr Phe
        35                  40                  45

Thr Ser Asp Arg Met His Trp Val Ile Gln Arg Pro Gly Gln Gly Leu
    50                  55                  60

Glu Trp Ile Gly Tyr Ile Leu Pro Arg Asn Val Tyr Thr Lys Tyr Asn
65                  70                  75                  80

Lys Lys Phe Lys Asp Lys Ala Thr Leu Thr Ala Asp Thr Ser Ser Ser
                85                  90                  95

Ile Ala Tyr Ile Gln Leu Ser Ser Leu Thr Ser Glu Asp Ser Ala Val
            100                 105                 110

Tyr Tyr Cys Val Lys Ser Asp Gly Gly Tyr Trp Gly Gln Gly Thr Thr
        115                 120                 125

Leu Thr Val Ser Ser
    130

<210> SEQ ID NO 13
<211> LENGTH: 381
<212> TYPE: DNA
<213> ORGANISM: Artificial Sequence
<220> FEATURE:
<223> OTHER INFORMATION: Antibody Sequence

<400> SEQUENCE: 13
atggagtcac agactcaggt ctttgtattc gtgttgctct ggttgtctgg tggtgatgga      60
gacattgtga tgacccagtc tcaaaaattc atgtccacat cactaggaga cagggtcagc     120
atcacctgca aggccagtca gaatgtggga atttatgtat cctggtatca acagaaacca     180
gggaaatctc ctaaagcact aatttattgg catcaaaacc ggttcactgg agtccctgat     240
cgcttcacag gcagtggatc tgggacagac ttcactctca ccatcaccaa tgtgcagtct     300
gaagacttgg cagatatttt ctgtgaacaa tatagcagcg atccgtatac gttcggatcg     360
gggaccaagc tagaaataaa a                                                 381

<210> SEQ ID NO 14
<211> LENGTH: 399
<212> TYPE: DNA
<213> ORGANISM: Artificial Sequence
<220> FEATURE:

<223> OTHER INFORMATION: Antibody Sequence

<400> SEQUENCE: 14

```
atggaaaggc actggatctt tctcttcctg ttgtcagtaa ctgcaggtgt ccactcccag     60
gtccaactgc agcagtctgc ggctgaactg gtaagacctg gggcctcagt gaagatgtcc    120
tgcaagactt ctggctacat cttcactagc gaccggatgc actgggtaaa acagaggcct    180
ggacagggtc tggagtggat tggatacatt attcctagaa attttttatac taaatacaat   240
cagaaattca aggacaaggc cacattgact gcagacacat cctccaatac agcctacatg    300
cagttgagca gcctgacatc tgaagactct gcagtctatt actgtgtgaa atctgacggg    360
gcctactggg gccaaggcac cactctcaca gtctcctca                           399
```

<210> SEQ ID NO 15
<211> LENGTH: 127
<212> TYPE: PRT
<213> ORGANISM: Artificial Sequence
<220> FEATURE:
<223> OTHER INFORMATION: Antibody Sequence

<400> SEQUENCE: 15

```
Met Glu Ser Gln Thr Gln Val Phe Val Phe Val Leu Leu Trp Leu Ser
 1               5                  10                  15
Gly Gly Asp Gly Asp Ile Val Met Thr Gln Ser Gln Lys Phe Met Ser
            20                  25                  30
Thr Ser Leu Gly Asp Arg Val Ser Ile Thr Cys Lys Ala Ser Gln Asn
        35                  40                  45
Val Gly Ile Tyr Val Ser Trp Tyr Gln Gln Lys Pro Gly Lys Ser Pro
    50                  55                  60
Lys Ala Leu Ile Tyr Trp Ala Ser Asn Arg Phe Thr Gly Val Pro Asp
65                  70                  75                  80
Arg Phe Thr Gly Ser Gly Ser Gly Thr Asp Phe Thr Leu Thr Ile Thr
                85                  90                  95
Asn Val Gln Ser Glu Asp Leu Ala Glu Tyr Phe Cys Gln Gln Tyr Ser
            100                 105                 110
Ser Asp Pro Tyr Thr Phe Gly Ser Gly Thr Lys Leu Glu Ile Lys
        115                 120                 125
```

<210> SEQ ID NO 16
<211> LENGTH: 133
<212> TYPE: PRT
<213> ORGANISM: Artificial Sequence
<220> FEATURE:
<223> OTHER INFORMATION: Antibody Sequence

<400> SEQUENCE: 16

```
Met Glu Arg His Trp Ile Phe Leu Phe Leu Leu Ser Val Thr Ala Gly
 1               5                  10                  15
Val His Ser Gln Val Gln Leu Gln Gln Ser Ala Ala Glu Leu Val Arg
            20                  25                  30
Pro Gly Ala Ser Val Lys Met Ser Cys Lys Thr Ser Gly Tyr Ile Phe
        35                  40                  45
Thr Ser Asp Arg Met His Trp Val Lys Gln Arg Pro Gly Gln Gly Leu
    50                  55                  60
Glu Trp Ile Gly Tyr Ile Ile Pro Arg Asn Phe Tyr Thr Lys Tyr Asn
65                  70                  75                  80
Gln Lys Phe Lys Asp Lys Ala Thr Leu Thr Ala Asp Thr Ser Ser Asn
                85                  90                  95
```

Thr Ala Tyr Met Gln Leu Ser Ser Leu Thr Ser Glu Asp Ser Ala Val
                100                 105                 110

Tyr Tyr Cys Val Lys Ser Asp Gly Ala Tyr Trp Gly Gln Gly Thr Thr
            115                 120                 125

Leu Thr Val Ser Ser
        130

<210> SEQ ID NO 17
<211> LENGTH: 393
<212> TYPE: DNA
<213> ORGANISM: Artificial Sequence
<220> FEATURE:
<223> OTHER INFORMATION: Antibody Sequence

<400> SEQUENCE: 17
atgaagttgc ctgttaggct gttggtgctg atgttctgga ttcctgcttc cagtagtgat      60
gttgtgatga cccaaactcc actctccctg cctgtcagtc ttggagatca agcctccatc     120
tcttgttggt ctagtcagag ccttgtagac agttatggaa cacctatttt acattggtat     180
ctgcagaagc caggccagtc tccaaagctc ctgatctaca agtttccaac cgatttttct     240
ggggtcccag acaggttcag tggcagtgga tcagggacag atttcacact caagatcagc     300
agagtggagg ctgaggatct gggaatttac ttttgctctc aaactacata tgttccgtat     360
acgttcggat cggggaccaa gctggaaatg aaa                                  393

<210> SEQ ID NO 18
<211> LENGTH: 420
<212> TYPE: DNA
<213> ORGANISM: Artificial Sequence
<220> FEATURE:
<223> OTHER INFORMATION: Antibody Sequence

<400> SEQUENCE: 18
atggaatgga cctgggtctt tctcttcctc ctgtcagtaa ctgcaggtgt ccactcccag      60
gttcagctgc accagtctgg agctgagctg atgaagcctg gggcctcagt gaagatatcc     120
tgcaaggcta ccggctacac atttagtagg tactggatag agtggataaa acagaggcct     180
ggccatggcc ttgagtggat tggagagttt ctacctggaa gtggaaattc taactacaat     240
gctaaattca gggcaaggc caccttcact gcagcaacat cctccaacac agcctacatg     300
caactcagca gtgtgacatc tgaagactct gccgtctatt tctgtgcaac ctggtacgat     360
gttaactacc gctatcttat ggactattgg ggtcaaggaa cctcagtcac cgtctcctca     420

<210> SEQ ID NO 19
<211> LENGTH: 131
<212> TYPE: PRT
<213> ORGANISM: Artificial Sequence
<220> FEATURE:
<223> OTHER INFORMATION: Antibody Sequence

<400> SEQUENCE: 19

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Trp Ser Ser Gln Ser Leu
        35                  40                  45

Val Asp Ser Tyr Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
            85                  90                  95

Leu Lys Ile Ser Arg Val Glu Ala Glu Asp Leu Gly Ile Tyr Phe Cys
        100                 105                 110

Ser Gln Thr Thr Tyr Val Pro Tyr Thr Phe Gly Ser Gly Thr Lys Leu
    115                 120                 125

Glu Met Lys
    130

<210> SEQ ID NO 20
<211> LENGTH: 140
<212> TYPE: PRT
<213> ORGANISM: Artificial Sequence
<220> FEATURE:
<223> OTHER INFORMATION: Antibody Sequence

<400> SEQUENCE: 20

Met Glu Trp Thr Trp Val Phe Leu Phe Leu Leu Ser Val Thr Ala Gly
1               5                   10                  15

Val His Ser Gln Val Gln Leu His Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Arg Tyr Trp Ile Glu Trp Ile Lys Gln Arg Pro Gly His Gly Leu
    50                  55                  60

Glu Trp Ile Gly Glu Phe Leu Pro Gly Ser Gly Asn Ser Asn Tyr Asn
65                  70                  75                  80

Ala Lys Phe Lys Gly Lys Ala Thr Phe Thr Ala Ala Thr Ser Ser Asn
            85                  90                  95

Thr Ala Tyr Met Gln Leu Ser Ser Val Thr Ser Glu Asp Ser Ala Val
        100                 105                 110

Tyr Phe Cys Ala Thr Trp Tyr Asp Val Asn Tyr Arg Tyr Leu Met Asp
    115                 120                 125

Tyr Trp Gly Gln Gly Thr Ser Val Thr Val Ser Ser
130                 135                 140

<210> SEQ ID NO 21
<211> LENGTH: 393
<212> TYPE: DNA
<213> ORGANISM: Artificial Sequence
<220> FEATURE:
<223> OTHER INFORMATION: Antibody Sequence

<400> SEQUENCE: 21
atgaagttgc ctgttaggct gttggtgctg atgttctgga ttcctgcttc cagcagtgat      60
attgtgatga cccaaactcc actctccctg cctgtcagtc ttggagatca agcctccatc     120
tcttgcaggt ctagtcagag ccttgtacgc agtaatggga cacctatttt acattggtac     180
ctgcagaagc caggccagtc tccaaagctc ctgatctaca agtttccaa ccgattttct     240 ggggtccccg acaggttcag tggcagtgga tcagggacag atttcacact caagatcagc     300
agagtggagg ctgaggatct gggagtttat ttctgctctc aaagtacaca tgttccgtat     360
acgttcggat cggggaccaa gctggaaata aaa                                  393

<210> SEQ ID NO 22

-continued

<211> LENGTH: 420
<212> TYPE: DNA
<213> ORGANISM: Artificial Sequence
<220> FEATURE:
<223> OTHER INFORMATION: Antibody Sequence

<400> SEQUENCE: 22
atggaatgga cctgggtctt tctcttcctc ctgtcagtaa ccgcaggtgt ccactcccag    60
gttcagctgc agcagtctgg agctgtactg atgaagcctg gggcctcagt gaagatatcc   120
tgcaaggcta ctggctacac attcattagg tactggatag agtgggtaaa gaagaggcct   180
ggacatggcc ttgactggat tggagaaatt ttacctggaa gtggaagttc taactacaat   240
gagaacttca aggtcaaggc cactttcact gtagatactt cctccaacac agcctacatg   300
caactcaaca gcctgacatc tcaggactct gccgtctatt actgtgcaat ttggtacgat   360
ggtaattacc gctctcttat ggactactgg ggtcaaggaa cctcagtcac cgtctcctca   420

<210> SEQ ID NO 23
<211> LENGTH: 131
<212> TYPE: PRT
<213> ORGANISM: Artificial Sequence
<220> FEATURE:
<223> OTHER INFORMATION: Antibody Sequence

<400> SEQUENCE: 23

Met Lys Leu Pro Val Arg Leu Leu Val Leu Met Phe Trp Ile Pro Ala
1               5                   10                  15

Ser Ser Ser Asp Ile Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val Arg Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Ser Gly Thr Lys Leu
        115                 120                 125

Glu Ile Lys
    130

<210> SEQ ID NO 24
<211> LENGTH: 140
<212> TYPE: PRT
<213> ORGANISM: Artificial Sequence
<220> FEATURE:
<223> OTHER INFORMATION: Antibody Sequence

<400> SEQUENCE: 24

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Val Leu Met Lys
            20                  25                  30

Pro Gly Ala Ser Val Lys Ile Ser Cys Lys Ala Thr Gly Tyr Thr Phe
        35                  40                  45

Ile Arg Tyr Trp Ile Glu Trp Val Lys Lys Arg Pro Gly His Gly Leu

```
                 50                  55                  60
Asp Trp Ile Gly Glu Ile Leu Pro Gly Ser Gly Ser Ser Asn Tyr Asn
 65                  70                  75                  80

Glu Asn Phe Lys Val Lys Ala Thr Phe Thr Val Asp Thr Ser Ser Asn
                 85                  90                  95

Thr Ala Tyr Met Gln Leu Asn Ser Leu Thr Ser Gln Asp Ser Ala Val
                100                 105                 110

Tyr Tyr Cys Ala Ile Trp Tyr Asp Gly Asn Tyr Arg Ser Leu Met Asp
            115                 120                 125

Tyr Trp Gly Gln Gly Thr Ser Val Thr Val Ser Ser
        130                 135                 140

<210> SEQ ID NO 25
<211> LENGTH: 393
<212> TYPE: DNA
<213> ORGANISM: Artificial Sequence
<220> FEATURE:
<223> OTHER INFORMATION: Antibody Sequence

<400> SEQUENCE: 25
atgaagttgc ctgttaggct gttggtgctg atgttctgga ttcctgcttc cagcagtgat      60
attgtgatga cccaaactcc actctccctg cctgtcagtc ttggagatca agcctccatc     120
tcttgcaggt ctagtcagag ccttgtacgc agtaatggaa acacctattt acattggtac     180
ctgcagaagc caggccagtc tccaaagctc ctgatctaca agtttccaa ccgatttttct     240 ggggtccccg acaggttcag tgcagtggga tcaggacag atttcacact caagatcagc     300
agagtggagg ctgaggatct gggagtttat ttctgctctc aaagtacaca tgttccgtat     360
acgttcggat cggggaccaa gctggaaata aaa                                  393

<210> SEQ ID NO 26
<211> LENGTH: 420
<212> TYPE: DNA
<213> ORGANISM: Artificial Sequence
<220> FEATURE:
<223> OTHER INFORMATION: Antibody Sequence

<400> SEQUENCE: 26
atggaatgga cctgggtctt tctcttcctc ctgtcagtaa ccgcaggtgt ccactcccag      60
gttcagctgc agcagtctgg agctgtactg atgaagcctg ggcctcagt gaagatatcc     120 tgcaaggcta ctggctacac attcattagg tactggatag agtgggtaaa gaagaggcct     180
ggacatggcc ttgactggat tggagaaatt ttacctggaa gtggaagttc taactacaat     240
gagaacttca aggtcaaggc cactttcact gtagatactt cctccaacac agcctacatg     300
caactcaaca gcctgacatc tcaggactct gccgtctatt actgtgcaat tggtacgat     360 ggtaattacc gctctcttat ggactactgg ggtcaaggaa cctcagtcac cgtctcctca     420

<210> SEQ ID NO 27
<211> LENGTH: 131
<212> TYPE: PRT
<213> ORGANISM: Artificial Sequence
<220> FEATURE:
<223> OTHER INFORMATION: Antibody Sequence

<400> SEQUENCE: 27

Met Lys Leu Pro Val Arg Leu Leu Val Leu Met Phe Trp Ile Pro Ala
  1               5                  10                  15

Ser Ser Ser Asp Ile Val Met Thr Gln Thr Pro Leu Ser Leu Pro Val
```

Ser Leu Gly Asp Gln Ala Ser Ile Ser Cys Arg Ser Ser Gln Ser Leu
            35                  40                  45

Val Arg Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Ser Gly Thr Lys Leu
        115                 120                 125

Glu Ile Lys
    130

<210> SEQ ID NO 28
<211> LENGTH: 140
<212> TYPE: PRT
<213> ORGANISM: Artificial Sequence
<220> FEATURE:
<223> OTHER INFORMATION: Antibody Sequence

<400> SEQUENCE: 28

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Val Leu Met Lys
            20                  25                  30

Pro Gly Ala Ser Val Lys Ile Ser Cys Lys Ala Thr Gly Tyr Thr Phe
        35                  40                  45

Ile Arg Tyr Trp Ile Glu Trp Val Lys Lys Arg Pro Gly His Gly Leu
    50                  55                  60

Asp Trp Ile Gly Glu Ile Leu Pro Gly Ser Gly Ser Ser Asn Tyr Asn
65                  70                  75                  80

Glu Asn Phe Lys Val Lys Ala Thr Phe Thr Val Asp Thr Ser Ser Asn
                85                  90                  95

Thr Ala Tyr Met Gln Leu Asn Ser Leu Thr Ser Gln Asp Ser Ala Val
            100                 105                 110

Tyr Tyr Cys Ala Ile Trp Tyr Asp Gly Asn Tyr Arg Ser Leu Met Asp
        115                 120                 125

Tyr Trp Gly Gln Gly Thr Ser Val Thr Val Ser Ser
    130                 135                 140

<210> SEQ ID NO 29
<211> LENGTH: 381
<212> TYPE: DNA
<213> ORGANISM: Artificial Sequence
<220> FEATURE:
<223> OTHER INFORMATION: Antibody Sequence

<400> SEQUENCE: 29
atgagtgtgc ccactcaggt cctggcattg ctgctgctgt ggcttacaga tgccagatgt      60
gatatccaga tgactcagtc tccagcctcc ctatctgcat ctgtgggaga aactgtcacc     120
atcacatgtc gagcaagtgg gaatattcac aattatttag catggtatca gcagaaacag     180
ggaaaatctc ctcagctcct ggtctataat gcaaaaacct tagcggaagg tgtgccatca     240
aggttcagtg gcagtggatc aggaacacaa tattctctca agatcaacag cctgcagcct     300

```
gaggattttg ggacttatta ctgtcttcat tattacaata ttccgctcac gttcggtgct    360
gggaccacgc tggagctgaa a                                              381
```

<210> SEQ ID NO 30
<211> LENGTH: 414
<212> TYPE: DNA
<213> ORGANISM: Artificial Sequence
<220> FEATURE:
<223> OTHER INFORMATION: Antibody Sequence

<400> SEQUENCE: 30

```
atgagagtgc tgattctttt gtggctgttc acagcctttc ctggtttcct gtctgatgtg     60
cagcttcagg agtcaggacc tggcctggtg aaaccttctc agtctctgtc cgtcacctgc    120
actgtcactg gctactccat catcagtggt tattactgga actggatccg gcagtttcca    180
ggaaacaaac tggagtggct gggctccata cacaacagtg gtcgcactaa ctacaatcca    240
tctctcaaaa gtcgaatctc tatcagtcga gacacatcca agaaccaatt cttcctgcag    300
ctggattctg tgactactga ggacacagcc acatattact gtcacttggg ggacgatggt    360
acctactctg ctatggacta ctggggtcaa ggaacctcag tcaccgtctc ctca          414
```

<210> SEQ ID NO 31
<211> LENGTH: 127
<212> TYPE: PRT
<213> ORGANISM: Artificial Sequence
<220> FEATURE:
<223> OTHER INFORMATION: Antibody Sequence

<400> SEQUENCE: 31

```
Met Ser Val Pro Thr Gln Val Leu Ala Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Leu His Tyr Tyr
            100                 105                 110

Asn Ile Pro Leu Thr Phe Gly Ala Gly Thr Thr Leu Glu Leu Lys
        115                 120                 125
```

<210> SEQ ID NO 32
<211> LENGTH: 138
<212> TYPE: PRT
<213> ORGANISM: Artificial Sequence
<220> FEATURE:
<223> OTHER INFORMATION: Antibody Sequence

<400> SEQUENCE: 32

```
Met Arg Val Leu Ile Leu Leu Trp Leu Phe Thr Ala Phe Pro Gly Phe
1               5                   10                  15

Leu Ser Asp Val Gln Leu Gln Glu Ser Gly Pro Gly Leu Val Lys Pro
            20                  25                  30
```

Ser Gln Ser Leu Ser Val Thr Cys Thr Val Thr Gly Tyr Ser Ile Ile
            35                  40                  45

Ser Gly Tyr Tyr Trp Asn Trp Ile Arg Gln Phe Pro Gly Asn Lys Leu
 50                  55                  60

Glu Trp Leu Gly Ser Ile His Asn Ser Gly Arg Thr Asn Tyr Asn Pro
 65                  70                  75                  80

Ser Leu Lys Ser Arg Ile Ser Ile Ser Arg Asp Thr Ser Lys Asn Gln
                 85                  90                  95

Phe Phe Leu Gln Leu Asp Ser Val Thr Thr Glu Asp Thr Ala Thr Tyr
                100                 105                 110

Tyr Cys His Leu Gly Asp Asp Gly Thr Tyr Ser Ala Met Asp Tyr Trp
            115                 120                 125

Gly Gln Gly Thr Ser Val Thr Val Ser Ser
    130                 135

<210> SEQ ID NO 33
<211> LENGTH: 381
<212> TYPE: DNA
<213> ORGANISM: Artificial Sequence
<220> FEATURE:
<223> OTHER INFORMATION: Antibody Sequence

<400> SEQUENCE: 33
atgaggaccc ctgctcagtt tcttggaatc ttgttgctct ggtttccagg tatcaagtgt      60
gacatcaaga tgacccagtc tccatcttcc atgtatgcat ctctaggaga gagagtcact     120
atctcttgca aggcgagtca ggacattaat cgctatttaa gctggttcct gcagaaacca     180
gggaaatctc ctaagaccct gatctatcgt acaaacagat tagtagatgg ggtcccatca     240
aggttcagtg gcagtggatc tggacaagat tattctctca ccatcagcag cctggagtat     300
gaagatttgg gaatttatta ttgtctacat tatgctgagt ttcctcccac gttcggtgct     360
gggactaagc tggagctgaa a                                                381

<210> SEQ ID NO 34
<211> LENGTH: 414
<212> TYPE: DNA
<213> ORGANISM: Artificial Sequence
<220> FEATURE:
<223> OTHER INFORMATION: Antibody Sequence

<400> SEQUENCE: 34
atgtacttgg gactgaactg tgtattcata gttttttctct taaaaggtgt ccagagtgaa      60
gtgaaacttg aggagtctgg aggaggcttg gtacaacctg gaggatccat gaaactctcc     120
tgtgttgcct ctggattcat tttcagtaac tactggatgg actggatccg ccagtctcca     180
gagaagggac ttgagtgggt tgctcaaatt agattgagat ctaataatta tgcgacacat     240
tatgcggagt ctttgaaagg gaggttcacc atctcaagag atgattccaa agtactgtc      300 tacctgcaaa tgaacagttt aagaactgaa gactctggca tttattactg tacgaggact     360
atgattacga cacccagcta ctggggccaa ggcaccactc tcacagtctc ctca            414

<210> SEQ ID NO 35
<211> LENGTH: 127
<212> TYPE: PRT
<213> ORGANISM: Artificial Sequence
<220> FEATURE:
<223> OTHER INFORMATION: Antibody Sequence

<400> SEQUENCE: 35

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Thr Ile Ser Cys Lys Ala Ser Gln Asp
        35                  40                  45

Ile Asn Arg Tyr Leu Ser Trp Phe Leu Gln Lys Pro Gly Lys Ser Pro
    50                  55                  60

Lys Thr Leu Ile Tyr Arg Thr Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Leu Gly Ile Tyr Tyr Cys Leu His Tyr Ala
            100                 105                 110

Glu Phe Pro Pro Thr Phe Gly Ala Gly Thr Lys Leu Glu Leu Lys
        115                 120                 125

<210> SEQ ID NO 36
<211> LENGTH: 138
<212> TYPE: PRT
<213> ORGANISM: Artificial Sequence
<220> FEATURE:
<223> OTHER INFORMATION: Antibody Sequence

<400> SEQUENCE: 36

Met Tyr Leu Gly Leu Asn Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Ile Phe
        35                  40                  45

Ser Asn Tyr Trp Met Asp Trp Ile Arg Gln Ser Pro Glu Lys Gly Leu
    50                  55                  60

Glu Trp Val Ala Gln Ile Arg Leu Arg Ser Asn Asn Tyr Ala Thr His
65                  70                  75                  80

Tyr Ala Glu Ser Leu Lys Gly Arg Phe Thr Ile Ser Arg Asp Asp Ser
                85                  90                  95

Lys Ser Thr Val Tyr Leu Gln Met Asn Ser Leu Arg Thr Glu Asp Ser
            100                 105                 110

Gly Ile Tyr Tyr Cys Thr Arg Thr Met Ile Thr Thr Pro Ser Tyr Trp
        115                 120                 125

Gly Gln Gly Thr Thr Leu Thr Val Ser Ser
    130                 135

<210> SEQ ID NO 37
<211> LENGTH: 381
<212> TYPE: DNA
<213> ORGANISM: Artificial Sequence
<220> FEATURE:
<223> OTHER INFORMATION: Antibody Sequence

<400> SEQUENCE: 37
atgagtgtgc ccactcaggt cctggcattg ctgctgctgt ggcttacaga tgccagatgt    60
gatatccaga tgactcagtc tccagcctcc ctatctgcat ctgtgggaga aactgtcacc   120
atcacatgtc gagcaagtgg gaatattcac aattatttag catggtatca gcagaaacag   180
ggaaaatctc ctcagctcct ggtctataat acaaaatcct tggcggaagg tgtgccatca   240

```
aggttcagtg gcagtggatc aggaacacaa tattctctca agatctacag cctgcagcct    300
gcggattttg ggcttatta ctgtcttcat tattataata ctccgctcac tttcggtgct    360
gggaccaagc tagagctgag a                                              381
```

<210> SEQ ID NO 38
<211> LENGTH: 414
<212> TYPE: DNA
<213> ORGANISM: Artificial Sequence
<220> FEATURE:
<223> OTHER INFORMATION: Antibody Sequence

<400> SEQUENCE: 38

```
atgagagtgc tgattctttt gtggctgttc acagcctttc ctggtatcct gtctgatgtg     60
cagcttcagg agtcaggacc tggcctggtg aaaccttctc agtctctgtc cgtcacctgc    120
actgtcactg gcttctccat caccagtggt tattactgga actggatccg gcagtttcca    180
ggaaacaaac tggagtggat gggctacata cacaacagtg gtcgcactaa ctacaatcca    240
tctctcaaaa gtcgaatctc tatcactcga gacacatcca aaaaccagtt cttcctgcag    300
ttgagttctg tgactaatgc ggacacagcc acatattact gtcacttggg ggacgatggt    360
acctcctatg ctatggacta ctggggtcaa ggaacctcag tcaccgtctc ctca          414
```

<210> SEQ ID NO 39
<211> LENGTH: 127
<212> TYPE: PRT
<213> ORGANISM: Artificial Sequence
<220> FEATURE:
<223> OTHER INFORMATION: Antibody Sequence

<400> SEQUENCE: 39

```
Met Ser Val Pro Thr Gln Val Leu Ala Leu Leu Leu Leu Trp Leu Thr
1               5                   10                  15

Asp Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
            35                  40                  45

Ile His Asn Tyr Leu Ala Trp Tyr Gln Gln Lys Gln Gly Lys Ser Pro
        50                  55                  60

Gln Leu Leu Val Tyr Asn Thr Lys Ser Leu Ala Glu Gly Val Pro Ser
65                  70                  75                  80

Arg Phe Ser Gly Ser Gly Ser Gly Thr Gln Tyr Ser Leu Lys Ile Tyr
                85                  90                  95

Ser Leu Gln Pro Ala Asp Phe Gly Ala Tyr Tyr Cys Leu His Tyr Tyr
            100                 105                 110

Asn Thr Pro Leu Thr Phe Gly Ala Gly Thr Lys Leu Glu Leu Arg
        115                 120                 125
```

<210> SEQ ID NO 40
<211> LENGTH: 138
<212> TYPE: PRT
<213> ORGANISM: Artificial Sequence
<220> FEATURE:
<223> OTHER INFORMATION: Antibody Sequence

<400> SEQUENCE: 40

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30
```

```
Ser Gln Ser Leu Ser Val Thr Cys Thr Val Thr Gly Phe Ser Ile Thr
         35                  40                  45

Ser Gly Tyr Tyr Trp Asn Trp Ile Arg Gln Phe Pro Gly Asn Lys Leu
     50                  55                  60

Glu Trp Met Gly Tyr Ile His Asn Ser Gly Arg Thr Asn Tyr Asn Pro
 65              70                  75                  80

Ser Leu Lys Ser Arg Ile Ser Ile Thr Arg Asp Thr Ser Lys Asn Gln
                 85                  90                  95

Phe Phe Leu Gln Leu Ser Ser Val Thr Asn Ala Asp Thr Ala Thr Tyr
             100                 105                 110

Tyr Cys His Leu Gly Asp Asp Gly Thr Ser Tyr Ala Met Asp Tyr Trp
         115                 120                 125

Gly Gln Gly Thr Ser Val Thr Val Ser Ser
         130                 135
```

<210> SEQ ID NO 41
<211> LENGTH: 384
<212> TYPE: DNA
<213> ORGANISM: Artificial Sequence
<220> FEATURE:
<223> OTHER INFORMATION: Antibody Sequence

<400> SEQUENCE: 41

```
atggattttc aggtgcagat tttcagcttc ctgctaatca gtgcctcagt catactgtcc      60
agaggacaaa ttgttctcac ccagtctcca gcaatcatgt ctgcatctct gggggaggag     120
atcaccctaa cctgcagtgc cagctcgagt gtaaattaca tgcactggta ccagcagaag     180
tcaggcactt ctcccaaact cttgatttat agcacatcca acctggcttc tggagtccct     240
tctcgcttca gtggcagtgg gtctgggacc ttttattctc tcacaatcag cagtgtggag     300
gctgaagatg ctgccgatta ttactgccat cagtggagta gttatccgta cacgttcgga     360
gggggaccaa gctggaaat aaaa                                              384
```

<210> SEQ ID NO 42
<211> LENGTH: 408
<212> TYPE: DNA
<213> ORGANISM: Artificial Sequence
<220> FEATURE:
<223> OTHER INFORMATION: Antibody Sequence

<400> SEQUENCE: 42

```
atggaatgga gttggatatt tctctttctc ctgtcaggaa ctgcaggtgt ccactctgag      60
gtccagttgc agcagtctgg acctgagctg gtaaagcctg ggcttcagt gaagatgtcc     120
tgcaaggctt ctggatacac attcactaac tatgttattt actgggtgaa gcagaagcct     180
gggcagggcc ttgagtggat tggatatatt aatccttaca tgatggtac taagtacaat     240
gagaagttca aggcaaggc cacactgact gcagacaaat cctccagcac agcctacatg     300
gagctcagta gcctgacctc tgaggactct gcggtctatt actgtgcctg taacttcctc     360
tatgctatgg actactgggg tcaaggaacc tcagtcaccg tctcctca                  408
```

<210> SEQ ID NO 43
<211> LENGTH: 128
<212> TYPE: PRT
<213> ORGANISM: Artificial Sequence
<220> FEATURE:
<223> OTHER INFORMATION: Antibody Sequence

<400> SEQUENCE: 43

Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
                20                  25                  30

Met Ser Ala Ser Leu Gly Glu Glu Ile Thr Leu Thr Cys Ser Ala Ser
            35                  40                  45

Ser Ser Val Asn Tyr Met His Trp Tyr Gln Gln Lys Ser Gly Thr Ser
        50                  55                  60

Pro Lys Leu Leu Ile Tyr Ser Thr Ser Asn Leu Ala Ser Gly Val Pro
65                  70                  75                  80

Ser Arg Phe Ser Gly Ser Gly Ser Gly Thr Phe Tyr Ser Leu Thr Ile
                85                  90                  95

Ser Ser Val Glu Ala Glu Asp Ala Ala Asp Tyr Tyr Cys His Gln Trp
            100                 105                 110

Ser Ser Tyr Pro Tyr Thr Phe Gly Gly Gly Thr Lys Leu Glu Ile Lys
        115                 120                 125

<210> SEQ ID NO 44
<211> LENGTH: 136
<212> TYPE: PRT
<213> ORGANISM: Artificial Sequence
<220> FEATURE:
<223> OTHER INFORMATION: Antibody Sequence

<400> SEQUENCE: 44

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
                20                  25                  30

Pro Gly Ala Ser Val Lys Met Ser Cys Lys Ala Ser Gly Tyr Thr Phe
            35                  40                  45

Thr Asn Tyr Val Ile Tyr Trp Val Lys Gln Lys Pro Gly Gln Gly Leu
        50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Cys Asn Phe Leu Tyr Ala Met Asp Tyr Trp Gly Gln
        115                 120                 125

Gly Thr Ser Val Thr Val Ser Ser
        130                 135

<210> SEQ ID NO 45
<211> LENGTH: 381
<212> TYPE: DNA
<213> ORGANISM: Artificial Sequence
<220> FEATURE:
<223> OTHER INFORMATION: Antibody Sequence

<400> SEQUENCE: 45
atggagtcac agattcaggc atttgtattc gtgtttctct ggttgtctgg tgttgacgga     60
gacattgtga tgacccagtc tcacaaattc atgtccacat cagtaggaga cagggtcagc    120
atcacctgca aggccagtca ggatgtgaat actgctgtag cctggtatca aaaaaaatta    180
ggacaatctc ctaaactgct gatttattgg gcatccaccc ggcacactgg agtccctgat    240

```
cgcttcacag gcagtggatc tgggacagat tatactctca ccatcagcag tgtgcaggct    300
gaagacctgg cactttatta ctgtcagcaa cattatagca ctccgtacac gttcggaggg    360
gggaccaagc tggaaataaa a                                              381
```

```
<210> SEQ ID NO 46
<211> LENGTH: 411
<212> TYPE: DNA
<213> ORGANISM: Artificial Sequence
<220> FEATURE:
<223> OTHER INFORMATION: Antibody Sequence

<400> SEQUENCE: 46
```

```
atgggatgga gctatatcat cctcttttg gtagcaacag ctacagatgt ccactcccag     60
gtccaactgc agcagcctgg ggctgaactg gtgacgcctg ggcttcagt gaagctgtcc    120 tgcaaggctt ctggctacac cttcaccagc tactggatgc actgggtgaa gcagaggcct   180
ggacaaggcc ttgagtggat tggagagatt aatcctggca acgtcgtac taactacaat    240 gataatttca tgatcagggc cacactgact gtggacaaat cctccagcac agcctacatg   300
caactcagca gcctgacatc tgaggactct gcggtctatt actgtgcaag aagcctctac   360
ggtaccctct ttgcttcctg gggccaaggg actctggtca ctgtctctgc a           411
```

```
<210> SEQ ID NO 47
<211> LENGTH: 127
<212> TYPE: PRT
<213> ORGANISM: Artificial Sequence
<220> FEATURE:
<223> OTHER INFORMATION: Antibody Sequence

<400> SEQUENCE: 47
```

```
Met Glu Ser Gln Ile Gln Ala Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Asn Thr Ala Val Ala Trp Tyr Gln Lys Lys Leu Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Leu Ala Leu Tyr Tyr Cys Gln Gln His Tyr
            100                 105                 110

Ser Thr Pro Tyr Thr Phe Gly Gly Gly Thr Lys Leu Glu Ile Lys
        115                 120                 125
```

```
<210> SEQ ID NO 48
<211> LENGTH: 137
<212> TYPE: PRT
<213> ORGANISM: Artificial Sequence
<220> FEATURE:
<223> OTHER INFORMATION: Antibody Sequence

<400> SEQUENCE: 48
```

```
Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Thr
```

```
                  20                  25                  30
Pro Gly Ala Ser Val Lys Leu Ser Cys Lys Ala Ser Gly Tyr Thr Phe
                35                  40                  45

Thr Ser Tyr Trp Met His Trp Val Lys Gln Arg Pro Gly Gln Gly Leu
     50                  55                  60

Glu Trp Ile Gly Glu Ile Asn Pro Gly Asn Gly Arg Thr Asn Tyr Asn
 65                  70                  75                  80

Asp Asn Phe Met Ile Arg Ala Thr Leu Thr Val Asp Lys Ser Ser Ser
                 85                  90                  95

Thr Ala Tyr Met Gln Leu Ser Ser Leu Thr Ser Glu Asp Ser Ala Val
             100                 105                 110

Tyr Tyr Cys Ala Arg Ser Leu Tyr Gly Thr Leu Phe Ala Ser Trp Gly
         115                 120                 125

Gln Gly Thr Leu Val Thr Val Ser Ala
     130                 135
```

<210> SEQ ID NO 49
<211> LENGTH: 393
<212> TYPE: DNA
<213> ORGANISM: Artificial Sequence
<220> FEATURE:
<223> OTHER INFORMATION: Antibody Sequence

<400> SEQUENCE: 49

```
atggagacag acacactcct gctatgggtg ctgctgctct gggttccagg ttccactggt      60
gacattgtac tgacacagtc tcctgtttcc ttaactattt ctctgggcca gagggccacc     120
atctcatgca gggccagcca agtgtcagt gcatctagct atagttatat gcactggtac      180
caacagaaag caggacagcc acccaaactc ctcatcaagt atgcatccaa cctagaatct     240
ggggtccctg ccaggttcag tggcagtggg tctgggacag acttcaccct caacatccat     300
cctgtggagg aggcggatac tgcaacatac tactgtcaac acaattggga ggttcctccg     360
acgttcggtg gaggcaccaa gctggaaatc aag                                   393
```

<210> SEQ ID NO 50
<211> LENGTH: 423
<212> TYPE: DNA
<213> ORGANISM: Artificial Sequence
<220> FEATURE:
<223> OTHER INFORMATION: Antibody Sequence

<400> SEQUENCE: 50

```
atggactcca ggctcaattt agttttcctt gtccttgttt taaaaggtgt ccagtgtgat      60
gtgcagttgg tggagtctgg gggaggctta gtgcagcctg agggtcccg gaaactctcc      120 tgtgcagcct ctggattcac gttcagtagc tttggaatgc actgggttcg tcaggctcca     180 gagaagggc tggaatgggt cgcatatatt agtagtggca gtagtaccat ctactataga      240
gacacagtga aggccgatt caccatctcc agagacaatc caagaacac cctgttcctg       300 caaatgacca gtctaaggtc tgaggacacg gccatgtatt actgtgcaag aggggggta      360 gtagtttcga agatggaaa ctttgactac tggggccaag gcaccactct cgcagtctcc     420
tca                                                                    423
```

<210> SEQ ID NO 51
<211> LENGTH: 131
<212> TYPE: PRT
<213> ORGANISM: Artificial Sequence
<220> FEATURE:

<223> OTHER INFORMATION: Antibody Sequence

<400> SEQUENCE: 51

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Val Ser Leu Thr
            20                  25                  30

Ile Ser Leu Gly Gln Arg Ala Thr Ile Ser Cys Arg Ala Ser Gln Ser
        35                  40                  45

Val Ser Ala Ser Ser Tyr Ser Tyr Met His Trp Tyr Gln Gln Lys Ala
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Ala Asp Thr Ala Thr Tyr Tyr Cys
            100                 105                 110

Gln His Asn Trp Glu Val Pro Pro Thr Phe Gly Gly Thr Lys Leu
        115                 120                 125

Glu Ile Lys
    130

<210> SEQ ID NO 52
<211> LENGTH: 141
<212> TYPE: PRT
<213> ORGANISM: Artificial Sequence
<220> FEATURE:
<223> OTHER INFORMATION: Antibody Sequence

<400> SEQUENCE: 52

Met Asp Ser Arg Leu Asn Leu Val Phe Leu Val Leu Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Ser Ser Gly Ser Ser Thr Ile Tyr Tyr Arg
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Gly Gly Val Val Val Ser Lys Asp Gly Asn Phe
        115                 120                 125

Asp Tyr Trp Gly Gln Gly Thr Thr Leu Ala Val Ser Ser
    130                 135                 140

<210> SEQ ID NO 53
<211> LENGTH: 381
<212> TYPE: DNA
<213> ORGANISM: Artificial Sequence
<220> FEATURE:
<223> OTHER INFORMATION: Antibody Sequence

<400> SEQUENCE: 53
atgatgtcct ctgctcagtt ccttggyctc ctgttgctct gttttcaagg taccagatgt    60

```
gatatccaga tgacacagac tacatcctcc ctgtctgcct ctctgggaga cagagtcacc      120
aycagttgca gtgcaagtca gggcattagc aattatttaa actggtatca gcagaaacca      180
gatggaactg ttaaactcct gatctattac acatcaagtt tacactcagg agtcccatca      240
aggttcagtg gcagtgggtc tgggacagat tattctctca ccatcagcaa cctggaacct      300
gaagatattg ccacttacta ttgtcagcag tatagtaagc ttccgtacac gttcggaggg      360
gggaccaaac tggaaataaa a                                                381

<210> SEQ ID NO 54
<211> LENGTH: 399
<212> TYPE: DNA
<213> ORGANISM: Artificial Sequence
<220> FEATURE:
<223> OTHER INFORMATION: Antibody Sequence

<400> SEQUENCE: 54
atggaaaggc actggatctt tctcttcctg ttgtcagtaa ctgcaggtgt ccactcccag      60
gtccaactgc agcagtctgc ggctgaactg gtaagacctg gggcctcagt gaagatgtcc      120
tgcaagactt ctggctacat cttcactagc gaccggatgc actgggtaaa acagaggcct      180
ggacagggtc tggagtggat tggatacatt attcctagaa atttttatac taaatacaat      240
cagaaattca ggacaaggcc acattgactg cagacacatc ctccaataca gcctacatg      300 cagttgagca gcctgacatc tgaagactct gcagtctatt actgtgtgaa atctgacggg      360
gcctactggg gccaaggcac cactctcaca gtctcctca                             399

<210> SEQ ID NO 55
<211> LENGTH: 127
<212> TYPE: PRT
<213> ORGANISM: Artificial Sequence
<220> FEATURE:
<223> OTHER INFORMATION: Antibody Sequence
<220> FEATURE:
<221> NAME/KEY: misc_feature
<222> LOCATION: (41)..(41)
<223> OTHER INFORMATION: Xaa can be any naturally occurring amino acid

<400> SEQUENCE: 55

Met Met Ser Ser Ala Gln Phe Leu Gly Leu Leu Leu Cys Phe Gln
1               5                   10                  15

Gly Thr Arg Cys Asp Ile Gln Met Thr Gln Thr Ser Ser Leu Ser
                20                  25                  30

Ala Ser Leu Gly Asp Arg Val Thr Xaa Ser Cys Ser Ala Ser Gln Gly
            35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Ser Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Tyr Ser
            100                 105                 110

Lys Leu Pro Tyr Thr Phe Gly Gly Gly Thr Lys Leu Glu Ile Lys
        115                 120                 125

<210> SEQ ID NO 56
<211> LENGTH: 133
<212> TYPE: PRT
```

```
<213> ORGANISM: Artificial Sequence
<220> FEATURE:
<223> OTHER INFORMATION: Antibody Sequence

<400> SEQUENCE: 56

Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Val Arg
                20                  25                  30

Pro Gly Ala Ser Val Lys Met Ser Cys Lys Thr Ser Gly Tyr Ile Phe
            35                  40                  45

Thr Ser Asp Arg Met His Trp Val Lys Gln Arg Pro Gly Gln Gly Leu
    50                  55                  60

Glu Trp Ile Gly Tyr Ile Ile Pro Arg Asn Phe Tyr Thr Lys Tyr Asn
65                  70                  75                  80

Gln Lys Phe Lys Asp Lys Ala Thr Leu Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Val Lys Ser Asp Gly Ala Tyr Trp Gly Gln Gly Thr Thr
            115                 120                 125

Leu Thr Val Ser Ser
        130
```